(12) United States Patent
Wei et al.

(10) Patent No.: US 6,479,270 B1
(45) Date of Patent: Nov. 12, 2002

(54) ISOLATED HUMAN PHOSPHATASE PROTEINS, NUCLEIC ACID MOLECULES ENCODING HUMAN PHOSPHATASE PROTEINS, AND USES THEREOF

(75) Inventors: Ming-Hui Wei, Germantown, MD (US); Karen A. Ketchum, Germantown, MD (US); Valentina Di Francesco, Rockville, MD (US); Ellen M. Beasley, Darnestown, MD (US)

(73) Assignee: PE Corporation (NY), Norwalk, CT (US)

( * ) Notice: Subject to any disclaimer, the term of this patent is extended or adjusted under 35 U.S.C. 154(b) by 107 days.

(21) Appl. No.: 09/685,853

(22) Filed: Oct. 11, 2000

Related U.S. Application Data

(60) Provisional application No. 60/182,194, filed on Feb. 14, 2000.

(51) Int. Cl.$^7$ ................................................. C12N 9/16
(52) U.S. Cl. ...................................... 435/196; 435/196
(58) Field of Search ......................................... 435/196

(56) References Cited

FOREIGN PATENT DOCUMENTS

| WO | WO 01/53312 A | 7/2001 |
| WO | WO 01/73059 A | 10/2001 |

OTHER PUBLICATIONS

Meyers RA (Accession No. AX260345) 38692 and 21117: dual specificity phosphatase molecules and uses therfor. Patent: WO 0173059–A (2001).*

Wishart, MJ, Denu, JM, Williams JA, and Dixon, JE (Accession No. U34973) A single mutation converts a novel phosphotyrosoine binding domain into a dual–specificity phosphatase J. Biol. Chem 270 p26782–5 (1995).*

International Search Report Feb. 26, 2002.

Adachi, J et al.: "Mus Musculus Adult Male Kidney cDNA clone": Database EMBL Online Accession No. AK002822: Feb. 8, 2001.

National Institutes of Health: "NIH–MGC–69 Homo sapiens cDNA clone: 3887425": Database EMBL Online Accession No. BE877007: Sep. 29, 2000.

Wishart, M et al.: "A single mutation converts a novel phosphotyrosine binding domain into a dual–specificty phosphatase": The Hournal of Biological Chemistry, vol. 270 No. 45 pp. 26782–26785: Nov. 10, 1995.

Dayton, M et al: "Tyrosine Phosphatase–Like Protein Homolog HSTYXB (Fragment)" Database Swisprot Online Accession No. Q99850: May 1, 1997.

National Cancer Institute: "Soares–NhHMPu–S1 Homo sapiens c DNA clone: 2124769" Database EMBL Online Accession No. A1492892: Mar. 17, 1999.

* cited by examiner

*Primary Examiner*—Ponnathapu Achutamurthy
*Assistant Examiner*—Sheridan L. Swope
(74) *Attorney, Agent, or Firm*—Celera Genomics; Lin Sun-Hoffman

(57) ABSTRACT

The present invention provides amino acid sequences of peptides that are encoded by genes within the human genome, the phosphatase peptides of the present invention. The present invention specifically provides isolated peptide and nucleic acid molecules, methods of identifying orthologs and paralogs of the phosphatase peptides, and methods of identifying modulators of the phosphatase peptides.

8 Claims, 33 Drawing Sheets

```
  1  ATGGAGGACG TGAAGCTGGA GTTCCCTTCC CTTCCACAGT GCAAGGAAGA
 51  CGCCGAGGAG TGGACCTACC CTATGAGACG AGAGATGCAG GAAATTTTAC
101  CTGGATTGTT CTTAGGCCCA TATTCATCTG CTATGAAAAG CAAGCTACCT
151  GTACTACAGA AACATGGAAT AACCCATATA ATATGCATAC GACAAAATAT
201  TGAAGCAAAC TTTATTAAAC CAAACTTTCA GCAGTTATTT AGATATTTAG
251  TCCTGGATAT TGCAGATAAT CCAGTTGAAA ATATAATACG TTTTTTCCCT
301  ATGACTAAGG AATTTATTGA TGGGAGCTTA CAAATGGGAG GAAAAGTTCT
351  TGTGCATGGA AATGCAGGGA TCTCCAGAAG TGCAGCCTTT GTTATTGCAT
401  ACATTATGGA AACATTTGGA ATGAAGTACA GAGATGCTTT TGCTTATGTT
451  CAAGAAAGAA GATTTTGTAT TAATCCTAAT GCTGGATTTG TCCATCAACT
501  TCAGGAATAT GAAGCCATCT ACCTAGCAAA ATTAACAATA CAGATGATGT
551  CACCACTCCA GATAGAAAGG TCATTATCTG TTCATTCTGG TACCACAGGC
601  AGTTTGAAGA GAACACATGA AGAAGAGGAT GATTTTGGAA CCATGCAAGT
651  GGCGACTGCA CAGAATGGCT GA
```

FEATURES:

Start codon: 1
Stop codon: 670 cDNA Sequence:

```
   1  AACACCACGC GTCCGGCAGC GGCATGGCGG CCGGGTGTAA GACGCCCGAC
  51  CCTCCTCTTC CCTGTCTTCG CCGCCGCCGC TGCTGGAGTC ACTGGGACCC
 101  TGTAGTCTGC GTGTGTTAGT TGTAATCCCG CCGCCCTCCT GTCAGCCCTC
 151  CGCTCCGCCG GCCCTCCTTC CTTCCGCCGC CGCAGCCAGC CCGAGGGTCG
 201  GCCGGCTGTG TAACACTCTC CCACCCCACC CACCAGCCCG CGGGCCAGCA
 251  CCATGGAGGA CGTGAAGCTG GAGTTCCCTT CCCTTCCACA GTGCAAGGAA
 301  GACGCCGAGG AGTGGACCTA CCCTATGAGA CGAGAGATGC AGGAAATTTT
 351  ACCTGGATTG TTCTTAGGCC CATATTCATC TGCTATGAAA AGCAAGCTAC
 401  CTGTACTACA GAAACATGGA ATAACCCATA TAATATGCAT ACGACAAAAT
 451  ATTGAAGCAA ACTTTATTAA ACCAAACTTT CAGCAGTTAT TTAGATATTT
 501  AGTCCTGGAT ATTGCAGATA ATCCAGTTGA AAATATAATA CGTTTTTTCC
 551  CTATGACTAA GGAATTTATT GATGGGAGCT TACAAATGGG AGGAAAAGTT
 601  CTTGTGCATG GAAATGCAGG GATCTCCAGA AGTGCAGCCT TTGTTATTGC
 651  ATACATTATG GAAACATTTG GAATGAAGTA CAGAGATGCT TTTGCTTATG
 701  TTCAAGAAAG AAGATTTTGT ATTAATCCTA ATGCTGGATT TGTCCATCAA
 751  CTTCAGGAAT ATGAAGCCAT CTACCTAGCA AAATTAACAA TACAGATGAT
 801  GTCACCACTC CAGATAGAAA GGTCATTATC TGTTCATTCT GGTACCACAG
 851  GCAGTTTGAA GAGAACACAT GAAGAAGAGG ATGATTTTGG AACCATGCAA
 901  GTGGCGACTG CACAGAATGG CTGACTTGAA GAGCAACATC ATAGAGTGTG
 951  AATTTCTATT TGGAAGGAG AAAATACAAG AGAAATTAT AATGTAAAAT
1001  GGTAAAAACA TAAGTAGTTT TTTTTTCAAT TACATGTTGC TTCCAGACAT
1051  ACTTCTCTGC AACTTGTTGA GCAACATTTT AAGATGTTGG ACTTCTGCAA
1101  TAGATGACAC TGATGGTTTT ACTCCTTTTT TTTAAAAACA CATGCGCGCG
1151  CACACACACA TGCTTTACAA GTTTTATTAT AAACCAAGAA TTTTGGACTT
1201  GCAAAAAAA AAAAAAA
```

FEATURES:

Start codon: 253
Stop codon: 922

FIGURE 1, page 1 of 2

Homologous proteins:
Top 10 BLAST Hits

```
gi|2137698|pir||I49365  protein tyrosine phosphatase - mouse >gi...    462  e-129
gi|2137697|pir||I49364  protein tyrosine phosphatase - mouse >gi...    356  1e-97
gi|1842088 (U87169) tyrosine phosphatase-like protein homolog h...    141  5e-33
gi|4758206|ref|NP_004409.1|| dual specificity phosphatase 2 >gi...     94  9e-19
gi|4758212|ref|NP_004411.1|| dual specificity phosphatase 8 >gi...     93  2e-18
gi|6679156|ref|NP_032774.1|| neuronal tyrosine/threonine phosph...     93  2e-18
gi|4758204|ref|NP_004408.1|| dual specificity phosphatase 1 >gi...     92  5e-18
gi|1050849|emb|CAA58710| (X83742) MAP kinase phosphatase [Xenop...     91  8e-18
gi|4150963|emb|CAA77232| (Y18620) DsPTP1 protein [Arabidopsis t...     90  1e-17
gi|6714641|dbj|BAA89534.1| (AB036834) MAP kinase phosphatase [D...     90  1e-17
```

EST

```
gi|2059098|gb|AA404320.1|AA404320 zw36g07.s1 Soares_total_fetus...    761  0.0
gi|2810244|gb|AA761314.1|AA761314 nz21c05.s1 NCI_CGAP_GCB1 Homo...    630  e-178
gi|1472397|gb|AA011350.1|AA011350 zi01b04.s1 Soares_fetal_liver...    607  e-171
gi|1230791|gb|N73506.1|N73506 za49c05.s1 Soares fetal liver spl...    597  e-168
gi|4389706|gb|AI497724.1|AI497724 ti50c07.x1 NCI_CGAP_Lym12 Hom...    379  e-103
```

EXPRESSION INFORMATION FOR MODULATORY USE:
gi|2059098|gb|AA404320.1    Human total fetus
gi|2810244|gb|AA761314.1    Human Germinal B cell
gi|1472397|gb|AA011350.1    Human fetal liver
gi|1230791|gb|N73506.1      Human fetal liver spleen
gi|4389706|gb|AI497724.1    Human Lymph node PCR-BASED TISSUE SCREENING PANEL:
Human fetal brain, human Brain, human heart, human liver, human lung, human placenta, human thyroid.

FIGURE 1, page 2 of 2

```
  1  MEDVKLEFPS LPQCKEDAEE WTYPMRREMQ EILPGLFLGP YSSAMKSKLP
 51  VLQKHGITHI ICIRQNIEAN FIKPNFQQLF RYLVLDIADN PVENIIRFFP
101  MTKEFIDGSL QMGGKVLVHG NAGISRSAAF VIAYIMETFG MKYRDAFAYV
151  QERRFCINPN AGFVHQLQEY EAIYLAKLTI QMMSPLQIER SLSVHSGTTG
201  SLKRTHEEED DFGTMQVATA QNG
```

FEATURES:
Functional domains and key regions:

------------------------------------------------------------

[1] PDOC00005 PS00005 PKC_PHOSPHO_SITE
Protein kinase C phosphorylation site
201-203 SLK

------------------------------------------------------------

[2] PDOC00006 PS00006 CK2_PHOSPHO_SITE
Casein kinase II phosphorylation site
205-208 THEE

------------------------------------------------------------

[3] PDOC00007 PS00007 TYR_PHOSPHO_SITE
Tyrosine kinase phosphorylation site
Number of matches: 2 1 15-23 KEDAEEWTY 2 142-149 KYRDAFAY

------------------------------------------------------------

[4] PDOC00008 PS00008 MYRISTYL
N-myristoylation site
Number of matches: 2 1 123-128 GISRSA 2 197-202 GTTGSL

------------------------------------------------------------

Membrane spanning structure and domains:
```
Helix  Begin  End   Score  Certainty
  1     123   143   0.626  Putative
```

FIGURE 2, page 1 of 2

BLAST Alignment to Top Hit:
```
>gi|2137698|pir||I49365 protein tyrosine phosphatase - mouse
        >gi|1063626|gb|AAA87037.1| (U34973) protein tyrosine
        phosphatase-like [Mus musculus]
        Length = 223

Score =  444 bits (1131), Expect = e-124
 Identities = 214/223 (95%), Positives = 221/223 (98%)

Query: 1    MEDVKLEFPSLPQCKEDAEEWTYPMRREMQEILPGLFLGPYSSAMKSKLPVLQKHGITHI 60
            MEDVKLEFPS+PQCK+DAEEWTYPMRREMQE+LPGLFLGPYSSAMKSKLP+LQKHGITHI
Sbjct: 1    MEDVKLEFPSVPQCKDDAEEWTYPMRREMQEVLPGLFLGPYSSAMKSKLPILQKHGITHI 60

Query: 61   ICIRQNIEANFIKPNFQQLFRYLVLDIADNPVENIIRFFPMTKEFIDGSLQMGGKVLVHG 120
            ICIRQNIEANFIKPNFQQLFRYLVLDIADNPVENIIRFFPMTKEFIDGSLQ GGKVLVHG
Sbjct: 61   ICIRQNIEANFIKPNFQQLFRYLVLDIADNPVENIIRFFPMTKEFIDGSLQNGGKVLVHG 120

Query: 121  NAGISRSAAFVIAYIMETFGMKYRDAFAYVQERRFCINPNAGFVHQLQEYEAIYLAKLTI 180
            NAGISRSAAFVIAYIMETFGMKYRDAFAYVQERRFCINPNAGFVHQLQEYEAIYLAKLTI
Sbjct: 121  NAGISRSAAFVIAYIMETFGMKYRDAFAYVQERRFCINPNAGFVHQLQEYEAIYLAKLTI 180

Query: 181  QMMSPLQIERSLSVHSGTTGSLKRTHEEEDDFGTMQVATAQNG 223
            QMMSPLQIERSL+VHSGTTGS+KRTHEE+DDFG MQVATAQNG
Sbjct: 181  QMMSPLQIERSLAVHSGTTGSVKRTHEEDDDFGNMQVATAQNG 223
```

Hmmer search results (Pfam):
Scores for sequence family classification (score includes all domains):

| Model | Description | Score | E-value | N |
|---|---|---|---|---|
| PF00782 | Dual specificity phosphatase, catalytic doma | 221.5 | 1.2e-62 | 1 |

FIGURE 2, page 2 of 2

```
   1  TTGAAATCCA  AAAATATCTG  AAGCTACATT  TGGACCCCTG  TAAATAATGT
  51  AATGTATAAG  GATTTTTCCA  AAATAAGTCT  TAATTTCAGT  TTTCATATAT
 101  CAACAAAAAG  GTACTATTAG  GAGTACATAG  TTGCCACACT  TGAGACATAT
 151  TCCAAATGCA  TACACCTAAC  GGTACTACTA  TTACAGAACA  GCACATTCTA
 201  ATCCACATAT  ACACGAGTTT  TAATTAAATT  TAGCACTATG  TCTATAATCA
 251  GAATGAATAC  CTGGAATACA  TGTTTCTAGC  AGGAATATTT  GTTAGCAGCT
 301  TTAAGGTACT  TGAAATCACC  ATAATCATTT  CTATTTTAAA  TTTAAATTTC
 351  ACTACTGGGG  TAAATTCCAT  GAGGGAAGGT  TGTGGCTATG  AATTTTTATT
 401  TATTCTTTTT  CTTTTGTGGT  AAATATGGAG  AACTTACCAA  ATCTCTTATA
 451  TAGCCTGGCT  GTAGATGGCA  ATGCGAGGAA  AGAAAAAGGA  AGCAGAAAGA
 501  AAAAAAAAGG  CAATCAGAAA  AAATGGCAAC  GAAGCAAAGA  AAAAGTTGCG
 551  GTCACCTGCA  AACCAAAATT  CCAGCCAAAA  GTCATGCAAA  AAACTACTTT
 601  AGGTAGAAAC  CAAGCAAAGT  AAATGCAAGA  ATGAAAAATG  AAAATGAGGA
 651  AGCAGCAATT  ACTTTCCATT  TAGAACACTG  AGAAACACTC  CACATTATTT
 701  TAGAATGTTA  AATGTTGCTA  AAGAACCTAA  GGGTAGAAAT  TTGTAGGGAG
 751  AAGATAAAAA  GAGCAAATAT  TTCTTTCCCC  CTACATCGTG  TACCCAGTTA
 801  CATCGTGTAC  CCAGTTCTCA  CCGGTTAAGG  TAAAGCCAAT  TATTTTAGTA
 851  GCAAATAAA   AGTATCCAAA  AGCCTTTAAA  GTCTTCTCAG  ATTTAGTCAG
 901  ATAATATGAT  CCATGCACTG  CTTTTCAGAA  ATAAGAATTT  GAAGGCATAA
 951  AATAAGTGCA  GTGCCCATCT  GTTTCTTTTT  TTACACAAGA  AAAGCAAACC
1001  CCTCAGTTAC  CATGTGTTTT  TTGCATCCTT  TTTCCTGGAA  GGGAAAACAA
1051  AGAGATGCCG  TATACTACAT  GAGGAATTTC  GGCTTTATGG  CATTAGTCAT
1101  TTCCATTTAG  ATTAACATAA  ATCAACATAT  AGAATAATTC  TTCAAAATTT
1151  AAAAATCCAG  TTTGAGAGTC  ATATTTATTT  AAAAATACCC  ACAGCATGTT
1201  TAGTTAATAT  ATATATAATT  GAAGGGAATT  AAAGTAGGTT  AAATACAACA
1251  GGTTATTTTG  ATAGACCCAA  AAGAAAACTA  CGAGTCTATG  CCCAGGTAGG
1301  GAAGAATGTC  CTTGTGGCCT  GCACATCTTC  CTACAGCCTC  CAGAACGCAA
1351  CTGGATACAG  CTTAATAATT  ACTGAGCACT  ATGTCCAGTG  TGACTAGTGT
1401  GGTATCTGAC  ACACAGTAGC  AACTAAACTT  CTGAATGTCA  CTACTTACTA
1451  GGCACCAGGG  CAATAACATC  ATGGTCGCTA  TTCTCTGGAA  ACAATTTTTT
1501  TTTCTGACAC  GGAGTTTCAC  TCTTGTTGCC  CAGGCTGGAG  TGCAATGGCG
1551  CCATCTTGGC  TCACTGCAAC  CTCCACCTCC  CAGGTACAGG  TGATTCTCCT
1601  GCCTCAGCCT  CCCAAGTAGC  TGGCATTATA  GGCGTGCACC  ACCATGCCTG
1651  GCTAATTTTT  GTAGTTTTAG  TAGAGATGGG  GTTTCACCAT  GTTGGCCAGG
1701  CTGGTCTCGA  ACTCCTGACC  TCAGGTGTTC  CACTCACCTC  GGCCTCCCTA
1751  AGTGCTGGGA  TTACAGGTGT  GAGCCACCGC  ACCTAGCCCA  ACACAACTAT
1801  TCAATAGAAA  TTTCTCTCTC  GGTCAGGCAT  GGTGGCTCAC  GCCTGTAATC
1851  CCAGCACTCT  GGGAGGCTGA  GGTGGGTGGA  TCATCTGAGG  TCAGGAGTTC
1901  AAGACCAGCC  TGCCAATACA  GTGAAACCCC  ATCTCTTCTA  AAAGTACAAA
1951  AATTAGCCAG  GTGTGGTGGT  GGCGCCTGTA  GTCCCAGCTA  CTCAGGAGGC
2001  TGAGACAGGA  GAATCTCTTG  TACCCGGGAG  GCAGAGGTTG  CAATGAGCCA
2051  AGATCATGCC  ATTGCACTCC  AGCCTGGGCA  ACAGACTCTG  TCTCAAAAAA
2101  AAAGAAATTT  CTCTCTTAAG  TTACTGGTAC  TATAAGTAAT  TTAAATTGGA
2151  CTTTCAGATC  TTCAATTTCT  CTAGTCTCTA  CTTTTCTTCC  TTGAATCAGT
2201  CTTGAGAGCA  GAACATACTG  TTCTTTAAAA  GCTGCCGTGG  CAAAATGCCA
2251  ACAGATAAAA  ATTGTATATA  CCTTTTCTCT  TGGTATGTTG  TCAAATCCAT
2301  CCCCCATTTT  AGAATTATTT  TGTGTTGTAT  TTTCAAATGC  AAACTAGTAT
2351  AGATCTTTTG  AGTTGTGTTT  TTTGTTTATA  TGTTCATTTG  ACTTAACTGA
2401  TTTTTTTGTG  GTATAATTTT  TCATTGAGGT  ATAATTACAT  TAAAAAAATG
2451  TAGATTCTTA  AGTGTACATT  TCAAATATGT  TTGGACAAGT  TATATATCTG
2501  TGTAACCATC  ACCCCAATCA  AGTGTGTGGT  TTATTTAAAA  AACATTATTT
2551  GAAATTTTTT  AGATTTAAGA  GATCTTAAAT  CTACCTGGAG  CAAAACCTCT
2601  TAATATAAAT  GGTTTTACCT  AGCATGGAAG  TCTAGGTCTA  TTAAGAATTA
2651  TGATGTGTAC  ACCTAACTAA  GGTGATATTT  GACTTAGAGT  ATTTGAAAGT
2701  ACATTAAAAA  TCTTGACTAA  CTTTTTAAGA  AAGATTTAAC  TTCTTTTCTA
2751  GGTGATAGAA  TTACCTCTTA  CAAACCCAGA  GTTATTTCAG  CGTGTAGGAA
2801  TAATACCTCC  AAAAGGCTGT  TTGTTATATG  GACCACCAGG  TTGGTATTGA
2851  ATTATTTCTA  CTCCACCAAT  AAGATAAATG  AATTAAGGAA  TTAAAAAAAA
2901  AAAGCAATT   TTTTATTTT   TATTTTTTG   AGACACGGTC  TCACTCTGTT
2951  GCCCAGGCTG  TAGTGCAGTG  GCACAATCTG  GGCTAACTGC  AACCTCTGCC
3001  TTCCGGGCTC  AAGTGATTCT  CCCACCTCAG  TCTCCCACGT  AGCTGGGACT
3051  GCAGGCGTGC  ATCACCATGT  CTGGTTAATT  TTTGTATGTT  TTGTAGAGAA
```

FIGURE 3, page 1 of 29

```
3101  GCAATTTTGC CATGTTGCTC AGGCTATCTC AAACTCCTGG ACTCAAGCGA
3151  TCTGCCCACC TTAGCCTCCC AAAATGTTGG GATTACAAGC ATAAACCACT
3201  GCGCCTGGCC ATAAGGTGGA AATTTGATGT GGGCAGTTCC AACTTCTCCT
3251  CTCTTCAGAG TGAGAATGAG ATAGGATATT TATGTCTACT GTTCTTTGAG
3301  GCATGCTTAG TGCATTTGTG CCTCACAGTA CATTTATCTT AACAGGCCAT
3351  GTGATTCTAG TGCAACAGTC CTCAAATTGT GGTTCACAGA CCCAGAGGTG
3401  CTTTCATGGA CTCTGTAAGG TCAAAACTAC TTTATAATAC TGAAATGTTA
3451  AGCCAGGCGC AGTGGCTCAC ACCTGTAATC CCAGCACTTC GGGAGGCCGA
3501  GGCAGGCAGA TCACCAGAGG TCAGGAGTTT GAGAGCAGCC TGGCCAACCA
3551  ACATGATGAA ACCCTGTCTC TACTAAAAAT ACAAAAATGA GCCAGGCGTG
3601  GTGGCGTGCA CCTGTAATCC CAGCTACTCG GGAAGCTGAG GCAGGAGAAT
3651  TGCTTGAACC TGGGAGGCAG AGGTTGCAGT GAGCCGAGAT TGCCCCACTG
3701  CACTCCAGCC TGGCTGACAG AGTGAGACTC CTTCTCAAAA AAAAAAAAAA
3751  AAAAAAAAAA ATTTTTTATA TAAAGCAAAT GTACCTATAG CATACTGCTT
3801  GACATATGTA GCCCCACAAT GACACAAAAC AAAAAACTAA AATGTTGTTT
3851  GGCTCTTCCA CTGTGTTGAC ATTTGTGCTG ATGGTGCAAG AGCACCATGG
3901  GTAAAATTAA ATTACTTGCA CTGTAGTGTG AATCAGCATT AGTGGCATGA
3951  AACGGTGCTA GTTAGTAGCC ATTGCGTTCT TGACTGCCAC ATACTTGCAG
4001  TGTAAAAAAA AAAAAAAGTC AGTTTCACTA TAAAGTCCTT GGTGAAACAG
4051  TAAAAATTAT TAATTTTGTT AAATCTTCAT CTTTGGGTAA TATTTGTGT
4101  TCTTCATGAT AAAAGGGAAA ATAAATATAA AGTACTGCTG CATATTGAAT
4151  AAGATAGTTG TCTTTAGGAA AAGCACTTGT GCAGTTATTT AAGTTGCCAG
4201  CTGAATTCAT TGCTTTTTAT GGAATACTAT TTTTGCTTGA ATGGACCATT
4251  TACAGATATG CTGTGATTAT CAGACTGGTT ATTGGTTATT AGTTATTGAT
4301  TACTCAAGAC TGGTTTTTGG TTATTTGGCG CACATTTTTT CCAAAGCGAA
4351  CAAATTAAGC CTGTCATGTT AAACAACTGA CACCATCTAT TGCCATTGAT
4401  AAAATATGAA ATGTCAAGTG AAAATTAGAA TTTTTAGAAA CATATATCTG
4451  GCACTATGTG GTTGAAGCTT TTTCTTTTTT TCTTTTCTTT TCTTTTTTTT
4501  TTTTTTGATA AGGTGTTACT CTGTTACCCA GGCTGGAGTG CAGTGGCGTG
4551  ATCATCCTGG CTCGCTGCAA CTTCTGCCTC TTGGGCTCAG GTGATTCTTC
4601  CACCTCAGCC TCCTGAGTAG CTGGTACTAC AGGTGTGTGC CACCATGCCA
4651  GGCTAATTTT TGTGTTTTTA GTAGAGGCAG GGTTTTGCCA TGTTGCCCAG
4701  GCTGGTCTTG AATTCCTGGG CTCAAGCAAC CCGCCCACCT CAGCCTCCCA
4751  AAGTGCTGGG ATTACAGGCA TGAGCCACAA TGTCCAGCCA CGGCAGCTTT
4801  CTAATATATT AATACTTAAA GACTTTTCTG ATGAGATAAG TGGTGAGAAT
4851  AACAAAAATT TTTTATAATG TGTGGTGGAA AATGTCAACA TTTGGAAGAT
4901  TTGCATAACT CAACCAGTAG TTTCCAAATA ATCAATGCTT GATATTAAAA
4951  TATTCATAAG TAAAACATCC AGTCAGTGCA CAGGATAGAC CAATGTATTT
5001  TAATGTAACA GAAGTTCTG TCATAGTCCA TGTTGTAAGT AGATAGCTAT
5051  TATAAAAAG ACAAAGTGT TGCAAGATG TAGAGAAAAG AGAAAGAACC
5101  CTTGTACACT ACTGGTGGGA ATGTAAATTA GCACAGCCAT TTTTGAAAAC
5151  ATGGAGGTTC CTCAAAAAAC TAAAAATAGA ATTACCATAT GATTCAGCAA
5201  TCCCACTTCT GGGTTTATAT CTAAAGGAAT TGAAATCAGT GTGTCAGAGA
5251  TAGCTGCACT CCCATGATTA TTTCACAATA GCCAAGATAT AGAAACAGCC
5301  TAAAAATTGC CCATCAATGG ATGAATGGAT AAAGAAAATG TGGTAGCCGG
5351  GTGCAGTGGC TCATACCTGT AGTGCCAACA CTTTGGGAGG CCGAGGCGGG
5401  CGGATCACCT GAGGTCGGGA GTTCGAGACC AGCCTGACCA ACATGGAGAA
5451  ACCCCGTCTC TGCTGAAAAT ACAAAATTAG CTGGGTGTAG TAGTTCATGC
5501  CTGTAATCCC AGCTACTCGG GAGGCAGAGG CAGGAGAATC ACTTGAACCT
5551  GGGAGGCAGA GGTTGCAGTG AGCTGAGATC ATGCCATTGC ACTCCAGCCT
5601  GGGCAACAAG AGTGAAACTC CATCTCAAAA AAAAAGAAA AAGAAATGTG
5651  GTAAATACAC ACATTGGAAT ACTATTCAGC CTTAAAAAAG GAAACTCTGT
5701  CATTTGTGAC AATATGGATG AATCTAGAGG ATGTTATACT AAGTGAAATA
5751  AGCCAGACAC AGAAAGACAG TTACCACATA ATCTCATTTT CATGTGGAAT
5801  CTTAAAAAAT TGAACTCGTA GAAACCAAGA GTAGAATGGT GGTTACCAGA
5851  AGTTGTGGTG GTGTATGGGG ATAGGGGAGA TGTTGGTCAA AGGATATAAA
5901  GTTCACTTAG ACAGGAGGAA TAAGTTCTAG GTGACATATT GCATAGCATG
5951  GTGACTATAA TTAATAATGT ATTAGCTATT TCAAAATTGC TAAAAGTAGA
6001  TTTTAAATGT TCTAACCACA AAGTAATGCT AAGCATGTGA GGCGATGGAT
6051  ATGTTGATTT GCCTGATTTA ATCATTCTTC AATATATACA TGTATCATAA
6101  TTTAACCCAT AAATATACAA TTTATTTGTC AATTTAAAAT AGATTTTAAA
6151  AATTATAACA TTTTGATTAA AATTTTAATG TTGACAGCAG AAGTACTTTG
6201  GAATTTTTTT TTTTTTTTT TTTTTGAGA CAGAGTCTTG CTCTGTCACC
```

FIGURE 3, page 2 of 29

```
6251  CAGGCTGGAG TGCAGTGGCG AGATTATAAG CTCACTGCAA CCCCCACCTC
6301  CCGGATTCAA GCGATTCTCC TGCCTCAGCC TCCCAGTAG GTGGGACTAC
6351  AGGCATGTGC CACCACGCTC AGCTAATTTT TTGTATTTTT AGTAGAGACG
6401  GGGTTTCACT GTGTTTCGAT CTCCTGACCC TGTGATCTGC CCGCCTCAGC
6451  CTCCCAAAGT GCTGGGATTA CAGGTGTGAG CCACCACACC TGGCCAAGTA
6501  CTTTGGAATT TTAAATGAAA ATTCTATTTA GGATTTAGCT TTCATTTTGG
6551  AAAATTTACT TGCCAAACGA TTATATTCTT AAAAGGATTT TAAAAATTTG
6601  TTTCACATAG GCCGGGTGCG GTGGGTTCTG CCTGTAATCC CAGCACTTTG
6651  GGAGGCTGAA GTGGCAGGAT CACCTGAGCC CAAGAGTTCA AGACCAGCAT
6701  GCGCCAACAC AGAGAGACCC CGTCTCTGAA AAACAAACAG ACAAACAAAA
6751  AACTTAGCTG TGCGTGATGG CACATGCCTG TCATCCCAGC TACTTGGGAG
6801  GCTGAGGTGG GAAAATCGCT TAGGTCTGGG AGGTCAAGGT TGCAGTGAGC
6851  TGTGATCTCG CCACACTCCC AGCCTAGGTG ACAGAGTGAT TGCCTGTCTC
6901  AAAACAAATT TTTTTCTACC TTACCATCTA ATTAAGACTT CTTTTGTCAT
6951  TCTTAGGTAC GGGAAAAACA CTCTTGGCAC GAGCCGTTGC TAGCCAGCTG
7001  GACTGCAATT TCTTAAAGGT AAAGGGAAGA TTATTTGTA CTTATTGAAA
7051  TTTAATTTTA CTTGAATTAT CTTATATTTA CCTTACTGTT TTTCCTTTAA
7101  TCAGGTTGTA TCTAGTTCTA TTGTAGACAA GTACATTGGT GAAAGTGCTC
7151  GTTTGATCAG AGAAATGTTT AATTATGCTA GAGATCATCA ACCATGCATC
7201  ATTTTATGG ATGAAATAGA TGCTATTGGT AAGAATAACA CCCTTGTTGA
7251  AAGTTTTAGG ACTTTTTTTT AAATGTAAAA GAACCTTTTT CCCTCTCTTA
7301  ATCTGTAATT GTGACTTGTA TGAAGTAGAT ACCACAATGA ATCAGATGTT
7351  AGTTTAACCA ATTTTAATAA ATAACCTTTC ATGGCCGGGT GTGGTGGCTC
7401  ATGCCTGTAA TCCCAGCACT TTGAGAGGCC AAGGTGGGCA GATCACCAGG
7451  TCAGGAGATC GAGACCATCT GGCCAACATG GTGAAACCCT GTCTCTACTA
7501  AAAATACAAA AATTAGCTGG ATGTGGTGGC ACATGCCTGT AATCCCAGCT
7551  ACTGAGGAGG CTGAGGCACG AGAATCGCTT GAACCCAGGA GACGTAGGTT
7601  GCAGTGAGCC GAGATCACAC CACTGCACTC CAGCCTGGCG ACAGAGCGAG
7651  ACTCCGTCTC AATAAATAAC CTTTCACTTT AACAAAATGA GAAATGTTAC
7701  ACCAAAATCA AGTCTAACTT TGTCAGCATA ATTCTTGCTC TTTAATTTTC
7751  ATCTTAATGT TTAAGCCAC AGACTGTTAT GTTCTGTTTT CTTAAATGAT
7801  GGTTGTAGAG GAAAAGAGTA ATGCATATAA ATTTCCAAAT CTACTATCTT
7851  AGGTGGTCGT CGGTTTTCTG AGGGTACTTC AGCTGACAGA GAGATTCAGA
7901  GAACGTTAAT GGAGGTAATA TTTGGTAAAG GGGGTTTATA AAGAAACCAA
7951  TGTTTATTAA ATGAAGAACT GAACATTGCA TATTTGATAG TCAAAATATA
8001  TAGAACATTT TAAATGAAAT ATGAAATTTG AAAATATTGT CAGGAACAAA
8051  CATGTTTCTC TATCACAAAC TCTAAGCAAA ATGACTACTG GAAAATAAGG
8101  CTATCTGCCA AATTCCATTT GGTATACACC TGTACTATTC TGTGTTTTTT
8151  TGAGTAGATC AGTCATTCAT ATATTTAAAT TCTTATGAAT GTGATCTTGC
8201  GGTAGTTTTA TGAAGACATT TTTTGAATG GTCATATTAA GACTGTTGGC
8251  AATAAATGAG CTATAATTAT GTATGAAGCT GCTCTAAAAA TTATTTTTTT
8301  CTCTCACTTT ATTGCTGAGA CTGAGGCAAC TAAAATAGTT TTGATAATTG
8351  AAGAGGATAG ATGACAGAAT GAAAGAATGC ACATAAAGCC TTCCTCCAGT
8401  TTTACCTTTC CCCACTCCAA ATTCTGTGAA AGTGATATCA AGAGTCCAAA
8451  TACATTTTCC ACTTCAAATA GAAACTAGGT AGCATGGGTA ATGCAGTGTC
8501  AAATTCTTTC TCCTTAGAAG TATTTGAAAA ATCTTTTTTC ATAAATTATA
8551  CAGATCCGCT CAGAAGATAA CATAGCATTT GGAAATTATA AAATCTCTTA
8601  GAAACCTTAA ATTGAGATAT TTTTAAATAA CACAAATACT CATTTTATT
8651  CAAGTAACTA ATATATCATC AACTAACACA TTGTCAGGAC TAGCTATATT
8701  TTTAGAGAGG TTTGTTAAAT GCAGTAAAGG TTTTTCATTT ATTCAAGAAA
8751  ACTTTAGAAA TTGAGGACAA TATTTTTTAT GTCTTTTAGT ATTTCTGTGT
8801  ACAGTAGAAT TATTTGAAAA AATAGGCCAG GCATGGTGGC TTCTGCCTGT
8851  AATCCCAGCA CTTTGGGAGG CCCAGCTGGG CAGATCATGA GGTCTGAGCA
8901  TTGAGACCAG CCTGACCAAC GTAGCGAAAC ACCATCTCTA GTAAAGATAC
8951  AAAAATTAGC TGGGCGTGGT GGCGTGTGCC TGTAATCCCA GTTACTCAGG
9001  AGGCTGAGGC AGGAGAATTG CTTGAACCCA GGAGGTGAGG TTGCAGTGGG
9051  CTGAGATCGC CCCATTGCAC TCCAGCCTGG GTGACAGAGC GAGAGTCTGT
9101  CTCCAAAAAA AAAAAAAAAA AAAGCAGTC CCAGCTACTC AGGAGGTTGA
9151  GGTGGGAGGA CTGGTCGAGC CCAGGAGGTG AAGGTTGCAG TGAGCGATGA
9201  TCAGGCCACA GTACTCCAGC CTGGGTGACA GAGTGAAACT CTGTCTCAAA
9251  AAAAAAAGA CTATCAAATA TGCAATGTTC ATTATCAGTT TATTATCAAA
9301  TTTGTAGAAA AATCTTTGTA TCCATTTATC CTAATATAAA TGTTATGTCT
9351  GACATATCAT AAGCACTTTA TATATTGGAT TTTATTATTA GCTTTTCCTT
```

```
 9401 TAAAAAATAA TTGATGAAAT TTTGGACATT GGAAATTAGA TCCACATAGT
 9451 TTAATTTCAT AATTCTTGAC ATGATGGAAG CCTTCAGATT TATTAAAACT
 9501 ACCTGGTAGC TATAGAAAGA TACATAGCTA TTAAAAGGTA CATAATCTAG
 9551 CTTAGAACTT TGAGGCTAGA AAGTATATCC CTTTATATAA GAGAGAGAAA
 9601 AAGAATTCTA TCAAATGACC ATTCTGAAGA TAGAACATAT CTATCTGTAG
 9651 ACAATACATT TCATGGCATT AGACATATAA AAGGTGTGTG CTATTTTTTT
 9701 TAATGGTTAG AATTTTTGTA AAATCTGATT CTTAATATTC TTAGTTACTG
 9751 AATCAAATGG ATGGATTTGA TACTCTGCAT AGAGTTAAAA TGATCATGGC
 9801 TACAAACAGA CCAGATACAC TGGATCCTGC TTTGCTGCGT CCAGGAAGAT
 9851 TAGATAGAAA AATACGTGAG TTAAGATTCT TTACCTACTG TCCATTTCCC
 9901 TTTGTGCCCA TTTCTTTTTC CATACTTCAC TTCACCTTCC ACTGTATTTT
 9951 AAAAAAGATA AAACTGGACT ATAAAATAAT TTTTTATTTT CAGATATTGA
10001 TTTGCCAAAT GAACAAGCAA GATTAGACAT ACTGAAAATC CATGCAGGTC
10051 CCATTACAAA GCATGGTGAA ATAGGTAAGG AAGTCATCTA TTTTATATGT
10101 ATTTACATTT GGTAAATGAA GAAAAATACT TTTAGAAATT ACTGATAGTT
10151 TCCTAAATCT GGTTTTAAAT TCAGCAAATG TGGTGGTTTT AAATTCAGCA
10201 AATAGTTATT GAGCATCTAC TATAAGCTAG GAACCATTGT AAGTGTTTTG
10251 TAAGGGCTGA CAATATAGCA AGGAACAAAA CAGACAAATT TCTGCCATTA
10301 GAGAACTTAT ATTCTTGTTA GGAAAAAACA GATAAAGTTA GTAAAACAAA
10351 GTATAATAGA TGATGATAAG TGCTATGGAG AAAAATAAAG CAAGAAAGTG
10401 GGGGGCGGGC ATGGTGGCTC ACTCCTGTAA TCCTAATGGT TTTGGAGGCC
10451 GAGGCAGAAG GACCGCTTGA GGCCAGGAGT TTGAGGTTGC AGGGAGCTAT
10501 GATCATGTGA CTGCACTCCA GTTGGCAAG ACGCTGTTTC AGGGGAAAAA
10551 AAAAGAAAAG GGGGATAGGA AATTAGGGAA GTGCCAGGAC CAGGCATGAG
10601 GATATGTTTT TAAATGACAG GGAGGATTAG CACAGGGAAG GCCTTACCAA
10651 GAAGGTAATT TATTTTTTAG AGACAGGGTC TCACTCTTGC CCAGGCTGGA
10701 GTGCAATGGT GTGATCCCAG CTCACTGCAA CTTCTGCCTC CCAAGTTCAA
10751 ATGATCCTCA CACCTCAGCC TCCTGATTAG CTGGGACTAC AGGCACACAC
10801 CACCAACCCT GGCTTGTTTT TTTGTAGGGA TGGGGTTTCA CCATGTTGCC
10851 CAGGCTGATC TTGAACTACT GGGCTCAAGC AATCTGCCCA CCTCGGCCAC
10901 CCAAAGTTCT GGGATAACAG GCGTGTGCCA CTGCACCCGG CCTGGTTGTT
10951 TGTTTGTTTG TTTTTTAAAT TGATTCCTGT TAAATGCTGA CAATAGGTCA
11001 GATAAAGAGT TCTCAGAGTA GACCTTTGGA TTTAACTATA TGGAGGTCAT
11051 TGGTAATCTT GTCAAAAGTA GCTTCTTGGG AGTGGTGGAG GTGAAAGCCT
11101 ATTTCAGATG GGTTTCAGAG AGATTGGGAG GAGAGGCATT GAGTTTAGAC
11151 ATTTCTTTTA AGAGTTCTAC AGAGGGGGCA GAAGAAGTAG AAGGGGAATG
11201 CCGATGAGGA GTTGGCAGAG TTTTCTATAA GATGGAAGAG TTTATGACCC
11251 CCCTGCCCTT TTTTTTTTTT TTTTAATAAT GCTACTGGGA ATGACCTAGG
11301 AGAAAGAGAA ATTGGCAATG TTCTTTCCTT GAAGAGGGAT TGGCCCTATA
11351 TATATGTGTA CTTTTATGAG ACTGGAGGAA AGGCAGAGTA CATAGATGCT
11401 TATGATGACA GGTTCTTAGA TAGTGCAGGA ACTTGTGGAA GTGTTTTTTT
11451 CTGAATGCTT CTGTTTTCTC AGTGAAGTAG AATGCACGTT CAGAATGAAG
11501 ATAGGGAAGT GTTCTTAGAG ATTTGAGGAC AAAGGAGAAG GTATAAAGTC
11551 ATTATCTATG GAAGTGAGGG ATTGGACTAG GGTGCAGGCC AGTAAAACAT
11601 GGCTTGTGAA CCAAATTCTG CCTGCCCTGT GTTTTTGAA ACACACAAAG
11651 TTTTGTTGTA ACCCAAGCAT GCTCATTTAT CTGTTGTCTA TGGCTGCTTT
11701 CCTACTGGAA TAGCTGAGTT GAATAGTTAC AACAGAAACC ATATGGCTTG
11751 CAAAGCATAC AGTATTTACT CTCTGGCCCT TTACATAAAA AGTTTGCTGA
11801 CCTCCAGACT AGGGAAATCT AGTATAATTT CCAGGCAGCC TTAAAAACTC
11851 TTTAGAAGTT AATGGTCCAG AATAATGACA AATAGCTGAT TGTTGAATTT
11901 CACTATCTTC ATTGCCCCTG TTAGAGAGTT TTGAGCTGGA AAGACCGAAC
11951 TGAACAAAGG ATGTCAATGT ATAGGTTTCT TCCACAAATA CTGAGCTCTT
12001 GCTAGATGCC AGATACTGTG CTAGCCTTGG GAATTCTTGC TCTCAGGAAG
12051 CTTACAATGA ACTTAAACCT GATTAAAGAC AATTCATGAA TATATGTGTG
12101 ATTTCAAATA GAGAACGACA TGCCCTATAT TGCCTGACCA AACGGTGCAT
12151 CATCAAAGTT ATTCAAACTG TAGTAGCCTG TGCTGTCTTA CTTCTCTTCC
12201 TATTCTGTAT CAGATCCATT GTTGCTACCC AATCCTATA GCTCTTTGAT
12251 TCATGTCTGT TATGTGGGTG GATGGAGAAC TCACTTATT ACTGCTACCA
12301 TAGATCTGAT ACTTCACCAC TTGAATCTTG CACAGAAACC AGAGAAGCTA
12351 GCTAATGCAT GCTGTAGCAT TTAAAAATTC CATGTGATAC AATTATGTAT
12401 GATTACATTT CAGTTTTGCT ATACTTTATA TTTGGCTTGT ATGATTAAAG
12451 TAAACAAAGT AAATTCCATT GTTATAATTG GTTTTGAGTG TTATAGGTTT
12501 ATTCAAATCC AAGATTTGAT TACAGTTTTG ATAAGAGTCA CAGCTTAACA
```

FIGURE 3, page 4 of 29

| | | | | | |
|---|---|---|---|---|---|
| 12551 | GGTATCTGGA | GTTCACATGT | GCATAGCTAT | TTCACTGTAT | AAAAATAGAT |
| 12601 | TAAGATATTT | TGAGATTTTG | GTGATATTTC | CTGTTTTTAA | AGTTTCAGGG |
| 12651 | GTGTGTCTAA | TTCTTCTTGG | TGCTGGTTTA | TTTAACAGAA | GTCTTAGTTT |
| 12701 | TTGGATATTA | ATATTGTGGA | AAGTTAACAG | AGCTGATGTC | TAGCTGATCA |
| 12751 | AACTCAAAGT | AAGCTCTTCA | GTTTAAATTT | TCGATGTGGG | CATAAATCAA |
| 12801 | GTAAAGGTCT | AATTTTTAAA | ACTAATTTCC | AGTATTTTTT | CTAAACAGAT |
| 12851 | TATGAAGCAA | TTGTGAAGCT | TTCGGATGGC | TTTAATGGAG | CAGATCTGAG |
| 12901 | AAATGTTTGT | ACTGAAGCAG | GTAAGGGTTT | AAAGTACAGT | TTTACTATTG |
| 12951 | ATTTTGATTT | TTAAAATTTG | CTGAAACTGT | TTTGAGTTTA | TCTGAAAGCG |
| 13001 | GAGCATAGAC | TTTGCAAGGA | TTTGGGTTCA | TGCTGTTCTT | TTAGGAATCG |
| 13051 | ATTCCAGGAA | ATAGGAGAAG | CAGGGCAAGT | GAGATGGAAA | GAGGGAAAGC |
| 13101 | TAATATGAGG | GTGCACCATT | GAGGTAGGTG | CTGTAGGAAA | GGGAGGTTAG |
| 13151 | ATCTCAGAGA | AGCATACAGA | ATGCCTTCCA | GGATCACCCA | GCTGAAAGTT |
| 13201 | GGGAGACTAG | AACATTGATT | TACCAGTACT | CATCCCCCAT | TGGATGAGAT |
| 13251 | TTGTCCTTGG | TAGTGTTGAC | TCCTTTGCAC | TTCTACCTGC | CTTAGGGCAG |
| 13301 | AATGTGGAAG | GAGAGGCATG | TAATAGAACA | CTGGCCCCCT | AAAGTAAGTC |
| 13351 | TGAGGTGCTA | CAGAATTGCC | TACCACACCT | GTGGCTGGAA | TTAGAATGGG |
| 13401 | CCAGCACCAG | AGGTATCTGC | TGCAAAATGA | ATTGTGTATG | TTGTCTAATA |
| 13451 | CTAGTCTGTG | AGCAGTGTTT | TGAAAGATTG | ATTTATGAAT | TATGTGATCA |
| 13501 | TGCCATTTGT | GTAAATGTA | GTATTTAAAT | ATAATTCTCT | GTGGATTGTG |
| 13551 | TGATACTATT | TTTTTCACTT | CTACATGGTA | TGTAAAAATT | GTGTGATGCT |
| 13601 | ATTTTTATTT | CCAGTACCAA | GTAGCTTTAA | TACCCTACCT | AGAATCATTT |
| 13651 | AGTTTTTGTC | TTCCATACAG | AATCTTTAAA | TAGAAAAAAT | AAACTTCTAC |
| 13701 | ACTATAGTTA | CTGACTTTAT | AGGTTATAGA | TTTTCTTAAG | TATTAGAATA |
| 13751 | TGTGATTTCC | TCTTGCTTTT | CATATCATGT | TTAGCCTTAG | TAAATTCAAC |
| 13801 | ACAGTGTTTA | AAGTGGCTGC | TCAGGGAGGG | CTTCTCAGTA | CAGGTATCTT |
| 13851 | CATGGGTATT | GGGTATGCTG | TGAGTCAGTA | TCTGCATCAG | ATATGCAGGT |
| 13901 | CAGATACTTC | TGTTCACGTC | TAGAAATGCT | GTCAATGCAA | ATTAGGGTAA |
| 13951 | ATCATGCTCA | CAGAGCGTTA | TCAATAAACT | AAACTATTTA | GAGGTAAACT |
| 14001 | GTCATATAGC | TTGAACAAGT | TAGAGTAATT | TATGACATTC | TCTTTCCAAA |
| 14051 | ATGTAAACCA | GACCAAATTA | TTATCAGAAG | ATTGCTTTGG | TTAGATTGTA |
| 14101 | ATCCAAATGC | AAGCTGTGCA | GTGAACCTAA | AGGCTGTTGC | TATCAAAATA |
| 14151 | TACGCTTTTT | TTCCTTACAT | ATTCTTACAA | ATTTACCTTT | AGTTATTGCA |
| 14201 | AATGAGCTAT | AACTTCTGTG | TGGATTAAAA | TTGTAGTTCT | TTTTTAACTA |
| 14251 | GGTGGGACAT | TCACATCTGG | AAACATACTG | AAATTTTTAT | CTTCTTTTTA |
| 14301 | GACTTGAAGG | CTTTTTTGTT | AACATTTTC | GTAAGTTAAA | ATACACTTGA |
| 14351 | TTCAACTACA | GTTGCCCTTC | CTGTTCAGGT | CCTGACATTA | TCTCTTTTGG |
| 14401 | ATTATAATAC | ATCTCTATTT | TATTTTTTCT | TTTGAGACGG | AGTCTCACTC |
| 14451 | TGGCCCAGGC | TGGAGTGCAG | TGGCATGATC | ACTGCTCCCT | GTAGCCCAGA |
| 14501 | CCTGATCATT | TCTCCTTTAT | CTCCCAGTAG | CTGGGACTAT | AGGCGTGCGC |
| 14551 | CACCACACCC | AGCTAATTTT | TGTATTTTTT | GTAGAGACGG | GTTTCACCAT |
| 14601 | GTTGTCCAGG | CTGGTCTCAA | ATTCCTGGGC | CCGAGTAATC | CACCCACCTG |
| 14651 | GGCCTCCCAA | AATGCTGGGA | TTACAGGCAC | AAGCTACCAG | GCCTGGCCAG |
| 14701 | GCATCTCTTG | TGCAGATTTA | CTTATTCACT | AAAGTGATTT | GGAAAATAGC |
| 14751 | CATGTGTGCA | AGGTTTACAA | AAATAACTTA | CCTAGTTTCA | CTGTAGCTTT |
| 14801 | CTAAACAAGT | TTTGAAACTT | TGTTATTTTT | TAAAAATCAG | TCATTTCCAT |
| 14851 | TCACCCGGTT | TCTAGGACAA | CATAGATTGT | TTCCTTATGT | AGAAATCTAG |
| 14901 | AAAGGAAGTA | ATCCTTGAAA | TCTTCTATAT | TAACTCCCTC | ATTTTATGTA |
| 14951 | AGTGAAAATT | CAATACAGGC | AGATCCTCAG | TGGAAATTTT | AGAATTCATT |
| 15001 | TAATTAGTAG | ATAGCAATAA | ACTTACCTGC | TTTAGTTTAT | CATGAGTTAG |
| 15051 | GATTATCTCA | AAATCTGGGA | CCCATATCCA | TAACACAACT | AATGTTAAA |
| 15101 | AAACTGCATA | CAAGGAAACT | TTTACCCCTT | TGTCAAATAC | TGTTGAGAA |
| 15151 | GGTACTTGTC | AAAAAGTTGA | AGGAAAAAAT | TGAGTTGTGA | TACTCAAATA |
| 15201 | TGAATCAAAT | AAAAATACCA | ATTTGTACAT | AAATTAGGTA | AATTTTAACA |
| 15251 | CATGAATAAT | GACTCCGAGT | TTTGCTAAAA | CCCGCTGTTG | GCTTTCTATA |
| 15301 | TGATTCCCTA | TTCTCAACGT | TTTTGATTAT | TAACAAAGAA | TGGCTATCAA |
| 15351 | ACTTACTCAA | GATTTTTTTT | CCCCCATAAA | TGTGTGCCTT | CCAGCAAATT |
| 15401 | GCTTCCTGTC | AAGTTAAGTT | ACGCTTAAAA | TGTGTATGTG | TTGGTAGTTT |
| 15451 | TGATTGCTTC | GGTTTTTTAT | GCTTGTTTTT | ATTAAGAGCT | ACAATCAGAT |
| 15501 | ACAGGGACCA | TTTAAGCCTG | ATTTTATTTT | ATTTTATTTT | TTTGAGACAG |
| 15551 | AGCCTCACTC | TGTCACCCAG | ACTGGAGTGC | AGTGGTGCGA | TCTTGGCTCA |
| 15601 | CTGCAACCTC | TGCCTCCCGG | GTTCAAGCGA | TTCTCCTGCC | TCAGCCTCCC |
| 15651 | AAGTAGCTGG | GGTTACAGAT | GCCCACTACT | ACGCCCAGCT | AATTTTTGTG |

```
15701  TTTTTAGTAG AAACGGGGTT TTACCATGTT GGCTAGGCTG GTCTCGAACT
15751  CCCGACCCCA GGTAATCCGT CCACCTTGGC CTCCCAAAGT GTTGGGATTA
15801  CAGGTGTGAG CCACCGTGCC CAGCCTTGAA CCGGATGTTA AATATTCATA
15851  TAATGGTCAT ACCTGTTTTT GTTTTAGAAC ATAATCACAA CACCGCTATG
15901  GATTTTTTTT TTTTTTTTTT TTTTGAGATG GGGTCTCGCT CTGTTGCCAG
15951  GCTGGAGTGC AGTGCCACTA TCTCAGCTCA CTGCAACCTC CGCCTCCTGG
16001  GTTCAAGCCA TTCTCCTGCC TTAGCCTCCC GAGTAGCTGG GACTACAGGC
16051  GCGCGCCACC ATGCCCAGCT AATTTTTTTT TTTTTTTGTA TTTTTAGTAG
16101  AGATGGGGTT TCACCGTGTT GGCCAGGATG GTCTTAATCT CTTGACATTG
16151  CAATCTGCCC ATCTTGGCCT CCTAAAGTGT TGGGATTACA GGCGTGAGCC
16201  ACCGCACCCG GCCTGTGGAT TTTAATTGAA AAAAGATAGT GGTTTTTAGC
16251  AAATTACAAC TACTGGCTCA GAAGTAATAA ATCTAAGCTT CACATTTATT
16301  CCATAGAATT ATATTGTTTT TCTTATAATG AACATATAAT TCATATGTGA
16351  TATATAGCAG TCATGTTGTT TTATTCTCTA CAGGTATGTT CGCAATTCGT
16401  GCTGATCATG ATTTTGTAGT ACAGGAAGAC TTCATGAAAG CAGTCAGAAA
16451  AGTGGCTGAT TCTAAGAAGC TGGAGTCTAA ATTGGACTAC AAACCTGTGT
16501  AATTTACTGT AAGATTTTTG ATGGCTGCAT GACAGATGTT GGCTTATTGT
16551  AAAAATAAAG TTAAGAAAA TAATGTATGT ATTGGCAATG ATGTCATTAA
16601  AAGTATATGA ATAAAAATAT GAGTAACATC ATAAAAATTA GTAATTCAAC
16651  TTTTAAGATA CAGAAGAAAT TTGTATGTTT GTTAAAGTTG CATTTATTGC
16701  AGCAAGTTAC AAAGGGAAAG TGTTGAAGCT TTTCATATTT GCTGCGTGAG
16751  CATTTTGTAA AATATTGAAA GTGGTTTGAG ATAGTGGTAT AAGAAAGCAT
16801  TTCTTATGAC TTATTTTGTA TCATTTGTTT TCCTCATCTA AAAAGTTGAA
16851  TAAAATCTGT TTGATTCAGT TCTCCTACAT ATATATTCTT GTCTTTTCTG
16901  AGTATATTTA CTGTGGTCCT TTAGGTTCTT TAGCAAGTAA ACTATTTGAT
16951  AACCCAGATG GATTGTGGAT TTTTGAATAT TATTTTAAAA TAGTACACAT
17001  ACTTAATGTT CATAAGATCA TCTTCTTAAA TAAAACATGG ATGTGTGGGT
17051  ATGTCTGTAC TCCTCCTTTC AGAAAGTGTT TACATATTCT TCATCTACTG
17101  TGATTAAGCT CATTGTTGGT TAATTGAAAA TATACATGCA CATCCATAAC
17151  TTTTTAAAGA GTATGATTCA ACGTAATATT TGCTAATATG TGACTGGGTT
17201  TTCTTGGTTT ATGTAAGACG ATAGGTCCCT GTTGAGGATG TGAAGGTCTG
17251  GACCCTCTTC CAGGAAAAAT TCTAACATAC AATTTTGCGT ATACTATAAT
17301  TTCAGGAAAT TTATTGTTTC CCAAGCTCAT CCAAGGATTC TTTAGGTATG
17351  TATGGATACC TGGCTAAGAG TGTATGATGT AGGGGATGTA GGAGTGTCAG
17401  AAATGTTCAA AACATGATTT CTGTTACCTA TACATGATTC TTATATCATC
17451  TGGCAATAAA AGCTATAACA AAGTACACAA AGGAATCATC ATTGGGCATC
17501  AATAATTATT AAAGATGCTG GTGAAAAGAA AAGACAACTT CAGTTTCATA
17551  AACACTAAAG AACCAAAAAT ACATGACCTA GCTAATTATA CAATAATTCT
17601  TCAAATTAAA AACTTCCTAG CAGGATATTA TGTGCCTTTT TATAATTTTT
17651  AGAAAGATGA ACAGTTAAAA TAGAAAATGG AGTGGTCAAG TTAGCCATCT
17701  CATACTCAAA ATTATTGTAC AGTTCTATTT CTATGTGTTG GCAGTGCATT
17751  TTATGTGACA AAAAGTAGAA TGTAGGGGGA GGTTTAAGTC AAATATCTAT
17801  GTGATCTTTT CACTTATAAT TTGCATTTAG TTAAGGAGTG ACTATCTTGC
17851  CTTTTACCTT TGTGCTGGCG GTGGTTTTTT AAAGAATCAA TTTGGTGTAC
17901  AAATCCTTTC TTTCTTTTTT TATTTTTGAT TTTTTTTGAG ATGGAGTTTC
17951  GCTCTTGTTG CCCAGGCTAT AGTGCCATTG CACTATCTCA GCTCATTGCA
18001  ACCTCCGCCT CCCGGATTTA AGCGGTTCTC CTGCCTCAGC CTTCTAAGTA
18051  GCTGCGATTA CTGGCATGCG CCACCACACC CAGCTAATTT TTGTATTTTT
18101  AGTAGAGACG GGGTTTTTCC ATGTTGGTCA GGCTGGTCTC AAACTCCCGA
18151  CCTCAGGTGA TCCACACGCC TCAGCCGCCC AAAGTGCTGG GATTACAGGC
18201  GTGAGCCTCC GCGCCCGGCC CAAATCTTTT CACCATGGGT TTACAGGCAT
18251  AACGCCACCA CACCCAGGGA ATTTTAAAAT TGTTTTTTAG AGAGGGGGT
18301  CTTACTATTT TGCTCAGGCT GGCAAACTCC TTTTAAAGA TATTGAAAGC
18351  CATCTGGTTT ATTATTTTTA TTTCAAAATA TAATAATGGA AGAAATTTTA
18401  CAGTATTATA TACAATTTAC TGAGTCAGCT ATCAGTTCCT TTTTCTGATT
18451  TTTTTCTAGT TGCCATTCTT GATATTTTCT AGGTAATCTA AACTGAGTTG
18501  TATTTTCAAG TACTCTTCAA ATACTTTAAA AAATTTTAAA TTGAGCCGTT
18551  TAATTCTTTG CTTAAAGGTG ATGGGTATTT TATTTTCTGT ATGGCACCAC
18601  GTGATTTTAA ATTGAACTCT TCATTTATTA GTCATTTGGT TATAAACTCA
18651  GCATAGATTG CGCAGAATTT TGAGAGGGGA GAAACTATAG CTTTCCTTTC
18701  GGATGCCACT GGTGGGTAGC CTGTTTTGCC TGTTTGTTCT TATGTTAAAG
18751  AAGGGCTCTA CGTCCTGTCT GGAAAGGGCG GAGCTGGCTC GGACCGCCCC
18801  ACTGCCTTTC CCAGGACCTT CACTCGTCCT GTCCCACCGC AGCCCCGCCT
```

```
18851  CCTCCACGCC GGGTGAGCTG TGGCCTAGCA GCATCCGAGG CTCCGCCCCC
18901  CCCACCCCCC AGCGTCTGCG CTCTAGCGAA GGGGCGGAGC AGGGCGGTGG
18951  CGCGCTGACA CCTGGCGGCG GCGGAGGGCG GGCAGAAGGC GAGCGTGGGC
19001  TGGGATTGGC TGAGGCGACG CGGGTGGAGG GGGCGGGAAG GAGGCGGGGA
19051  GACGGGTTGT CGGGCTGGTT CCTGTGCTGG ATCCTGGGCG GCCTGAGGGG
19101  TACGGAGACT CTGGGGGAGG GAGACGGCAG CGGCATGGCG GCCGGGTGTA
19151  AGACGCCCGA CCCTCCTCTT CCCTGTCTTC GCCGCCGCCG CTGCTGGAGT
19201  CACTGGGACC CTCTAGTCTG CGTGTGTTAG TTGTAATCCC GCCGCCCTCC
19251  TGTCAGCCCT CCGCTCCGCC GGCCCTCCTT CCTTCCGCCG CCGCAGCCAG
19301  CCCGAGGGTC GGCCGGCTGT GTAACACTCT CCCACCCCAC CCACCAGCCC
19351  GCGGGCCAGC ACCATGGAGG ACGTGAAGCT GGAGTTCCCT TCCCTTCCAC
19401  AGTGCAAGGA AGACGCCGAG GTGAGTCGCT CCCGTGGCTG CCACGCACAG
19451  GCCTCTCCCT GTGGCTCCGG CCGAGGGGCG ACCCCAGTCC CCAACCGTCT
19501  TAGCCGCCAC CTGTACGGGC GCCCTGCCTC CTAAGGGCGT CCCGGGACCT
19551  CTGAAGCCGA GCGGTCGGCT CCAATCCCCA CTGAGTTGCT CGTCCTCTCC
19601  AGACCCCGCG GAGGGCAGC GTCTGGTGTA CTTACATTTG AGAAGAGGAA
19651  AAGCAATCCC TTAGTCCCTA GGCTTGGCAT CCAGGACTGA CCTGGAGTAA
19701  GGTTCCTCTT TTATTGTCAA AGTAACAAGA GAGCGAAGTT GGTTTAGTCT
19751  CCTTTTGAGG AATATCTGTG GTGTAAACGA TTCACTTGTG GACACATGG
19801  CCCCACATGT GAAATAGACT CGGCGCCTGA AGTTTGGAAG CGCGCCTTCG
19851  AAAAGTTTCC CAAAGTTTTT TGTTTGTTTT TGGACAAAGC TATGACCCGC
19901  ACAACAAAGT GTCTCAAAGC TAGCTCATCT TAATCTGAGA ACTCTTAATC
19951  AGAAATCTTG ACCTTTGGAG GAAAATTAAT ATTGAAAGTA AAATACTATA
20001  TACCTTTTCT CCTGGTTTCT AATTTGTGGC TATTTTTACT CCACCTTAGA
20051  TCCCTGCCTG CTGTTTCTAC TCGGATTTTT TTTCATCTGT TGCTAGTTTA
20101  ACATTTTACG GCATTGCAGA CTACTAAATT AGAATTTTCT GGAGGCTAAA
20151  TTAACAAGAC GAAGATACTC AGCTATACTT TAGTAGGATT AAGAAAGAAA
20201  ATCTAACATC GCTAGTTAAA AATACCTTTA AAGTAGTTGG GAAAAATAAA
20251  GCCCTATTTT TAGGAGACCA TTCAATTTAT TCCGAATATT TATTCTATTG
20301  AATATCTTCA TTGGAGGTTC ACTTTTTTTT TTTTTTTTTT TTTGAGACGG
20351  AGTCTTGCTC TGTCGCCAGG CTGGAGTGCA ATGTGGCGCG ATCTCGGCTC
20401  ACTGCAACCT CCGCCTTCCG GGTTCAAGCG ATTCTCCTGC CTCAGCCTCC
20451  TGAGTAGCTG GAACTACAGG CGCGCACCAC CACGCCCAGC TAATTTTTGT
20501  GTTTTTAGGG GAGACGGGTT TCACCATTTT GGCCAGGGTG GTCTCGATCT
20551  CCTGACCTTG TGATCCGCCC GACTCGGCCT CCCAAAGTGC TGAAATTGCA
20601  GGTATGAGCC ACCGCGCCCG GCCTAGGTTC ACATTTTGT TTGGAGGGCT
20651  CTCTTGTGGT ATTGATGCTT GACAATTACA TTTGTTTTAA GAGTAGAGAC
20701  TTTGTTTGTG ACTATCACTG TTGCAAAATG TAGTGCAGTG GTGTGATCTC
20751  GGTTCACTGC AGTCTCGAAC TCCCATGCTC AAGCCATCCT TTCACCTCAG
20801  CCTCTGGAGT AGCTGGGACC ATGCCGGGCT AATTTTCTT TTTTTTTTT
20851  TTGTAGCGAT GGGTTTTTTC TCCAGGCTGG TCTCGAACTC TTGGCCTCAA
20901  GATCCTCCCG CCTTGTCCTC CGAAAGTGTT GGGATTACAG GTGTGAGCCA
20951  CTGCACCTGG CCCAAGAATA TACTCATGGT TTTTTGTTT TTTTTTTTT
21001  TTTGACACAG AGTTTCACTC TTGTTGCCCC AGGCTGGAGT GCAGTGGCGC
21051  TGTCTCAGCC CACCGCAGCC TCTGCCTCGG GTCCCGGTTC AAACAGTTCT
21101  CCTGCCTAAG CCTCCTGAGT AGCTGGGGAT TACAGGCGCG CACCGCCAGG
21151  CCCAGCTTTT TTTTTTTTT TTTTTTGAGA CAGAGTCTCA CTCTGTCGCC
21201  CAGGCTGGAA TGATCTTGCA GTGGTGCGAT CTGGGCTCAC TGCAAGCTCT
21251  GCCTCCCGTG TTCACGCCAT TCTCCCGCCT CAGCCTCCCG AGTAGCTGGG
21301  ACTGCAGGCA CCCGCTACCA CACCGGGCTA ATTTTTTGT ATTTTTAGTA
21351  GAGACGGGGT TTCACCATAT TGGCCAGGAT GGTCTCAAAC TCCTGACCTT
21401  GTGATCCGCC TGGCTTGGCC TCCCAAAGTG CAGGGATTAC AGGCGTGAGC
21451  TACCGCGCCC GGCCAATATA CTCTTAGAAA ACAGGAGGTC ATATTTAGGC
21501  TAGTTATAAA AATGAATTTA TACTTAACAT ACAATAATGT GAATGAAGAG
21551  TATGCTTTTA TTTATTTATT TATTTTTTTG AGACGGAGTT TCACTCTTGT
21601  TGCCCAGGCT GGAATGCAGT GGCGCGATCT CCGCTCACTG CAACCTCCGC
21651  CTCCCACGTT CAAAAGATTC TCCTGCCTCA GCCGCCTGAG TAGCTGGGAT
21701  TACAGGCGCC CGCCACCACT CCCGTCTAAT TTTTGTACTT TTAGTAGAGA
21751  CGGGGTTTCA CCATGTTGGC CCTGCTGGTC TGGAACGCCA GACCTCAAGT
21801  GATCCGCCTG CCTCGGCCTC CCAAAGTGCT GGGATTACAG GCTTGAGCCA
21851  CCGCGAAGGA GTATGCTTTC ATATCCTCAA AATGATTCAG TAATTTCAGC
21901  ACTTAACTGC AAGCAACCTT ACAAATAATG TAGAGGAGTC CCACATTCCA
21951  GGTGAAGAAA TTGTACCTTA CTGAAAATAA GTGATGTGCC AAATTAACAA
```

```
22001  CACAGTAGCA CAAGACACAG AAGGACCTCG GCCTCCTAAT TCATTGTTCT
22051  TTTTAATACA CTTCAATTCT TCCCTGCCCT AATCTTAAAA ATTCTAGTTT
22101  AAAATTTTCC CGGACTTTGC ATTTAATCTG TTACTGTGTA TATCATTATG
22151  TATGCCTTAT TCCTGCAAAA CTGATAAATT CTTGCTGGGA ATATATACCT
22201  GTCTTTTCTG TGTGGGACTT GAAAACACAC TCTTTTTTTT ATGCTACCAG
22251  ATGTGTGGGG GTTTTTCCAT ACCAAGCAGT TTTCCAGCAG GCATGAACTG
22301  AATGTCCCAT AATTCAATTC TGACACATAT GTACCTGAAG TTAGTCAGAT
22351  CCCACAGGTT AATGGGCTCA GTCCCGCAAG GCTGCCCCCA ACCTCAGATG
22401  GTAATCACAA GTAGTAGGTT GTCACCTATA CACTCCTGAC TGACTGTAAA
22451  TCAGGGTTCC CGTTACTCCC TCCTTGGTTC AGTTAACTTG CTAGAGTGAC
22501  TTACAGGACT CAGGGAAGTA CATTTACGGG TTTATTATAA AGGATACTAC
22551  AAAAGATCAG TGAACAGCCA GTAGGAAGAG ATGAATAGGG CAAGGTATGG
22601  GGGAAGGGGC ACACCACCAT CCCAGTGTCA CCAGTAGAGT CATGATTGCA
22651  AGCTGTCCAG GTTCTTGGCG TTTTGAACAA AGAATTGGAC AAAACTCCAA
22701  GCAAAGAAAG AATGAAGCAA CAAAAGAACA AAAGCAGGGA TTTATTGAAA
22751  ACAAAAGTAC ACTCCACAGT GTGGGAGCTG CCCTAGCAGC ACTCCCCCCC
22801  GACCCCCGCT GCTTTACCGA ATCTTCTTGG GTCCAAATAC CCCCTAGAAG
22851  TTTCCCATTG GCCATTCCAT GCTCACCTCA TGTAAATGAA GAGGTGGCTT
22901  GCAATTGGTC TGATTGGTTG CCAGACCCAC CCCCACATCA GTCCGCTTGG
22951  TTGTGGACAG CGACCATTCA GTGGCTAGAG TGAAGTTACA AAGTTGCAAA
23001  CGAAGATTCC ACCCGCAGTC AGTCTGATTT GTTGAGGACA GCCAATTTCC
23051  CGTCTACTGT GCAGAAAAGG TAGGTGGTTT GCAACGGGAG TAGCCTCTGG
23101  TCCTTTTGTT ACTTAGGCGT GGAAAGTTAG GGTTTTCCCT TCAAGTTAGT
23151  TCTGGGAAGT CGGGGTGAAA CAGCCTTAGA TTCCCTGCCT CCAGACCCTA
23201  TTCACCTGCC TCACTAGCAC CTCCAGTGTT TTCATCCAGA AGCTCAACAA
23251  ATCTTATTCA ACGGTTTTTA TAGAACTTCA TCTCCATCCC CTCCCATAGA
23301  GGTGTGTGTG TGTGTGAGGC TGAGAGTTCA ACCCTCTTGT CACATGGTCT
23351  TTCTGGTGAC TGGCCCCACC CTAAATCACT TCATTAGCAT AATCAGGTTT
23401  GATCAAAAAT AGTGGCTCAT AAATAACCAA AGACACTCCT ATTAGAAAAT
23451  TCCAAGAGTT TTAGGAGGAC TGTGACAGGA ACTGGAGAGA AAGACCATGT
23501  ATTTCATATT ATATCACAGG GACAGAGGTA ATGGTTAAAG CTAGTGGATA
23551  ATGATGCAAG TATTGTCTGC TGAAAGCCAA TTCGTTCCGT ATTTCTTAAT
23601  ATTGCATGTT TGGTATCTTT TGGTTGCAAG CAACAAAAAC GAATTTAAGA
23651  AAAAGAAGAA GTAATTAAAT CCGGCCGGGC GCGGTGGCTC ACGCCTGTAA
23701  TCCCAGCACT GTGGGAGGCC GAGGCGGACG GATCACGAGG TCAGGAGATC
23751  AAGACCATCC TGGCTAACAC GGTAAAACCC CGTCTCTACT AAAAAAAAA
23801  TTAGCTAGGT ATGGTGGCGG GCGCCTGTAG TCCCAGCTAC TTGGGAGGCT
23851  GAGGCAGGAG AATGGCATGA ACCCGGGAGG CGGAGCTTGC AGTGAGCCGA
23901  GATCTAGCCA CTGCACTCCA GCCTGGGAGA CAGAGCGAGA CTCCATCTCA
23951  AAAAAAAAAA AAGTAATTAA ATCCAGAAGG GTAGTGGTGC AGCTAGTTTC
24001  AAGGATTTGA CCAAACCCAG GTATTATAAA GCATCAGAAC TGCCTTTGTC
24051  TCTCATGAGT TCTTATCTCT ACTTTCTCTC AGAGTCTCTG CTTTCTCTCT
24101  GGCTTCTCCA AGATGTGAAG CTTGGCCATC TGGGGTCACA CCTTTATGAG
24151  CTTGGTTATT GAGGAATAAA ACTGAACACT TCCAGCTTCT GTGTTTGAAA
24201  TCTAGAGGAA TTGCCCAATT TAATTCATGT TCCCACACTT TGGATCAGTC
24251  ACTGTAGCCA GGAAAGGGCA GATACAATGA GGGGCCCCAT CTAGGTCATA
24301  TCCCTAATTC CTTGGCTAGA GGAGTGAAGT TTATTGTTGG TAGCCCTCCC
24351  ACCAAAACCA TAGGAACATT TCCACAGGTA GAGGGTACTT TCTGGGCTGA
24401  TAAAACTATA CATAGGGCC ACATAAATAA ACTATTAAAT AGGAGCATAT
24451  AGTTATTCAT AATAAACTGA CTAATAAGCA CTGTTAATTT TCTAATCTCC
24501  AGTGAGATAA TGTAAAGTGT CAAATGGTCT TAAGTAGTTA GAGTGATCAG
24551  CCAGCATTGT TTCTTTGACA CAGGGAGCAC TACCTGGAAA TCCAAATTAC
24601  AGACCAAATT TAATAAAAAC GGAATTCAAG CAGAGAGTTC AGGGAATGCT
24651  TTTAATGTTA ATGTGATCAA GCTATGATAG GTTGATGATT CTGTCACCTC
24701  TACAAGAATA TTACTTTCAC GTTTCTTGAA ATATTGGTAT TCTTTGTATA
24751  GGACAGTGCT AACAAAAATT TAGATCAGTC AGTTTGTGAA AAGATTGTTA
24801  CTTTTTTTGT TTAAAACTTT TTCATGAATT TCCATTGTTT TGAAGATGAA
24851  ATTTAAACCC TTGACATTAT TTCCAGGGTC CTGTATGGTC TGACATCTGC
24901  ATACCTCTCT AACCTCATTA TGAGCTACTC TTCTTGCTCC TTTCTCTGTA
24951  AGCCCTAGCC ATATTTATCT TCTCTCAGTT CCTGGAATGC TTTAATTTCC
25001  ACCCCCCGCC TTCAGAGCCT TTATGTTTGC TATTTTCCCC TGCCTTGGCT
25051  GCCAGCACCT TCCTTACCCT CACCTAATTA ACTGCTTACC CTTGGGTTAG
25101  ATCCCACTTT AGGCAACATT TCTTCAGAGA AGCTTTTCCT GTTTGCCAGT
```

FIGURE 3, page 8 of 29

```
25151  TTCTCTAACT CCTTTCCTCA TCCTCTAGAC TGGTTCAATT CCCCAGCTAC
25201  TATGGCACTT GGTACTTTAA TACTTACCTT TGTAACATTT AACAATTTTT
25251  GGTCATTGTC TATTTTCCAT TTAGACTGAA CCTTTCATAA GAGAGCTTAG
25301  ATATTAGGAA GAAGGAGTAG CTGATAGTAC CAATTTTTAA GCAAATTGGT
25351  TGTAGCTGGG GCTATTGGTT TTATAATTTA AAAGTTAATG TTTTATCTTC
25401  TCTTCTGACA GAAAGTGAAA TATTTATTTC CATTGCAGTT TAGCAACTTT
25451  CCATGTTTCC CTTTCCATTT TTCTTGTGAA TCCCGTAGTA CAGGATCAAA
25501  GATAGGAATT ATTTAACATA CATGGCTGAG GATTCCTTTT CTAGCTCCTT
25551  TATTTAGAAT GGTGCTTTTT AACCCTTACT CTAGAGTAAG GAATTTTTTA
25601  AAAATACTGA TGCCTGGACC CTACCAGCAC CTATTGTAGT TTAATTTATC
25651  TGAATGAAGC TAGATGATTC TAATGTTCAG TCAGGTTTAA AAATTGCTGG
25701  TTTAGAAAAT ATCTTGAGTA CTCTTCTGCC CCTCCAGTCC CTGCCCACCT
25751  TCTCTTTTTA TTTGAGTGAA ACATTTTCTT TTCTCCTTTG ATTTAAGCAA
25801  AGCTCAAGCT TGGTGTGGGA ATGAAAGGAA AAGGACTTTG GAGGGATTTA
25851  CCTATTTTTT CTAGGAGAGA AAGTGCAATA CTAACTTTTC TGTTTTGTGG
25901  AATGTCCCAG TGCAAGTCTA GTATTCTGAT GTTTTTTTTC TTCCCCAAAC
25951  TGTTGCCCCC CACCTCCAGC CTATGTACAA TTTGTGTTTT ATTTTAGTAT
26001  TGTGTATATA GGATTCAGCA CTATCCTCAA ATGTATGAAC ATATCCCCTG
26051  TGGATAAGGG GGGACTACTG TATTTGTAAA AGTTCATATT TCATATTTCA
26101  ATGCATATAA GAATTATTTT ATCTAATGGT TACAGTCTAT ATCCTTCATT
26151  GATGTGTTTA TTTGAGGGTC TTTGAACATT TTTGTAACTT TTCTCTATCC
26201  AAATGCAGTT TTATAGATCA TTTTTATGGA AAGGAAGGAG ATAATTCGGA
26251  AGGATGTTTT AACATGTGGT ACTTTCTACC TCATGTTGAT CGAAAGATTT
26301  TCACTTGTGA ATTAATTTGT CTCAGAATCA TGGTGTTTCA CAATAGAGGG
26351  TTATTTTGGT TTATCTGGCT TGCCTTGGTT TGGTTAATGT GGTTGAACTG
26401  CTTGGCTACT CATAAAGTTT GGGAAATTGA TTTCTACTAA TTAATTACAA
26451  TAGTAACTTA AAATAGATCA TTGCTGGTGA TATGGAGATG CCTCCATTAA
26501  TACCACGGTT TCTAAAATGA TAGATTTCAG GAGTAGTGTG AGCAGGCTGA
26551  GATTAAGAAT TAAGTGTGAT AGTGGCAAGA CTTGGTTATT AGACGTGTGT
26601  TCAGACGGAT GTGTGGTAGA AGAAGACTAT GAGCATTCAG ACTTAAAATC
26651  TTGGTTAGTA AGATCCATAG ACAGGCAGGG TTTTTTTGTT TGTTTGTTTG
26701  TTTTAACAGG TTGGAGTGCA GTGGCAGGAT CTCAACTCAC TGCAAGCTCC
26751  GCCTCCCGGG TTCACGCCAT TCTCCTGCCT CAGCCTCCCG AGTAGCTGGG
26801  ACTACAGGCG CCCGCCACCA TGCCCGGCTA ATTTTTTGTA TTTTTGGTAG
26851  AGACGGGGTG TCAACCATGT TAGCCAGGAT GGTCTCGATC TCCTGACCCT
26901  GTGATCCACC CTCCTTGGCC TCCCAAAGTG CTGGGATTAC AGGCGTGAGC
26951  CACTGTGCCC GGCCAACAGG CAGGTTTAAG GTTTGTTCTG TAGGTGGTAA
27001  TCTGGGTTAG GGCAGCAAAG AAGGTGGATT CTGAGATCAG CATCTGATGA
27051  TAACACCAGG AATAGTTCCA AATGAACTTT TCTGTGAGAG AAAGCTTTCT
27101  AGGTTTCAAA GGATCCATAC CTATTGCAGT AATTACTAAT GTTCTCTGAA
27151  GAAGGCTTCT TATCTGTCCT GTGACTAGGA ATAATTTTTC ATTCCCTCCT
27201  ACTATACAAC TTGCTTTTCC CTCTTATAAT ATCTTCCATA TATATATATA
27251  TCTCAAGAGA GTCTTTCATG TTGTATTACA TATAACCTTA TGGAAAGCTC
27301  AAAAGTTCTT TGAAGCCTCT TGTTTTGCTA AAAGGTTCAG GTAAATTTTG
27351  CATTCTATCC CATATGTGCC TGTTTGTTTT AATATAAAAA TTGTTTAAAT
27401  TAGTAACCAG TGAAAATACT GTTTCTCCCT AAAGAATTTT TTTGATAAAA
27451  TTGATACTTC AGTGGCTTTG AGTGTCTTTT GGCATATTGC CAAATGAAGG
27501  TGTTGAGGAA ATGCCACTCC AAAATATGAC ACCTTGATAT ATTGATTACT
27551  TTAAGTTGGA AACACTTGCA AAGTAGCAAA TGCAAAGAAA CACTTTCTCT
27601  GAACTCCTGT TACCTACCTA AGGACAGATC CTCCAAAAGA AGCTCAATTT
27651  GCTCCTAGGG AGTTTGATCA ACCAGGGAAG ATTGTCTCTT ATCACTGGAG
27701  AGGAGAGTAA AAGTCAGCAC CACACCCAGA CAAACTGACA CAAAGTATCA
27751  TCTATTATTA TTCTAAGGGC CCATTTATCT TTCTCCAGAA TTGTTCTTCT
27801  AAATTGCCTG TATACCTCTA CCCCCATGCT ATATAAAGGG TATATAAACT
27851  CCTAAATATC ACTTTTTTTT TTTTTGTATA CACGTTTCTT TCCTGTGATA
27901  CCCCCATGCA CATAATGAAT CTGTATACCT TTTCTCCGTT TAGTTTATTT
27951  CATAGACTGG TTTGAAATAT CACGGATTTT GTTTGTTTTT GGTATACACT
28001  TTTTAAAAAT ATCACTTTTT TTTTTTTGGT ATACACTTTT CTTTCCTGTG
28051  ATACTCCCAT ACACATAATA AATTTGTATA CATTTTCTCC ATTTAGTTTA
28101  TTTCATAGAC TGTTATCGAA TCCTGATGGT AGAGGGAAAG TCTTCCTTGC
28151  CTTACACAAG TATTTCCCAG AATATATTTA CACCATTCCT TGATATGTGT
28201  TGCCCTGTTT TTTTTTCTTT AATTACACAA AATTTAGTGA TTTCACTTTA
28251  GATAAATTCA AAAGTACGCA TTTCTTTAAT TGATTTTCTT CTTTATCACA
```

```
28301 GCTCTGACAA GTTGCTTCAG GAAGATAAGG CTGGCTGTTA GACTACTTGA
28351 GAATCTTTTA AAAAGAAAAA AGTCAATAAC ATTTAGTGCA GTAGATCTCT
28401 GAAATGCATC TATTTTGTGC TTATTCTGTG TCAGGCACTG TGCTTATCAT
28451 TAGGGGTACC ATGACTAAAA AGAGTATTTG GCCTAAAGTC TTTAAAAACT
28501 GTTTTCTTTT TCCTTTCTTT CTTTTTTTTT TTTTTTTTTT TTTCGTTGAG
28551 ATAGGGTCTG TCTCTGTTGC CCAGGCTGGA GTGCAATGGC ACCATGATGA
28601 CTCACTGCAG CCTCGACCTC CCAAGCCCGA GTGATCTTCC TGCCTCAGCC
28651 TCCCAAGTAG CTAGGACCTC AGTCATGCAC CACCACCGCA CCTGGCTAAT
28701 TTTTTAATTT TTGTAGAGAT GAGGTCTCCC TATATTGCCC AGGCTGGTCT
28751 TGAACTCGGG CTCAAGCTAT CCTCCTGCCC CAGCCTTCCA AAGGGCTGGG
28801 ATTGCAGGTG TGAGCTACCA TACCTGGCTA AAAAACTCAT ATATAAAAAG
28851 ATTACCATAA CACATTGGTA AGTTAAAGAA TCTAGGCTGG GCGCGGTGGC
28901 TCATGCCTGT AATCCCAGCA CTTTGAGAGG CCGAGGCAGG TGGATCATGA
28951 GGTCAGGAGT TCAAGACCAA CCTGGCCAAG ATGGTGAAAC CCCATCTCTA
29001 CTAAAAATAC AAAAATTAGC CAGGTTTGGT GGTGGGCGCT TGTAATCCCA
29051 GCTACTCAGG AGGCTGAGGC AGATAATTGC TTGAACCTGG GAAGCGGAGG
29101 TTGCAGTGAG CTGAGATCGT GCCACTGCAT TGCACTCCAG CCTAGGCGAC
29151 AGAGCGAGAC TCCGTCTCAA AAAGAAAAAA AAAGTATCTA GTAAACAATT
29201 ACATTTCCCT CATTGCTGGC TTAGAAATTA CATGCTTTAT TTCTATTCTG
29251 TTAATATCCA TAAATTAGTC ATTATTTTAT GCAGCCAATA TTTGTTTAAT
29301 TGTAACTGTA TGTTTGCCGT AAAGTTCATT CTTACATTGA AAGACTGTAT
29351 AGTATATTGA TTCAGAGAAT GAACTCTGGG TTCAGACTAT CTGGATCCAA
29401 AATCAAGTTA CTTAGGTTCT CTATGACTAA AATAGACAGT GATAGTATCC
29451 CTTCTTCAAA GAACATTTTA ACTTTTTTTC TTTAAAGATA TTTTTCCGAG
29501 CATATATTCT TAATTAACAG TTGTTTTTGT CCTGCCACTA TGAATGAATT
29551 ATTTGTGTCC TCTGGCTTCT GTTCATGCAA TTGAGAAGTC AGTGTCCATC
29601 TGATTGTCCT TCCTTTGTGT GTAATCTGTC TTTTGTCTAG TTGATCTTTT
29651 TTAATAAAGG TAAAATTTAT ATAGTGTAAT GTACAAATAG TAAGTGTGCA
29701 GTTCATTGAG TTTTGATGAA CATACACTAA TCCACCCCAT CAAGATACAA
29751 GAACATTCTA TTAGCATAGA AGGTTACATC TATTTCCAGG CATTTCCTCT
29801 CCCATTCCAC AATAGGAAAC CAGATTTCTA TCAACATAGA TTAGTTTTCC
29851 TTGCTCTTGA ACTTGATACA AATGGAATCA TGCAAATGGA CTCTTTTGTG
29901 TGTGGCTTTC TTCACTGAGC ATAATGTCAA TGAAATTCAT CCATGTTGTT
29951 GTGTTTATGA GTACTTCGTA GACTTTTATC CCTGAGTACT ACTATTCTTT
30001 TGTATGAAGA GACCATAGAC ATTTGAGTTC TTTGAGACTA CAATAAATAA
30051 AGCTGCTATA AATATTCATG TATAAGTCTT TGTGTGGATA TATGTTTTTA
30101 TATATATATA TATATTTTTT TTTTTTTTGG TAAAGCCTAG GAGTGGAATG
30151 GCTAGATATT ATAATAGGGT AGGTGTATGT TTACCATTTC ATTTTACATT
30201 CCCACCAGCA ATGTGTGAGA GTCCCAGTTG CTCCACATCA TCACCAGCAT
30251 TTGGTGTTGT CAATTTTTTT AACTTTAACC ATTCTAATGG TAGGTAATGA
30301 TATCTTTTGA TTTTACTTTT GAGTTTCGTG TGTGTGTGTA TGAGAGATGG
30351 AGTCTCACTC TGTCACCCAG GCTGGAGTGC AGTGGTGCAA TCTCGGCTCA
30401 CTGCAGCTTC CACCTCCCAG ATTCAAGCAA CTCTCCTGCC TCAGCCTCCC
30451 GGGTAGCTGG GACTACAGGC GTGCCACCTC CATGCCTGGC TAATTTTTAT
30501 ATTTTTAGTA GAGACAGGGT TTCACCATGT TGCCCAAGCT GGTAAACTTC
30551 TGAGCTCAAG TGATCCGCCT ACCTCAGTCT CCCAAAGTAC TTGGTAATTT
30601 ACAGGTGTAA GCCACCGCAC CTGGCCTATT CACTGATTTT TAATTTCAAT
30651 TATACTTCTT ATTTCTACAT ATTCTGTGTT TTTAAAAATC AATTTCTTAG
30701 TCTGGTCATA TTTTGATACT CTAATTTCTT TAAATTTTTT ATATTTTTCG
30751 TTATTGCTTA TAATATCTGC AGTTTTGTAA GTGTAACTCA GTTGTTTCTG
30801 CTTCCTGTGG TGGCTCATTT CCTGTTTTTA AATTAGTTTT TGATTGTGAG
30851 CTTGTTGGGA CTTTATCTGT GTGAATTATT TCTGATCTAG GTTTAAGGTG
30901 TGTTTTTCTA GAGAATATGC ATTTGCTTCT TCCAGGAATC CAGGGATGCA
30951 ATCTACCCAG GACCACTTAC ATTAAATTCT CACTTGGCCT CACAAAAGTA
31001 ACTGAATTCT AACCCCAAAC TTGAGTGGAT GCCAGATTGT GGTTAGGAAG
31051 ACCCCACTCC ACCACTACCA ATACCTACCC AGAGCCAAAG CTAGGAAGGA
31101 CAAGAGTACT CACTTCTGTG GGATGAGTTG AGTTTTGTT TTTCTTTCTT
31151 TCCCTAGTTT ATCTTTCACT GAGGATGTTG CCTTTGGGAG TTCTAGCTTT
31201 TTGGTCTTGA TCTGAGTTCG ACTTTGAGCA GATCATAGAC TTTGTCTTAT
31251 GTTTACAAGT ACGTTTCCAC TTAAAATAAG GCCGTAGTGA AGATGTAGAA
31301 CAACTAGAAG TCCCATACAT TGCTGGTGGG AGTGTACAGT GGTTTTACAA
31351 AACTTTTGGC AGTATCTAGT AAAGCCAAAC ATAGGCCTAC CCTGTGTCAA
31401 AAGACAAAAT TACAACAAAT TTAGCTTAAA AATCTAACTC ACTTTTATTA
```

FIGURE 3, page 10 of 29

```
31451  GTGGTTCATG AATCAGGCAG TGTGTCATCA AAAGATTTAG AAAAGGCATT
31501  TCAGTGTGCT GAGCAGAGGA AGTTGAATTT ATAGGCAAAA TCTAGCTAAA
31551  TAAAGCAGAA ATGAAACAAA AAGTGGATTG GTCATTTCAA AGTTAGTTTC
31601  TTTATAGTAT TAAAACACAG GGGACTTCCT TATGCTGGCT CAGGATAACT
31651  GGCCTCCTTC TGATTGATTG CTATGAATCT TTTGATTTTT TTTTTTTTTT
31701  TGAGATGGAG TTTCACTGAT GTTGCCTAGG CCTGGAGTGC AATGCCACGA
31751  TCTCATCTCA CTGCAACCTC CGCTTCCAGG CATCAAGGGA TCCTCCTGCC
31801  TCACCCTCCC ACGCAGCTGG GATTACAGGC TCCCTCCACC ATGCCTGGCT
31851  AGTTTTTGTA TCTTTAATCT AGAAGGACCC CCACCCTGCA GCCCAGGCGA
31901  CAGACTGATA CCCCACCTAA AGAGATCCAC CCGCCTCATC CTCCCAATTT
31951  GCCAGGGGGC AGACTGCATT CCACCGGTCC CTGATTTGGG TGCTTAAAAC
32001  TCAGAATTTT CTTGGGGATT TTGGTCTCCG ACGTTATCGG GGAAAACTGT
32051  TTTTAACCTT TTATTTTGAA ACAATTTTAG GATCTTTGAA AAGTTGCAAA
32101  AATCCTCCAT GGAATTCCAT TTACCCCTTC CCCCAGTTTT TTCTTAGNNN
32151  NNNNNNNNNN NNNNNNNNNN NNNNNNNNNN NNNNNNNNNN NNNNNNGGC
32201  TCCCGCCCCA TGCCTGGCTA ATTTTTGTAT TTTTAGTAGA GATGGAGTTT
32251  CACCATGTTG GCCAGGCTGG TCTCAAATTC CTAACCTCAG GTGATCCACC
32301  CGCCTCAGCC TCCCAAAGTG CTGGGATTAC AGGTGTGAGC CACCGCGCCC
32351  GGCTTTTTGA TTTTTTTAAA CTGTCATTAC TCGGGGTTTA TAGTCTACTA
32401  CTATATTGCT GAGAACAGTT TTCAAGATTA AAAATAAAAA TGTTTTCTGT
32451  TTCTCTTAGT TAAAAAAAAA AACCTGTCTC TCATTGTAGG ATTATTATTC
32501  TCTCTTTTCA TTATAGATGT ATACTATTTC TACCTTCTGT GTTAAAAATA
32551  CTTTTCTGGG CCGGGGGCAG TAGCTCACTC CCGAAATCCC AGCACTTTGG
32601  GAGGCCGAGG CGGGCAGATC ACGAGGTCAG GAGATCAAGA CCATCTTGGC
32651  TAACACGGTG AAACCCCGTC TCTACTAAAA GCACACAAAA AAATTATGGC
32701  GTGGTGGTGG GTGCCTGTAG TCCCAGCTAC TCGGGAGGCT GAGGCAGGAG
32751  AATGGTGTGA ACCCGGGAGA CGGAGCTTGC ATTGAGCCGA GATCGCGCCA
32801  CTGCACTCCA ACCTGGATGA CAGTGTAAGA CTCGGTCTCA AAAAATAAAA
32851  AAATAAAAAA AATACTTTTC TGACTTAGAG AATCTGGGTG AAGGGTAAAT
32901  GGAATTCCTT GTACTATTTT TGCAACTTTT CTATAATCCT AAAATTGTTT
32951  CAAAATAAAA GGTTAAAAAA ATATTTTCCA GACTACTTCA GAAACCTAAT
33001  TACTAATAAT AATTCTGAGT TTTAAGCAAC CAACTTAGAA ACTTTTGGAA
33051  TGCAGTCAAC CCACTGACAA ATGAGGACTA TCTGTACTAT AGTATTTTTT
33101  TAGACGGGGT CTCAGTCTGT CACCCTAGCT GGAGTGGTGG GGTGATCTCA
33151  GCTCATTGCA ACCTCTGCCT CCCAGGCTCA AGCGATCTTC CCACCTCAGC
33201  CTCCTGTGTA GATGGGATTA CAGGCAGGCT CCACCATGCC CAACGAATTT
33251  TTTTGTATTT TTAGTAGAGA AGGGGTTTCA CCCTGTTTCC CAGGCTGGTC
33301  TCAAACTCCT GAGCTCAAGC AATCTGCCTG CCTCGGCATC CCAAAGTGCT
33351  GGGATTACAG ACATGAGCCA CAGAGCCTGG CCTTTTAGTC TATTTCGATT
33401  CTTCATTTCA ATTCACTATA CTTTTTTTCT AAGTTTTAAA ATATTTTTTA
33451  TCTTTTACCA TTGACATTTT GTGTTGTTTT ACAGCTTCTT TATATTGGTC
33501  TGCATTCCAA AGACAAAATG AAGTCTCTTA TGTTTTGTGA TATGTGTTAA
33551  AATAATTGAA CTAGACAAGA ATGTTAGGCC CAAGTGAGAT GAAGGAAAGG
33601  CTCTTTGATA AGCATTTGGC ATTTTAGATC AGAGATGGCA AGTACGTATG
33651  ACATAGCATT CTTCTTTTAT ACATTTCAGA TATTATTTGT TGATCAGACA
33701  CTCTTCTTCC TGTCTTGGAC CACACAGTGT TTTAGGTATC TGCTGTCAGT
33751  TGATCAGAGT TGGCATGAGA AACAAAAAAA ATCTATTGGC ATCTCTGACT
33801  TAGAAGATCA GTTTTGGGAG AATCTTCTGG AATATCTATT CTATTCTTAA
33851  GTTTAATGAG TAATTTCATC CATTTTATGA AGTAACATAA CAATTCTGGA
33901  AGCCTAGTTA TTTAAAGAAT GCTTTAAGCT TTGTTTCTTG TCACTTCAAT
33951  TTTCAGATGT TTGTGAAACC AAGTCTGCTA TTTTAATAAA ATGTTCTTAA
34001  AGTATAATGT AACTTTAAAA AATCTACATA CTTGTGTGTC ACATCTTTAG
34051  CCTTTAATTG GGTGACTTTT TAAATGTTAT CTACTTTTAT TCTTATGTTT
34101  TCCTTCCCAG GAGTGGACCT ACCCTATGAG ACGAGAGATG CAGGTATGGC
34151  AACCTTTTCT TTGTTCAAAC CAACCCATGT TATTATCATA ATAAGAACCT
34201  TAGTTTATAG GATTTGAGAC CTGCTGATTT CATGATCTGT AGGTTCATCA
34251  TTATGTATTT TAAATAATTA TTTTAAATAT TTAAGGTTAA TCTTGGATCT
34301  TAAAACGATG GGAAATTAGA AAGAGGAACG TAGTAATAGG TGTATGTGCT
34351  TAATGAGTCA CTTTCTCTTG GTTTTTTTTT TGTTTTTTTT TTTTGAAAC
34401  AGAGTTTCGC TCTTGTTGCC CAGGCTAGAG TGCAATGGCA CGATCTCGGC
34451  TCACCGCAAC GTCCACCTCC CGGGTTCAAG TGATTCTCCT GCCTCAGCCT
34501  CCCGAGTAGC TGGGATTACA GGCATGCGCC ACCACACCCA GCTAATTTTG
34551  TATTTTTAGT AGAGACAGGG TTTCTCCTTG TTCAGGCTGG TCTCACACTC
```

FIGURE 3, page 11 of 29

```
34601  CTGACCTCAG GTGATCCAGT GACCTCAGGT GATCCACCCA CCTTGGCCTC
34651  CCAAAGTGCT GGGATTACAG GCATGAGCCA CCGTGCCTGG CCAATGAGTC
34701  ACTTTCTTTT TCCTCACGTG AAAAATTGGA TACTTTCTTT GTATTCCTTT
34751  TGAAAGCAGT TTGCTTTCTC TGTTTGTCTA GATAAGTTAG GGAGAGTTGT
34801  CTGTACAACA AATAAGCATT GTTCATTTTG TGTCCGATTT TTAATCAACT
34851  TCCACAATTA AGTCTTCTAG AAGATCAAAT TGAATACTTT CAGTTTGGAA
34901  TGAATTAAAC GATAGCTAAC CCTCATAGCA GTTCATTTTC TTTTGCATTT
34951  CATACCATTT ACCGTCAAGT CTGTTTGCCC CAGGATTAAG CAGTATCTTG
35001  TTCCTGGGAA TCCCATGACT TCTAAAAATC TGTTACTTTT CTCTCTTAAT
35051  GAAAGTTCAC TTTGAAAAAA TAGGTGAGTA CCTATGAGGC ATTTTACTTG
35101  GTGTTAGGAG GAATGCAAAG ATGACTAAAT GTAATTTCTG CCCACAAAAG
35151  CCTGGTGGAA GAAATCAGTT TTATATACAA ATAATTATGA CTTATAGAAC
35201  TGAACTATAA AGTTACTGTT AGTATCTAGG GTATGATATA TCCAGACTGA
35251  AAGCTTTCTG TATTGAATTT ACATAAAATA AATTTGAATT CAACATCTGG
35301  AAGGTACATA CTTGTTGAAA TTTTGTCAAC TGGCAAATAT TTGAATTTGG
35351  AATTTTTATG TTACAGTAAT AATTTGCTTC TATTAACTAT AGATAATAGT
35401  TTTAGGTCAG GCACAGGAGT TCATGTCTGT AATTCCAGCC GTTTGGGAGG
35451  CTGAGGCAGA AGGATCACTA GAGCCCAGGA GTTCCTTATC AGCCTGGGCA
35501  ACATAGTGAG ACTTCGTCTC TATTTTTTAA AGAAAAAAAA AAAGATTAAA
35551  AAAATAGATA ATAGTTCCAA TCTTGTTGTA TCTTGTGCTG CTTTTGATTT
35601  GGCCAAATAA GGTTTGTCTT ATTTATATAG CCTTATAGAT TTAAATTGCT
35651  GATGGTAAAT ACCTCAAATT TTTTTTTTTC TAGGAAATTT TACCTGGATT
35701  GTTCTTAGGC CCATATTCAT CTGCTATGAA AAGCAAGGTA TGAACTTTGT
35751  TAGATTCATC AAGAGAGACT TTTATTAACC AACTTTTCTT GGGTAAGTTT
35801  TTTAGTAATA AAGAGTTTTA TTTTAGGGAG CATCCACAAA TACTGTCTGT
35851  TAACAGTAAT TGTCACTCTG GAGTACCTTC CTCTTTCCCT ATTTTACTAG
35901  ACCAGTAGTT CTCAAGTGTT TCACCACAAA TCAGAGTTTT TGTTTTTTCC
35951  TCATGAAATT TGTATGTTTG AAAGATTTAC CAAATAACTG ACCTTTAATA
36001  ACTTATTTAC TCTCTAAAAC ACTAGACATC TGTAATTGCT AATCATAGCT
36051  TCAGAACAAT ATGAGATGTA GTTAAAGCCC AAAATAAGGA ATTTCAATGT
36101  TTAGTTAAAC CTTCCTTATC AAGGGTAAGA CTGTGTGTGT TAATTGAAAG
36151  TCATTCACCT TAGTTCTGTT TTGCCAGCCA GACTTTAGAG AGCTAGTTGG
36201  TATCCCCGCT CTGAAATTTG AAACTTTTTG AGCACCAGTA TGTCACTCGA
36251  AGGAAATCCT CACTGGAGTA TTTCGGATTT CGGATTTTTG GATTAGGGAT
36301  GCTCAATTAT AAGTATAATG CAAATAGGCA AAACAAACAA ATCCAAACTC
36351  TGAAATATTT CTGGTCCCTG GCATTTAAAA TAAGGGATAT TCAATCCGTA
36401  TAGATATTCT ACATAGTCAA ACTTTAATGG ACTTACTCAG TTGCAGTTAA
36451  AATAGGTAGA TCTCATTTTA ATAAATATAG CAATGTTCTT GCCACTTCTA
36501  AAAGATTCAA TGCTACTAAT TCTCTTTGAG TTACAACGTG GAACATATCA
36551  CAGATGTCTT TCCCCAATAC TTTGCCTATT CAGAAGTCAG TATACTTAAA
36601  TTGTGTTTGA TATATCCATA ATTTAATTTG ATGTTCTTAG GAATTTAACC
36651  GGTTTTAAAA GGTCATTGAT TTTGAAACTG GAAGATTTTT TTGACAGTTG
36701  AGACATGGCT AAGAGTAAAC CTGGTCATCT TGATGATTTT TGCTTAGTTG
36751  GAAAGATAGG GAGTTAGTAA AAATAAGTAC TAGGGAAAGG ATAGGGCAGG
36801  TAACTATAGA CATAGCCGTA ATTTATTTTG TAAAAGACAG ATGTAAACAA
36851  GGTTATTGTC CATATAATTT GCTATTCACC AAGTACTAGT CTTCCAGATG
36901  GTTTAGATA ATTTACATTT TTGAAATTCC CACTGTACTT TATAAATATA
36951  CATACAGTAT TTATCACATT AAATTAAAGT ATTTGTTTAA AGGTCTATCT
37001  CCTCAATGGG AGGCTGAGGC AGGCGGATTA CATGAGGCCA GGAGTTCGAG
37051  ACCAGCCTGG CCAACATGGC AAAACCCCGT CTCTACTAAA AATACAAAAA
37101  TTAGCTGGTT ATGGTGGTAC ACACCTGTAA TCCCAGCTAC TCACGAGGCT
37151  GAGGCGCGAG AATTGCTTGA ATCTGGGAGG TAGAAGTTGC AGTGAGCCAA
37201  CATGGCACCA CTGTACTCCA GCCTGGTTGA CAGAGTGAGA CTTTGTCTCA
37251  AAATGAAACA AAAACACGCA CAAAAAAAGG TCTAGTTCTT CAAAACTTCT
37301  TTTCTTGAAA TGTCACCATG GTCTTATTAG ACAGGAAAAG CCTCTGTGGC
37351  AGTTTATTTC CCACCCTAGG TAACCATAAT ATAGCCCATA TTTCTTTTCA
37401  TACCATTATC TAAAAACAAC AACAAAAAAT AATAATGGAG ATAAACCTAA
37451  ATGGATAAAC TCCTTTTTAA ACACTCATTT ACTGTTATTA TTTTGTGGGA
37501  GAGGAGTGGG GTCTTGCTCT GTTACCCAGG CTGGAGTACA GTGGCGCGCT
37551  CTCATAGCTC ACTGTAACCT CAAACTCCTG GGCTCAAGCT GTCTTCCCAC
37601  CTTAGTCTCC CAAGTAGCCA GGACTACGGG CACACACCAC CATGCCTGGC
37651  TTAATTCTCA AGTTTTTGT AGAGATGGAG TCTGGCTATG CTGGCCACAT
37701  TTACTTAAGT ATATCTTTTT ATTAAATTCA AATACAGTTT AAATAAAAGG
```

FIGURE 3, page 12 of 29

```
37751  GACAAATTTA GGGCCTTTGT AATTAGTAAA CGGTTTGTTT TTGTAAAGTT
37801  TTTCTACTGT TTTTAAATGT GAGGTAAGGT CATAATTTGC TTCATATTAG
37851  GTTGGTGCAA AAGTAATTGC AGATCTGCCT CTGAAAAGTA CAAAATCTAT
37901  TCGCTGTTAC GTTAGGGCTC TATTTTGATA GTTTATTTTT ATTTAGTAGT
37951  AGTCTATTGG GCCTTCAAAA CTTGTTTAAG CATATTTATA CATAATTATG
38001  TGCATCGTCT TGTGCTTTCT CACATTCATA AAGTAGATAG GAAAACTCCA
38051  TAGGCATCAA GTGTAAACGA AGGACTTAAT GTTGAATTTG TTGTGGAAAT
38101  TGGCACAAAT CTCAATATAG AACATTGGTT AATTATTAAT CTTACCAAAT
38151  GCTTATCTCA CTTTCCCTAA CTCAAGTTAT ACTCAAGAAA TACAAAGATA
38201  ATTGAATTCT AATCTATGCT GACATAAAAC TTGCTGCAGA AATTAACACT
38251  TAAAACTTGC AAATTATATT GTCTTAGCCC AGGCTGCTCA AACAAAATAC
38301  CATAGACAGG GTGGCTTAAA CAACAGACGA TTATTTGAGT TCTGGAGGCT
38351  GGCAAGTCCA CAGTCATGGT CCGGCTCTGG TGAGGACCCT CTTGCTGGCT
38401  CGCAGATCCC TCCCTTCTTG CTGTATCCTC ACACGGCCAA GAGAACGAGT
38451  TCTTGCCTCT TCTTACAAGG GTACAATCCT GTCATGGAGG TTTCTACCCT
38501  CATGACCTCA ATCTAAAACT GATTATCTTC CAGAGACTCC ACCATCACAT
38551  CTTGGGGGTA AGGATTTCAA CATAAGAATT TGAGGTGATG CAAACATTTA
38601  GTTCATAACA CATATAAATT ATTTTTTTTT ACTTTGCTCA TGAATTATTA
38651  GTGCTACTGT TTTGTACTAT TTAAAATGCA GAAATGGGA ATTAAATATA
38701  TAGGATTTAA AACAATGTGT CAAGAAATTC AAGGTTATCT GATTCTCATG
38751  CCATCGTGAC TTGTTAGTTC ATTTATTGAA CAGGTAATTA TTGAACAACT
38801  TAACTAGTTA TACATACTTG ATACTTAAGT GAATTGTATT ATACATTTTA
38851  CACATACTAT GTATCAGTGA ACAAATAAAA ATCTTTTCTG TCATGGAACT
38901  TAATGCTCTA GGTAATAAAA TAACATCTAT AAACTCACTT AAACTTATCA
38951  CTAGCAAATG AAAACTTATT ATCTGGTAAT TTCTAGAATT GTCATGTTAA
39001  ATTGCTTTAA GTATGGAGCC AAAAGCACTA CAGGTTGAGT ATCCCTAATC
39051  TGAAAAATCT GAAATGCTCC AAAGTGAAAC TTTTTGAGTG TCAGCATGAC
39101  AGCACAAGTG AATTCCACAC CTGACCCCAT GTAATGGGTC ACTGTCAAAA
39151  TTTTGTTTCA TGCACCAAAT GACTGTATGA AATTACGTTC AGAGTATATA
39201  TGGTGTGTGT GAAACATAAA TGAATTTTGT GTTTAAACTT GGATACCATC
39251  CCCAAGACAT CTGAGTATGT ATATGCAAAT ATTTCAAAAT CTGAAATCTG
39301  AAACACTTCT GGTCCTACCT TGGGACCAGC ATTTTAGATA AGGGATACTC
39351  AACCTGTATT GAATATAATA AGATGTCATT GAAGTTGCCA TTTTTAACTT
39401  CAGGAAAATT TTTAAATGGT AAAAGGTTAA TTAGATTCTG TGAAGTATGT
39451  AAATTAATTC TGACTCTTAA AGTATACTGG GAGAGGCAAG GAGTTGTCTA
39501  GAGATTTGGG TTCCAGTACT GCTGTTAACT AGGTCGGTGA TGTCCAAGTA
39551  TTTGGTAATG TAACTGTTTT ATGTCTTAGT GGTTCTCTCT AAACAATAAA
39601  GATTGCAGTC AATATATATT AACTACCATT TATTAAACAC TTGCTGTGTG
39651  TCCCAGGTGC TATGCCAAAC ATCTTACATA AAGGTTCCAT CAAGCTCTAA
39701  AATTGTAGGT ATGAAATATC CCTGTTAACC TTTTGAGGAC ATTAATGTAT
39751  TAATCTTGAA TCATTGAAAT ATCTTGCTGC CCACTTCAGG TATATTATAA
39801  AATTAGCTTT AATTCCCTGG ACTTAAGCAG AGATGTGGGT TCTGTGTATT
39851  TCAAACATC TGTGTTATAT AGTAAGATGA TGTTTGATAT TTAAAATAT
39901  TTATCTTCCC TGTCCTCCCC CTGCTTTTTT TTTTATACAG CTACCTGTAC
39951  TACAGAAACA TGGAATAACC CATATAATAT GCATACGACA AAATATTGAA
40001  GCAAACTTTA TTAAACCAAA CTTTCAGCAG TTATTTAGGT AAGAATTATT
40051  GCTATGATTT GTAAAACACT TAATGAAGTT TCATTTCAGG TTTTGTACCA
40101  TCAGTTGTTT CTGTACATAT CTAGTTTGTA AAAATGGGTC ATATAGTACA
40151  TAGTTTTTTA AAATAAATTT TACTTAAAAT ACTTAAATAA ATTATGCCCA
40201  TAATGCAGAA TTCTAAAGGT TCAAAGAGT GTATATTGTC AAGAAGTTTC
40251  TGGGAAAGTA AAAATAAAAA AGAATTTAAA AATAATGTAT ACTGAAAAAT
40301  AGGTTTTAGT GTACATTATT TTATCTCTTG AGGGATAAAG GAATTGAGTA
40351  TCTAGGGGAT AGGTTTAGGG AAACAGCATC TACTGTTACC TCTTTATTGG
40401  GTAGTTTTTG AGTGTTAGGT TAAATTTATG AGCATAGTCT TATAGATAAA
40451  TTTTTTTTTA CATTGGCTTT CTTTTTACT TTATATTTTT TGGAGATTGG
40501  TTTATATCGG TATGTATATC AAACTGCTTA TTCTTTTAA GTTGCATTGT
40551  AATCCATTGT ATGGCTATAC TAAAATTTAT TCAATTAGTC TGTTAGATAT
40601  TTAGATTGTT TCTGGCCTTG TACTAATATG TATAGCATAT AGTGACTATC
40651  ATTGTACATA TTACTCAATT TATATGTGAG CATATTGATA GGGCTTATTT
40701  GCAGAATTGC TGGATATAAG AGTATGAACA TTTTAAATTT TGATAGATGT
40751  TGCAGATTGT TTTCCAGTGC GTTGTATCAG TGTACATTCC CATTATCAAG
40801  TATGTGAGAG TGACTCTTCC CTTAGTATCT CTCCAAGACG GAATTGTGAA
40851  ACATTTTTAA TTTCTCAAAG TCTAATGGAG TAAAAATGGT ATCTCATTTG
```

FIGURE 3, page 13 of 29

```
40901  ATGTTCTTAT TTATCTTGTA AGTTCAGTTG AGCATGTAAT GGTTTTTAAT
40951  GTTCTTTATT TTAACTTCAT TTTTAAAATA GAGTATATTA CGCATGGTAC
41001  AAAAGTGAAA GGATATGTAA ACATATATAA TGAAAGTAAC TCTACTTTTT
41051  CTCTTAACCC AAGCCACCTT GCTCCTATCC TGGGAGGCAG CTTCTTCCTT
41101  CAATATCTAT GTAAAAGTAT ATATGTTAAA AATATTTTAG GCCAGCACGG
41151  TGGCTCACGC CTGTAATCCC AGCATTTTGG GAGGCCGAGG TGGGCAGATC
41201  ACCTGAGGTC AGGAGTTCGA GACCAGCCTG GCCAACATGG CAAAACCCCA
41251  TCTCTACTAA AACAAAAATT ACCTGAGCGT GGTGGCACAT GCCTGTAATC
41301  CCAGCAGCTC AGGAGACTGA GGCAGGAGAA TTGCTTGAAC CCAGAAGGCA
41351  GAGGTTACAG TGAGCCGAGA TCACACCACT GCACTCCAGC CTGGGCAACA
41401  GAGCAAGACA CCGTCTCAAA AACAAAACAA AACAAAACAA AAAAAAAACA
41451  GTGCTGTGGC TTACACCTAT AATCCCAGTA CTTTGGGAGG CTGAGGAGGG
41501  TGGATCACGA GGTCGAGATT GAGACTGTCC TGGCCAACAC AGTGAGACCC
41551  CGTCTCTACT AAAAATACAA AAATTATCTG GGCGTGGTGG CACATGCCTG
41601  TAGTCCCAGC TACTCAGGAG GCTGAGGCAG GAGAATCACT TGAACCTGGG
41651  AGGCAGAGGT TCAGTGAGC CAAGATTGCC CCACTGCACT CCAGCCTGGC
41701  GACAGAGCAA GACTCTGTCT CAAAATAAA AAAAAAATT TAATGCTCTG
41751  CTTTATTTTT ACAATGAAAC CAATCTATAA ATATCTGTAA ATACAAGATA
41801  CATACTCTAA AATACATTGT GTGAACATAT AATAGAATAC TATGTAACCA
41851  TGAAAAAGAA TGAAATATAT GTATGTGTTT GGATTTGGGA TGATCTCCAA
41901  GATAATGCAT TACATGAATA AAGCAGGGTG TGGAACAATG TATATATTTG
41951  CAATGTGTTG AGTAAATATA TATATACTAC ATTCCATATA TTTATTCTTA
42001  ATATATGCAT AGAAAATTTC TGGACCAAGA GGCTAGAAAC TTCATAGTGA
42051  TTGCTTCTAA GAAGGAAAAT TCAGGGCCTG TGATGGTAGA GGGACGTATT
42101  TTTCTTTCGT TTTTAATTTT GTTTTTTTTT GTTGTTGTTG TTTTTTTTTT
42151  TTTTTTGAGA TGGAGTCTCA CTCTGTCACC CAGGCTGGAG TGCAGTGGTG
42201  TGATCTTGGC TCACTGCAAC CTCTGCCTCC TGGGTTCAAG CGATTCTCCT
42251  GCCTCAGCCT CCTGAGTAGC TGGGATTACA GGCATGTGCC ACCACACCCA
42301  GCTAATTTTT TTTTTTTTT TTTTTTGGA CAGAGTTTCG CTCTGTTGCC
42351  CAGGCTGGAG TGCAGTGGCA TGATCTCGGC TCACTGCATC CTCCGCCTCC
42401  CAGGTTTAAG CAATTCTCTG CGTCAGCCTT CTAAGTAGCT GAGATTACAG
42451  GTGCCCACCA CCACTCCCAG ATAATTTTTT TTGTATTTTT AGTAGAGACG
42501  GGGTTTCAGC ATCTTGGCCA GGCTGATCTT GAACTCCTGA CCTCTTGATC
42551  CACCTGCCTC AGCCTCCCAA AGCACTGGGA TTACAGGTGT GAGCCACCGC
42601  ACCTGGCCTA ATTTTGTAT TTTTAGTACA GACGGGGTTT CACCATGTTG
42651  GCCAGGCTGG TCTCGAACTC CTGACCTCGT GATCTGCCCA CCTCGGCCTC
42701  CCAAAGCACT GGGATTTACA GGCGTAAGCC ACTACGCTCA GCCGAGGGAC
42751  ATATTTTTCA TGGTACCCTT GATATCCATG GGGGATTGCC TCCAGGAACC
42801  CCCATGAATA ACAAAATCCT CAGATGCTCA AGTCCCTTAT ATAAACTGGT
42851  GTAATATTTG CATATAACCT GTGCACATTC TCTCATATAC ATTAAATCAT
42901  CTCTAGATTA CTTCTAATAC TTAGTACAGT GTAAGTGCTG TGTGAATAGT
42951  ATTGGATTTT ATTTTTATTA TTTTTAGTGT TGTATTTTAC CTTATTTTTT
43001  GTTAATGTTT TTTATTGTTG TCGGTTGAAT CCACAGGTAT GAAATTCTTG
43051  GATATGGAGG GCTGACTCTT TACTTTTGTA GTGTTTTTTT TTTACACCAT
43101  ATTTAGTTTA TTAAAACTAG TTATTAAAAA GGAATATCCC AAAACACTGA
43151  TTTTTTTTTT TTTTTTTTT TTTTTTGAG ACAGAGTCTC GCTCTGTCAT
43201  CCAGGCTAGA ATGCAGGGCT CACTGCAACC TCTGCCTCCC AAGTTCAGGC
43251  AATTCTTCTG CCTCAGCCTC CTGAGTAGCA GAGATTACAG GCATGTGCCA
43301  CCACGCCTGG CTAATTTTTG TATTTTTAGT AGAGACGGGG TTTCACCATG
43351  TTGGTCAGGC TGGTCTCAAA CTCCTGACCT CGTGATCCGC CTGCCTTGGC
43401  CTCCCACAGT GCTGGGATTA CAGGCGTGAG CCACTGCGCC CGGCCTGAAT
43451  TTTTTATAAT TATGAAAGAA ATACTTTTTT TTTTTTCAAA GATAGGATCT
43501  TTCTCTGCTG CCCAGCCTGG ATTGCATTGG CATGATTTCT GTTCATTGTA
43551  GCCTTGACCT CCCAGGCTCA AGCAATCTTC CTGCCTCAGC CTTCCAAGTA
43601  GCTGGGACTA CAGGTGCACC ACCGGATCGG CTAATTTTT TTTTTTTTT
43651  TCTAGAGATG GGGTTTTGCT GTGTTGCCCA GGCTGTTCTT GAACTCCTGA
43701  GCTTAAGCGA TCTACCCACC TCAGCCTCCC AAAGTGCTGG GGTTACAGGC
43751  ATGAGCCACC ACACCTGGCC ATGAAACACT TATTCTTTAT AAGTACTTCG
43801  GAAGGTATAG AATGACACCA AGAAAAATAT TTAAATCATC TACAGTTCCA
43851  CAATTCAGAG AAAACACTTT TGTTAACATT TGGAATATTT CCTTTTAAAT
43901  CGTTCTCTGT TGTGTATGTG TATTTACGTA TATATGCATA GAATTATTAA
43951  AGAAAATGAG AATGTTTGTAT TTTAAAATAT CAAACTATAT AAGGTGAAAC
44001  TAATCTTAAG AAAAAACAAA AAAGCCAAAA AATCATACTA TTCATTTCTA
```

```
44051  ATGTGTACAG ACTTTTTGTT TTAAATTATA ATGTTGTTTG TGCAGGTTCT
44101  TTATCCTAAT GGAAGAACCA TTTCTCCTTA AACTTTTACA ATACTAGCTT
44151  CTTAGAGATT GATAGTTCTA CTAGCAGTGC TTGACACTGA AAATGTTATG
44201  CGTTAAAATA TTTAATTTCA TTCTGAGTTA ACATTTTTCC CCTGAAGCAT
44251  TATTTTATGT AACTGGAATA CCCAGTCACT TCAGGATACA GTCATTGTCG
44301  AAATCCTTGT AGGTTAAATA TTGGATTTTC CTCAGATCCT GAGGTTCAGC
44351  TTCTGTGTTT TTTTTTGTTT GTTTTTTTGT TTTTTTTTTT TTGTTTTTGA
44401  AACAGAGTCT TGCTGTTTCA CCCAGGCTGG AGTGCAGTGG CACAATTTTG
44451  GCCCACTGCA ACCTCTGCCT CCCGGGTTTA AGTGATTCTC CTGCCTCAGC
44501  CTCCTGAGTA GCTGGGATTA CAGGTGTGCA CCACCATGCC TGGCTAATTT
44551  TTATATTTTT AGTAGAGATG GGGTTTCACC ATGTTGGCCA GGATGGTCTT
44601  GAACTCCTGA CCTCAGGCAA TCCACCTGCC TCGGCTTCCC CAAGTGCTGG
44651  GATTACAAGC ATGAGCCACC ATGCTCAGCC TCAGCTTCTC TGTATTAAAG
44701  TCCTGAATTC TTTGAAGTTG TTACCACCTA AATGATCATT GAAAACTGT
44751  ATTTTTAGT GCAAATTGT TCTTAAAACT AATTAATAA CTTAGCTAAT
44801  TGCCTATAGT TGTGTTAATA AACAGTGGTC TTAGAAACGC TTAGAAATGG
44851  AAGTTTTTTA CAAAAATAAG CTAACATATT TAAAATGCCT TTTAAGTATT
44901  TTGTAAAGTG TAAAATTCAG TACAGGTGCT CTCTCAGCTA GTTTTTTTTT
44951  TTTTTTTTTT TTCCCCTTTA CTAAAGATGA GTTCAAACAG TGAATGTTTG
45001  ACTCCTGGTT CCATAGACCA TACCTTCCGT TTTTATTTGT TCGTTCTCTT
45051  AGACTTTGGA CTTCCTCTGA AATGTCCTCT GTAGGTTCAT GAGCAGGAGT
45101  CACAGGACCA CTTAGAGAAC AATCTTCTGG TCTTAGAGAA ATTGGTAGAA
45151  ATAAAAGAAT AACATAACGA TTACAGGTAC TTTTGTCTTT ATTTCTAGGT
45201  CCACTCTAAT CTAGAGGAAT GTATCTTCCT GCTTGTGATT TTTCTATTTT
45251  AACCAGATGG TTCATTATAT GCAAATAAAA TATGTATTTA TTTTTGAGAT
45301  AAGAATCTTG CTCTGTTACC CAGGCTGGAG TGCAGTGGCC CAATCACAGC
45351  TTACTATATC CTTGACTTCC AGGCTCACAC AGTTCTACCT CAGCCCCCTT
45401  AGTAGCTGGG ACTATAAGTG CACACCACGA CACCCAGCTA ATTTTTTAAT
45451  ATTCTGTAGA GATGGAGTCT CCCTCTGTTG CTCAGGCTGG TCTCGAATCC
45501  CTGGGCTCAA GTGATCCTCC CACCTTGGCC TCCCAAAAGA GTTTCTTTTT
45551  GCTGGGATTA TAGGCATGAG CCCATTGTGC CCAGCCTGAT GGATTTTTTA
45601  AATACTTAAA TATCAGAGAT GTTAACATGG TGTTTCAGGT TTTAATGCCT
45651  TCAAGCAATG TAAAATCTAC CACACAGTTC TTGGGAATAT GATACTTTGA
45701  AAGTTGTTTT GCATTCTTGC CATGGTTAAC AAGAAATAAT GAGTTATTTT
45751  TTTAAAGTAC CTTAAGTGTT TTACTTAAAG TGTGCTTATC ACAAAATACT
45801  CTATTTTCAG ATATTTAGTC CTGGATATTG CAGATAATCC AGTTGAAAAT
45851  ATAATACGTT TTTTCCCTAT GGTAGGTACC AGTATTTTTT AAATATCATT
45901  TAAAATTTAT TTATGATTTG ACTTCTTAGT TGTGCTTTTT TTTTTTTTTT
45951  TTTTTTTTTT TTTGAGACAA GAGTTTTACT CTTGTTGCCC AGGCTGGAGT
46001  GCAATGGCGC AATCTTGGCT CACCACAACC TCTGCTTCCC GGGTTCAAGT
46051  GATTTTCTG CCTCAGCCTC CCAAGTGGCT GGGATTACAG GCATGAGCCG
46101  CCATGCCCAG CTAATTTTGT ATTTTTAGTA GAGACGGGGT TTCTCCATGT
46151  TGATCAGGCT GGTCTCAAAT TCTCGACCTC AGGTGATCTG CCTGCCTCAG
46201  CCTCCCAAAG TGCTGGCATT ACAGGCGTGA GCCACCGTGC CCAGCCCCTT
46251  TAATTGTGCT TGTAAAGCTT GCTACTTTTA CTTTGCTATG ACTGAAAATT
46301  ATGTGATTGT GTTTTTAAAA GAATTATTTG TAGAAAATTT TTTATGATCT
46351  CCAGAAATTT GAGGAATCAT ATTGTGAATG TATTGGACTT AAATTAAATT
46401  TTGGCTTCTT TAATTTTTTT GGACTTGTAA TAGTTCTATT TATAGCATTT
46451  TGGAAATTGG TGAATCAAAA TAATTTTTAT ACATATAAAT TAGGAAATTG
46501  TTTTCAATAG GTTTCATTTT GTTTCATTAT ATGCATTTAT TTTATGCTTA
46551  CATTAATCCA CATGTCTTTT GCCTCCAGAC TAAGGAATTT ATTGATGGGA
46601  GCTTACAAAT GGGAGGTAAA TAACATTTCC TTTCCTTAAC TAATGTTTAT
46651  ATTTTGGATTA TTTGTTAATT TTTTAGTTGG TATTTGTCTT AAATGCAGGA
46701  TATGAAGTT ACAATTATAT GTAGTAGCTT ACTCCCAAAT TTGTATTTTC
46751  CCAATTACTT GTTTCATTTG GATAGGCTTT CTGGAGTATC CCTGTAGACT
46801  GTTTTCAAAT TCTCTGTGAG CTTTCAGTTT CTTTAATAAG AGTCTGCTAT
46851  ATTCTCTACA CAGTTGATAA TAACAAATTG TAAAGATTTG AAGATATCCA
46901  AGTGATTATA GTATATAAGG AGTTACTTTA CTGTGGTTTC AATGTAGTTC
46951  AGCTACTGAC TCAGGTGTTT TTCTATTAGA ATAATGAATT CATGTTTTTC
47001  AGGAAAAGTT CTTGTGCATG GAAATGCAGG GATCTCCAGA AGGTATGAAG
47051  TTAGAAATAA TCTTTCTTTC TATAACATTT AATTAATGGG CTGTATTTTC
47101  TGGTTGTTTT TAAAATTATT TTCCCCTCTT CAGTGCAGCC TTTGTTATTG
47151  CATACATTAT GGAAACATTT GGAATGAAGT ACAGGTAAGA AAATACCCTA
```

```
47201 AAACCTAGCC ACAGTTTAAA TTCTCATTAA AATGAAACTT AATGGGAATA
47251 GTTTGGAAGT TTGAAGTTCT TATTCCCCTG ATTATTTTTC ATGTAGTCAT
47301 GTTTGATTAG GCAGGCCCTT ATTCCATGAT TAGTCTTAAC CTAATTTATC
47351 TACTTGTATA GATATGCATA GGCTAATATG GAAATCCTAT GGAAAACTAC
47401 TTACCTACCA CAAGGGAATT GGTTGGTATG AGTATAAAAA CTCGTGACCA
47451 CAAATGTTAG TGCTTGCCTT ATTTAAAGGG CTAATTTATC ATGTTCTCCT
47501 TTAACAATAG TTGGATGAAA AATTACCTAG GAATTGTTTG CAGCATCTAT
47551 TTACAATTCA GAGTAGTCTT TCTTATCAAA AATCATCTTT TCCAAGCATT
47601 CTGTATAGAT TTTTTAAAAG ATAGGGGGTG GTAATGAGCT TCTTGCCCCC
47651 AAGACAAAGC AAAAGCCTGG GCCAGTGTAC AGTATTTCCT TTCTCAGCTT
47701 TTCTTGTTCT ACAAATTAGA AATCTTATAG TAATCATTGA CACATCTTTC
47751 TATTTCAGTC CCCTTTTATA TCTAAATTAG AATGGATAAC TTTGCTTAAA
47801 AATATCTATT CTTAAAGGAA TATTATTTGA ATACAAATAT TTATTTATTT
47851 ATTTTGAGA CGGCGTCTTG CTCTATTGGC AGGCTGGAGT GCAGTGGTGC
47901 GATCTCAGCT CACTGCAACC CCCGCCTCCC AGATTCAAGC AATTCTCCTG
47951 CCTCAGCCTC CCTAGTAGCT GAGACTACAG GTGCACACCA CCACGCCTGG
48001 CTAATTTTTG TATTTTTATT AGAGATGGGG TTTCACCATG TTGGCCAGGA
48051 TGGTCTCGAT TTCTTGACCT TGTGATCCAC CTGCCTCGGC CTCCCAAGGT
48101 GCTGGTATTA CAGGGGTGAG CCACTGCACC CAGCCAGAAT ACAAATATTT
48151 AATTGAAAAA AGATTAAACA TGTATTGATG GACTTTATGT TTTATATATT
48201 GTTTTTATTA TTTCGAATTT TGTCAGACCA TTAATGTTGG AAATAACTTG
48251 TATTTATTGG GTCTCTGCTA TGAGCTCAGT ACTATTATAG GCACTTTAAG
48301 CCTCATAACA AAAGTAAATA AACCTCTTTA ACCAGTGATA GTATTTGAG
48351 CTTGAACTTG TACTATATGC ACAAAATGCT TACATTTTAT ATATTTATTT
48401 TAGAGACAGG GTCTTCCTTT GTTTCTCAGG CTGGAGTGTA GTGGCACAAT
48451 CATAGCTCAC TGTAGTCTCA GACTTGAGGA CTCAAGTAAT CCTCCCACCT
48501 CAGCCTCTCA AGAAGCTGGG ACTATACCAC ATCACTGTGC CTGGCTAATT
48551 TTTAAGTTTT TTGTAGAGAT GGGGTCTTAC TACATTGCCC AGGCTGGTCT
48601 CAAAGTCCTG GCTTCAAGCA GTCCTCCTGT GTTGGCCTCT CAAAGGATTG
48651 GGGTTACAGG CAAGAGCCAC TGCACCTGGC CACTTTACAC TTACCTCCTA
48701 TTCATAGTAG TTCCCCAAGG TAGGTGTTAT TAGACTCTTC ATTTTACCAA
48751 TGGACAAAAT AGAGCTTAGA GAAGTTGAGC AAGCTGCCGT AAGCATATAG
48801 CTGGTGAGAA AAGGAATTGT GATATTTAAT CTCATCATGC TTTTTCCATT
48851 ACAACTCATT ACCCCTCTCT ATTGCTAAGT TGTATGATTA TGATTAATTC
48901 ATTAAATAAT GCTATCACAT TAACACTCTT TTTCTGTTTT CAGAGATGCT
48951 TTTGCTTATG TTCAAGAAAG AAGATTTTGT ATTAATCCTA ATGCTGGATT
49001 TGTCCATCAA CTTCAGGTAA CTTTTCTTCC TCTTTAAGGC AATCAGAAGT
49051 AAGATATAAA ATCTTTTATA CATGTAATTT AGGTGTACAA TTTACTTTGT
49101 GAATACTTAA AATTGCCATA ATCTGACTAC TTTGATGCTT TATTCAAGTT
49151 TATATCTCTA TTTAGAAGTA TTTTCTTGGC TGGGTGTGGT GGCTTATACC
49201 TATAATCACA GCACTTTGGG AGAACAAGGC ATTTGGATTG CTTGAGGCCA
49251 GAAGTATGAG ATCAGCCTGA GCAACAAAGT GAGACCCAAT CTCTAAAAAA
49301 TAAAAAATTA AAAAAAAATT AGCCAGTCAT GGTGGTGCAT GGCTGTGGTC
49351 CCAGCTACTC AGGAGGCTGA GATGGGAGGA TTGCTTGAGC CCAGGAGTTT
49401 GAGGCTACAG TGAACAGTGT GTCTTTGCAC TCCAGCCTGG CCCACAGAGT
49451 GAGACCCCAT CCCTAAAAAA TTAAAAAAAC TTTTTTTTCT TAAAGGCTGG
49501 CATTACCAAG AAAAAAGGGT TAAAGACACA TTATCAAATC TAAAGTAAAA
49551 TAATTGCTGT TAGAAATGTC TGATTTTTTT TTGTTGTTCA TTTTGATCAC
49601 ACAGAGCATA AGACAGTTTT GATTCTAAGT ATACTAACTA TAACAGCTTT
49651 TTCTATTCTA TGTTTATCTT TTCCATGTTG TTTCATATTT TGTTGATGCC
49701 TGGCAGATGC ACTGACAAAG ATGATAAGTC TATGAATTAA CCTAATTAGA
49751 CCACGTTGCT CAGTTTATTC CAAGAGGCAA AATCATAGGC TGCAGAATGT
49801 GCTCTGGCTA ATTACATCCA ATTATGTAGG AATAAAGCTC ATGTTTCAAC
49851 ATCAAGAATA TTTATTACAA AATATATTGT TATAGTTACC AAGGTTTAAA
49901 TTTTATTTTA ATATTTAATT TACTTTTAAT TTTTACTACA TTCAAAAGAG
49951 AAACAGTGTC ATCTGTGTTC AGCCTGTTCA TGTAAAATGT TTGTCTTCTA
50001 ACTTTGTAAG TTTCTTTGCC TTTTACCATG TTGTAGAAAA CATTGTTTTT
50051 TTTCATTTTT TTTAAACTAT TTTTTAAGCT TTTCTTTTTT TTGTGGATAC
50101 ATAGTAGGTT AGGTATTTTG ATACAGGCAT GCAATGTGTA ATAATCACAT
50151 CATGAAAAAA TAGAGTATCC ATCCCATCAA TCATTTATCC TTTGTGXXXX
50201 XXXXXXXXXX XXXXXXXXXX XXXXXXXXXX XXXCCTCCCA AGTAGCTGGG
50251 ATTACAGGCA CGTGCCACCA CGCCCAGGTA ATTTTTGTAT TTTTAATAGA
50301 GATGGGATGG CCGGGTGTGG TGGCTCACGC CTGTAATCCC AACACTTTGG
```

FIGURE 3, page 16 of 29

```
50351  GAGGCTGAGG TGGGTGGATC ACCTGAGATC AGGAGTTTGA GACCAGCCTG
50401  GCCAACATCG TGAAACCCTG TCTCTACTAA AATTACAAAA ATTAGCCAGG
50451  CGTGGTGGCA GGTGCCTGTA ATCCCAGCTA ACNNNNNNNN NNNNNNNNNN
50501  NNNNNNNNNN NNNNNNNNNN NNNNNNNNNN NNTGCTGGAA AGGGATCACC
50551  TGAGTATCAG GAGTTTGAGA CCAGCCTGGC CAACATCGTG AAACCCTGTC
50601  TCTACTAAAA TTACAAAAAT TAGCCAGGCG TGGTGGCAGG TGCCTGTAAT
50651  CCCAGCTACT TGGGAGGCTG AGGCAGGAGA ATTGCTTGAA CTCGGGAGGC
50701  GGAGGTTGCA GTGAGCCGAG ATGGCATCAT TGCACTCCAG CCTGCGGAAC
50751  AAGAGCAAGA CTTCGTCACA AAAGAAAAAA AAAATAGAG ATAGGGTTTT
50801  GCCATGTTGC CCAGGATGGT CTTGAACTCC TGACCTCAGG TGATCCACCC
50851  ACCTTGGCCT CTCAAAGTGC TGGAATTACA GGCGTGAGCC ACCACTCCTG
50901  GCCCAAAAAT GTTTTATCAG ATTTTTGTGA TCATTTGTTG GTGTTCCTCT
50951  CACCGGTTTG TAAGAGCTCT TTTTATATTA TGGAAATCTA TTTATAGCCT
51001  ACCGATTTGA AATATCATTT TTATTTTATA CCAAATTCTG ATATGTCCTT
51051  TAGAAGTTTG AAGTTTTCTT TTTTAAGGTG CTTATGGAAT GGCTAGTTCT
51101  AGTTTTTGAA CCGTTAATAT GGTGACTTGA GTTACTGGAT CACATTAGAT
51151  TGGATTTCCT AATATTGAAT CATCCTTTTG GTCCAGCAAT GGATCCCACT
51201  TGGTTATGAT AGACTGTTCT GTTAATGTAT TGCTGGATTG TATTTGCTAA
51251  TCTTTTTGTT CAGGATTTTG GAATCAGTTA AATAGTAAAT TGGTTTGTCT
51301  TTCTTTTTTT TTTCTGTACT ATCCTTTTCT GGTTTTACTA TCTCTGTCAC
51351  AGTGTTCTCA TTTTTTAGTG GAAGCTTTCC ATTTCTCTTT GTGCCATGGA
51401  TCAATTTAAA TTAGATTGGA GTTACTTGTC TCTTAATGCA TTAGTATATG
51451  GCACCTGTGA AATATCTGAC CATAATGTTT TATCTAATTC AGTTATTCAT
51501  TATTTCATTC ATTCATATAT TTTGACAATA GACCAGTTCT CAGACAACAT
51551  TCTTCATTTG GTGTATCGGT TTGATTTTTT CTTTTCTTTC TTTCTTTCTT
51601  TCTTTTTTTT TTTTTTTTTT TTTTTTTTGA GGCAGAGTCT TCTGCTCTGT
51651  TGCCCAGGCT GGACTGCAGT GGTGCAATCT CAACTCACTG CAACCTCTGC
51701  CACCTGGGTT CAAGTGATTC TGCTGCCTCA GCCTCCAAAA TAGCTGGGAT
51751  TTACAGGTGC CTGCCACCAC AACTGGCTAA TTTTGTATTT TCAGTAGAGA
51801  CGAGGTTTCA CCACATTGGC CAGGCTGGTC TCAAACTCCT AACCTCTGGT
51851  GATCCGCCCG CCTCGGCCCC CAGAGTGCTG GGGTTACAGA TGTGAGCCAC
51901  TGCTCCTGGC CTGGTTTGAT TTTCTGATAC CCCTCAGGTC ACTTTGGATG
51951  TATTTATGAT CTTCTGTGTA ATCATTGATT TCATAAGAGT TCTACATAGA
52001  ATTAAGGAAA ATAATATCTT GTACTTTAAT ATCTTTTGGT TCTATTATTT
52051  TTTTTCTTCA TCTGGTTAGT CCATGTTGTT TTTCTGTATT CTAATTTCTG
52101  CTTCCTTGGT ACTTTGCTTT AGTGTTGTTT GCTGCTGCTG TTGTGAATTT
52151  CCTGAGTTGA AAACTTGGTT TCTTTTTATT CTTTCAAAAA TTCAAGGCTA
52201  TTAATTATCC TCTTTGCATT GTGTTAGTCG CATGCTGCAG ATTCTCATCT
52251  GCATTATTTT TATGTTATAG CTTGATATTC TGTGATTTCA GTTTGGTTT
52301  CATTTTTTAT CTAATATGTG TTGAGATTTT TTTTATTGTA TAGGTGACTG
52351  GGTTTTAAAT TTTTTATTTT TGTTCATATT TAGTTTTATT ACATTGTAAT
52401  CACAGAATGT TTTGTAGTAC TTGTATTTTT TGATGTTTTC TTTGTGGTTT
52451  AATATGTAGT TGTTTTCATG AATTTTATGG GCATTTGAAA AGAAGATGCA
52501  TTCTGTTTTC AGGGGATAAA GTTAAATGTA TTTGTCCACT TGATCTGTCT
52551  TGGGCTGAAA TCAGTGAATT GAAATCTTTT ACTATATTGT GTTTATTTTT
52601  TCTTTATTTC CCCTTTTTTG GTTCTGCAAG TTTTTTTCTG TACTTAACTA
52651  TTTGGTACAT AAAAATTCAA GTTAGGTTTT TATTTTAGTT GTACCCTGTT
52701  TAAATTTCAG GGTTTTTTGT TGTTGTTGTT GAGACAGAGT CTTGCTCTGT
52751  GGCCCAGGCT GGAGTGCAGT GGTGCGATCT CGGCTCACTG CAACCTCTGC
52801  CTCCTGGGTT CAAGTGATTC TCCTGCCTCA GCCTCCCAAG TAGCTGGGAT
52851  TACAGGCATG CATCACCACG CCCGGCTAAT TTTTGTATTT TTAGTAGAGA
52901  CGGGGTTTCA CCATGTTGGC CAGGCTGGTC TCGAACTCCT GACCTCATGA
52951  TCCTCCCACC TCGGCCTCCC AAAGTGCTGG GATTACAGGT GTGAGCCACT
53001  GTGCCTGGAC AAATTTCGGT TATTTTACCT TGCAGTTAAC CTCGTTTAAT
53051  ATTGTGAATC CTACTCTTTC TGTTCGCTTG CTACCTTTTG AGTTTTCCCA
53101  TTCCTTTTCC TTCAAGCTTT CTAAATCACT TGATTTTAGA TGCTTTTCCT
53151  CAGTGTAGTC TAGGATTGAG TTTTGCTATT AGATTGGTA TCATTGTTTC
53201  CTAATAGGTG AATTTAACCC ACTTTCATTT ACTGAAAATG ACAGATACAA
53251  TCTTATCTAT TATTATTTCA TATTATGCTT TCTGTTTTAA ATGAATCCTT
53301  TTTTTAACCT TCTGCTATAG TTTAAAATTT TTGGTGTGT TTATGTTTGT
53351  TACATAATTT TTAAGGTTTT ATTTATTTAC TTTTCCTTTT TTTTTTTTT
53401  TTTTTTGAGT TAGAGTCTCA CACTCTTGCC CAGGCTGGAG TACAGTGGTG
53451  TGATCTCGGC TCACTGCAAC CTTTGCCTCC TGGGTTCAAG CGATTCACAC
```

```
53501  ACCTCAGCCT CCCGAGTAGC TGGGATTACA GACATATGTC ACCACATCCA
53551  GCTAATTTTT GTATTTTTGG TAGAGACGGG GTTTTGCCAT GTTGGCCAGG
53601  ATGGTCTCGA ATTCCTGAGA TCATGTGATC CACCCGCCTC AGCATCCCGA
53651  AGTGCTGGGA TTACGGGCGT GAGCCACGGC GCCCAGCCCC TTAATCCTAC
53701  ATTTAAATAG GGATTCAGCC CAATCCTATT ACCTGTTTCC AGGGGTCTTT
53751  ATTAAACTCT TGGACTTTAT TAAGAATAGT TTCATGGAAA CTATATTCCC
53801  AGGGAAAACT ATCCCTTTGC ATATTGGAAA AATATTTTTC TTTTTGCCCT
53851  TATATTTGAA TGACAGTGGC TAGATATAAA ATAGGTATTT AATACTTTTT
53901  CCCTAGTGAT TTTGTACACA GACCTGATAT TAAATATTTT TTGTTTGTTT
53951  TTTATTTTTT GGAGATGGAG TCTCACTCTG TCGCCCAGGC TGGAATGAGT
54001  GCAGTGGTAC AATCTAGGCT CACTGCAATC TCCACCTCCC GAGTTCAAGT
54051  GATTCTCCGC TTCAGCCTCC TGATTAGCTG GGATTACAGG CACATGCCAC
54101  CACACCCAGC TAATTTTATA TTTTTAGAAG AGATGGAATT TCACCATGTT
54151  AGCTAGGCTG GTCTCAAACT TCCGACCTCA GGTGATCTGC CCTCCTCGGC
54201  CTCCCAAAGT GTTGGGATTA CAGGTGTGAG CCACCGTGCC TGGCCTAAAT
54251  ATTGTTTTAG AGAAGTTTGA AGGCAGACCA ATTTTAAGAT TCCCCCCTTA
54301  GGTGAATTGA TTTGTATCAG GAGAAGGTTG TCTAGATCAG CAGTCTCCAA
54351  CCTTTTTCAC ACCAAGGACC AGTTTCATGA AAGACAATTT TTCCACGGAT
54401  GGGGTGGCGG GGGAGATGGT TTCAGGACAA AACTGTTCTA TATCAGATCA
54451  TCAGGCATTA GTTAAGGAGT GTGCAACCTA GATCCCTCGC ATACCATAGG
54501  GAGGGATAGG TTTACCATAG GGTTTGCGCT CCTGTGAGAC TCTAATGCTG
54551  CTGTTGATCT GAGAGGAGGT GGTGCTCAGA TGGTAATGCT CCCTGGAGTG
54601  CCACTCACCT CCTGCTGTGT GGCCTGGTTC CTGACAGGCG ATGGACCGAT
54651  TCTGGGGTCT GCAGTCCAGG GGTGGGGACC CTCATCTAGA TGACCATAAG
54701  ATGCTTTATC AAGGTGTATC CTGGTTTTTT ATGTTTTTGT TTTTTGAGGG
54751  GGTCTCGCAC TGTCACCCAG GCTACAGTGC AGTGGCGCGA TCATGGTTCA
54801  CTGTAGCCTT GACCTCCTGG GCTCAAGTGA TCTTCCCACC CTAGCTTCCT
54851  AAGTAGCTGG GACCATGGGT GCACACTATC ACACCTGGCT AAGTTTTTTG
54901  TTTGTTGTTG TTTGAGACAA AGTCTCACTC TGTTGCCCAA GTTAGAGTGC
54951  AATGGGGCAA TCTTGGCTCA CTGCAACCTC TGCCTCCTGG GTTAAAGCGA
55001  TTCTTCTGCC TCAGTCTCCC AAGTTGCCAG GATTACAGGC ATGTGCCACC
55051  AAACTCAGCT AATTTTTGTA TTTTTTGTAG AGAGACAGGG TTTCACCATG
55101  TAAGCCAGGC TGGTCTGGAA CTGCTGACCT CAGGTGATCT GCCTGCCTCG
55151  GCCTCCCAAA GTGCTGGGAT TACGACGTGA GACCACACAC CTGGCTTAGT
55201  TTTTTAAATT ATTTTTGGTA GAGATGGGGT TTTGCCATAT TTTCCAGGTT
55251  GGTCTCAAAC TCCTGGGCTC AAGCGATCCT CCCACCTTGG CCTCACAAGG
55301  TGCTGGGATT ACAGGCATGA GCCACTATAT CCGGCCAAGA TGTATCTTGT
55351  TGATTGCTCT ACATCAGTTT TTTTCTGAGT CACAGTGTGC CCTTACCACT
55401  TGCAAATTCA AGCCTTCCCT GATTTCAGGA AAGTTGTCTT CTATTGTGTA
55451  TTTACCCTTT TGGTTGTTCC GTTTCTTTTT CTTTTTAGTA TACCCCTTAC
55501  CCCGGTATAG TTTATGTTCC CTTTTTTCTT TGTTATTTGC TATTTTCTCT
55551  GTAATTATTT GCAGCTTTGT TCTTTTTTTT TTTTCCACTT GATTTTTCTC
55601  ACGTTTGTTT TCCATGTCCC ATGCTGCATT GTTTCATTAA ATATTTATTT
55651  GGCATTGTTT TAGTTAGGCA CTGACAGTAA AGCAGAGAAC AAAACAGACA
55701  ATAATCCTTG ACCTCACGAA ACTTATTTAG TGGGAGAATC AGACAACAAA
55751  CAAAATGTAG TAGGCCAGAA GTAATGAATC CAAGAAAAAT AAGGCCATGT
55801  AAGGAAGGTG GGACGAGAAT TGTATTTTTA GAAGGGTGGT CAGAAATGGG
55851  CTTACTGAAA AGTGATATTT GAGCAAAGAC CTAAAGAGAT GCACGTATTT
55901  GGGGAAAAGC ATTTGAGGTA GAGGAATAAG TGTAAGTGGT TTGAGGTGGG
55951  AGCATAGTTC TTAGAAGGAT ACTCATTTCA TCATAGGGCC AGTCCTCTCA
56001  TGACCTCATC CCAACTTAAT CACCTGCCAA AGTCCCCACA TTAAGTGTTT
56051  GGACTTCAAC ATATGAATTA TGAGGGGAAT GCAAACATTC AATCCCATAA
56101  CTGCCATATT TTCTTTGATT AATTTGTTCA TAGTTTTCAT CTGCTTCATG
56151  GTATAAGTTT TATGGCATTT TCTTTATGAC ATTTGGTTAT ACTCTTGCTT
56201  TTCTGTTTTT GTTTTGTTTT GTTTGTTTT TTCTTGCAAA ATCTTTGAGT
56251  AAGACCTAAC TGGTTCCTTC TTGATTATTG GTCATCTTTG AACTGGAGGT
56301  ATTCGTCTTA GATCAGCTAT TTACCCAAGA ATAAAATTGT GGGAAAGCGG
56351  CCAGAGGAGT GGTTGGGGAA GGCTGACAGC TTGAATTTTC CCAGGTTCCT
56401  TTGGTGGCAT GAATCAGTGA GTAAGAAGCA GAGCTCCTTA TATCACAGGT
56451  TTATTTTGTT TAAATTGATA AACACTGATT CATATTAGAA TCACCTGGGG
56501  AATCCTTACC CATGCCAATG AAATCAAAAT CTGTGAGAGT GGGGCCTAGG
56551  TATATAGGTT TTAAAGTGCC TCAGGTGATT CTCATGTATA TCCAGGCTAG
56601  AATTGCTGAT TTAGCCTTTA CTTTTAGCTA TCCAAGATCA ACTGATGCTT
```

FIGURE 3, page 18 of 29

```
56651  GGCTACATGC AACCAAATTT CACTTCCGCC TTACCATACT TAAACAGCCT
56701  GCTGCTTGCA AAAAATGGCA GGTGTAGGTG TTCACATTTT CCTTAATATG
56751  TCCCACCTTC TCCCATAGGC CACTCATATT TCCTGACTTT GTCATACCAT
56801  GCAAGGGCTT GTTGGTTTTA TTTTAGGTCA CCTTTTTTAG CGAGCTATGA
56851  ACTGTACCTA CTCTGGCCCA CAGAGGAGTT ATCTGCTATG CCTAGCTTAG
56901  GATGGTTCTA TTTTTTTTGA AAATTTTATT GTGAAATTAT AATATAGAAA
56951  ATGCATAAAA TGTAAATAAA CATCCATGTA ACTATTGCCG AAGTATGGAA
57001  ACAGAATGTT TACCAGGACA CCAAAAGCCT TTTTCATGCC GCTTCTCAGG
57051  CACAAATCTG TTTCTCCCTC TGTAAAGTAA CCACTATCCT GACGTAGCTG
57101  GTAATCAATT CCTTTTCCCC TCATTCTTCT CATTTTCAGG GTAATGGATG
57151  TTTCCTAGTT TCATCAAATG TTTTCCTTGT TTTCAGAAAA GAGAGAAACA
57201  AAAATGCCTT TATTCTTCTA TCTATAACTG GAAGCAGAGG ACTATTGAGA
57251  TTGCCAATTT AAGTTTTGG TGTTTTTGG GGTTTTTTA AACAGATGAA
57301  GTCAGAGATC ATTATAGCTA ATGCCATACT GACTGGCAGT TCAGCATGCA
57351  GTACCCTAGC ACAAACTATT AGCCGGGCTT GATTTATAGT TATCAGTAGT
57401  TCTGAATTTA TGAGACAGGA ATTTTAAACT TCCATTTCTC TTCAAACAAT
57451  ATGGCACTAG ATTTTTCAAT ACAGATGAAG AATACCAACA GTGTATACAT
57501  TAATCACTAT TTTGGGTATC CAAGAATGTA AATATATAAT TAAGTTAATT
57551  AACTTATTTT TTTTTTAGGA ATATGAAGCC ATCTACCTAG CAAAATTAAC
57601  AATACAGATG ATGTCACCAC TCCAGATAGA AAGGTCATTA TCTGTTCATT
57651  CTGGTACCAC AGGTAAGGAT TTTTTTCTTT TTGGAGAAAT TTGGGAAGAA
57701  AGATAATGAA AGGTGGAGAA CTTGCTACAA GTTACACTGA ACAATTTAAA
57751  TTGTTTAGAA AACTTGTTAA ACTATTGAGC TAATTCCAGA AGGATTCATT
57801  TTATAATGAA TAAATGTGTA CTATAATAAG CTTAAGTCTT TCAAGTAGTA
57851  GTACATCCGT GTTGTAAAGA TTAAAATAAT ACGAATCTGG AGAAGGGGCC
57901  CTAAACACGC TTAGGTGATC TTATTAAAAG TAGAGGGCGG TTAATACAGC
57951  GTGTAGCATG GCTAATGTGA GCTTCTTTCT CTTGCCATCA ATATTTCCAT
58001  CCTTTCCTCC CTCTGTTGCT ATTTCAGAAG TACCCTAAGC CCCTTATTTT
58051  CAAAGTTAAT CCAAGCATGC TCTTAAAATC TTCCTTTCCC AAGACCTTGC
58101  TACCTGTGTT TATCACCTTT GTTTCTCTCC CAACAAAGCA CACAAGGCAT
58151  TTTTACTTTA TTTCCAGTTT TTCCTACCCT GCAGTTCACT TCAATCTTTG
58201  AACCAACAGT TATATAAGGT AGTAAGAACA GCTTATATAC TTAGCACTGA
58251  CCTGGAAATT GAGGACAGGT GATCTGATCC ACAAGTATAG AACTCTTTGC
58301  ACTCTACTGC ACTGCCCATA GTGAGTAATA TGACTGTATA TTCATCCCCA
58351  AGGCTCAACT TCCTAATTGT CATTGACTTT TTCATTTCCT TTGCCACATC
58401  TGTCTAATAA TTGCTCTCCA CATCCTATAG GGTCCGTTTT GTCAGTATTG
58451  TTAACATTCC TTCCTTTTTT TAATAGTGAC CTTAATCTAG TTCAGGTCCG
58501  GATTTGCCTC CTTTCCAAAC TCTTGTTATT TGGTCTGTTC TGTACATTGT
58551  GGCCAGACTT ATTCCCATGA AAGATATTTC TAATATTGAT ATTTTTCCTT
58601  TGCCAAAGCC TCCTTTGGCT TCATTCCTAC AAAAGTTTAT AGAATGCCAT
58651  ATGCCCTTCT GATTTTTTGG TTTCTTTCTC TCATTGTTCT TCTTTATGTC
58701  TGCATTTCAG AAAACAACTG CTGATGGTTT CCTGTGTGTG TCTTCTTTTC
58751  CCCACCTAAA ATGCATCACA TTTAGTCTCC CTATTCTTGG TTCATATGTC
58801  ATCTCCTCAG GAAGACATGA TGATTAATGC ACTCTTCCTC TAACCCCTAG
58851  TCATTTGGAG TTCCCATAGA AGCACAGCAC TTCATCTGAA ACTTAATCAC
58901  AGTATCTGGG TTTAGCCTGA GGGCTAGGAT ATTTTATCTC ATTCAATTGT
58951  ATTGATACTA TATTTTTATC TTTATGAATT TTATAGTGAA ACATTCTTCA
59001  ATTAGAATAT GCCCTCTGAA TTAACATTAT TATTACCATG ATATAACAGT
59051  CCTGTAGGGC ATAAGTTTAA GGTCATGCCA TTGTTAGGCA AAAAACACAG
59101  CAGACCCTCT GCTGGTTTAA CTGTTCCCTA AAGTTTTCCT CCATTGAGAG
59151  TCTAATTTCT TGATTATAAC TTTTGGGGAT ACAGAGATAG CTTTGATTCT
59201  ATGTGGGAGA TTTCTGTACT AGCAGATGCT GGTATGAAGA ATAGATAAAA
59251  GAAAATCTCT TTATATGCTA CATGCCTTCC TTTCTCCCAA CCTAGACTTC
59301  GATAGCTTGA GTGGAAAAAT ATTTTCAGCT GCTCTTCATA ACAGCCTCTG
59351  TGAAAGCAAA AAGATTATCT ACAAAAATT ATACAAATAC AAGATTAATT
59401  TCCTAAATTT TATGCCCTAA GTCACATGTT TATGGTGCCT AAAAAACAAT
59451  TAACTTGATA ACTAAACATT TATGTATTAT CTCTTGAAAA GGTCTATTTT
59501  CACACTATTT CAAAAATTAT TTATTTTATA TGCAATACCT AAGACATAAT
59551  ACTTGAGAAG GAAAATATAT CCTGTCATGA AGATTAAAAA GTTATAATAT
59601  TTAGGTAATT TATCACAAAG GAATTTACTA AATTTTGCTA TATCAGTTGT
59651  GGAATTTTCA TAGTGTATAC ATGATCACTT AATAACAAAA TTTTACTTGC
59701  TGTAACCTTT TAACATGAAT TTATTTTAGT GCCCTTTTAA TCTTCATGCA
59751  ATAACTTTTA GGCAGTTGA AGAGAACACA TGAAGAAGAG GATGATTTTG
```

```
59801  GAACCATGCA AGTGGCGACT GCACAGAATG GCTGACTTGA AGAGCAACAT
59851  CATAGAGTGT GAATTTCTAT TTGGGAAGGA GAAAATACAA GAGAAAATTA
59901  TAATGTAAAA TGGTAAAAAC ATAAGTAGTT TTTTTTTCAA TTACATGTTG
59951  CTTCCAGACA TACTTCTCTG CAACTTGTTG AGCAACATTT TAAGATGTTG
60001  GACTTCTGCA ATAGATGACA CTGATGGTTT TACTCCTTTT TTTAAAAACA
60051  CATGCGCGCG CACACACACA TGCTTTACAA GTTTTATTAT AAACCAAGAA
60101  TTTTGGACTT GCAAAGAGGT ATTATTGCAA TAATGCACTT TTCATACTTG
60151  AAATTTATTT GTATGATATA AAGTTATTAC TTTAAACAAA ATGCAAGTAT
60201  GGGGGGATTG TTTATAAAGT TTGGGTAATT TATAACAAAA TTTGCTAAGG
60251  TTTGCTAAAA ATTCATTTTT CTGTTCTATA TATTACATTT TTAACATAAT
60301  TTTACAGTTC AATTTTATGA TGGAGCCTCT TACAGAAACA TTAACAAAAT
60351  GCAGGAATCT GCCACATTTC TTTTTTAGTA TAACTTAATA GCTTAATTAC
60401  CATTTTATTT TTTATACTTC TTCCATTATT AATCTTTAAA TCATGATCCT
60451  AATTAGCTGT CCTTACTTTA ACTGATCTA ATTATTGCTT CCTTTCTTAT
60501  TACTTTCCTA ATTTTCTAT ATTTTAAAAA CTACAGTTTC CATGATAAAA
60551  GGAAAACGTT TTGATTTATA GTACCAAGTG CTTAAACACA AGGATAGTGT
60601  TAGATTTTCG AGTGACTTTC CTTTTTGCAT TTTTTGGCAG TAAAAGCCAA
60651  ACGTTGTATT TGTTCTTTTC AGAGTTGTCC AGCCCTTTTT TCCTTTGTCC
60701  AAAATGATTC TAAATAGAAT CTAATAAACC AATGTAGCAT TATTTTTTTC
60751  TAAATGAAGC CCCAAAAAAG AAAAGTGCCT TGCATCATTT AAAAAAAATA
60801  ATTAAATCCT CATGGCCTCT AAATTAGTAT GTAGAACACT GAAAAGTTCT
60851  TAACATTTTT GTGTAATTTC CTTTCTTTTT AAACCATAAA TTAGTTTAAA
60901  CTGAAAGTAC GAGGCTGGAA GAAATATTAG TAAATTATTT GGAATATAGA
60951  ATGTTTACTC TTTCTTTTTA TGTTGTCTTA ATGATTCTGT GAGATTGTTC
61001  CGGCTCAAAC AGAAGCTTTT CTTTGGGGAA GGTGATTTGT GGGAGACTCT
61051  AGTGTATTTT AAATTAGCAT TTTAATCCAT TCTTGACATT CAGTTAGTCC
61101  AGATCTGCCC CATAATTTGC TTTAGTAAAG TCACTTTATG GATTTTGGC
61151  TATGTTTTAG TTTGTGTGTA TAAAAGTTCT AAGAAAACAT TTTTGCTATT
61201  TTAAGTATGT AAGGGAAGAG AGGAGTGTTT TTAACTTTTT ATAGTTGATG
61251  ACTTTAGGGG TAGCACAAAC AAAACTCCTT TGTATCTAAC TTTTCTCAAT
61301  CCTCTCTTGA GGTGCTTTAC TAATGGGAAT GATTTCTGTA TGTTCCCTTG
61351  GTACCCAAGA GGTACTATGC AAAGTAACCT ATTACACCAA GTTACTTGCT
61401  TTGCTTTCCT CTCTATGATG TGATAATACA GTAAAAGCTT TCTTACCCAG
61451  CATAGTGGGA GAGTGGAGAT TAATTAAAAT TGTTAATTAA GAGTTAATTC
61501  CTATTGACCC AGGTGATATT TCTCTTCTGA TTTCCCTCCC CTTCCCTTCT
61551  CTTATCTTAC CACTGTGAAA ACAGCATATT GTTAATCTCG TTGTCGTCCA
61601  GTATTCTGCT TTGTGATTAG GTCTTTTGAT GTACAGTGGT CTAGTGGAGT
61651  CAAGATCGC ATTGGGTTTT CTAAAATTCC AGTTGATAAA AGTTCCAGAT
61701  AACACAGCTT TCCTGTATAT AGATCACTAT TGGGCAGGTC AGCAAAGATC
61751  TCTTACAGTG TAATAATAAT CTATGATGCT TCATTTAGCA GAAACTCTGC
61801  TTAAAAGAAT CTTCATAATA GTAAGTTTAG GTTTTAAAAA CTTGTTTCAT
61851  AAATATACAT ATATCCTCTC TAGTAGTCTG GCCAAAAGAA CAGATTTTGT
61901  TATTGATAAT TTGTAGCTGG TAATTTTCCA CATTTTCTAT CCACTGTAAT
61951  TTTTATGTTG TCACTGAAGT GCCTGCCCAG TACTGTATAT TACAGTCTCT
62001  CACAAACACT GGGAAAAGGG ACTGTCATCA TCTTGAGTAC TCTGTGTGTA
62051  TATATATATA TATAGATAGA TAGATTTTTT TTTTTTTTTT GAGACAGAGT
62101  CTCTAATGTC ACCCAGGCTG GAGTACAGTG GCACAATCTT GGCTCACTGC
62151  AACCTCCACC TCCTGGGTTC AAGTGATTTT CCTGCCTCAG CCTCCCAAGT
62201  AGCTGGGGTT AGAGGCACAT GCCACCATGC CTGGCTAATT TTTGTAGTTT
62251  TAGTAGAGAT GGGGTTTCAC CATGTTGGCC AGGCTGGTCT CAAACTCCTG
62301  ACCTCAAGTG ATCCACCCAC CTCGGCCTCC CAAAGTGCTG GGATTACAGG
62351  CGTGAGCCAC TGCGCCTGGC TGAGTACAAT ATTAATGTAG ACAAACCATG
62401  AAGTTTATTA TTTCATATAA GAACATTACA GGTTTGTTTT TCTTGCATG
62451  TCTGTCCACC TAATGTTTAA GTAGTTCTGG TAGCTCTTCC TATTCTTTAT
62501  TCTATTTGAT TCCATTTCTG TGATTCTTTT ATTACCACTG ATGTTTTGTG
62551  ATAGTTAACT ATGATAAATT TAACTGATCA TGATTTATCT TCTAGATGAT
62601  TTAAATAATG TATGAGTGAC CACCCAATTC CAACATTAAA AGTGTAATCT
62651  GGGCCCATAA TTTATAGTGA AATTGTATCA AAACATAGGG AAACTGTATT
62701  ACTGTCCATT TTGAAAATAT GAAACTTGAG TATTGAAAAT ATTCAAACAT
62751  GGAATGGCAG TATTCTAATT TCAGTTAGTT GGTTCATGTT AATTTCTTAC
62801  CTGTTAGATG TTTAAACTGC AGTGACCTTT ACTTGTATCT ACTCTGTGGT
62851  GGAAATGTTA AACCATGATA GCTTTTGCTA CCAACTCAAC CACTTAACTT
62901  TTAGAGCAGT TTTGGGGAGA GTTTATGCTT CATCTGAGTT TAGAAGTAAT
```

```
62951  GTCAGAAAAT GTTAAGCATG TCTGTATTAA GAAAATATAA GGTTTCTAAT
63001  TGTCTTATTA ATATGGTAAT TCAAGTGAAT TAGAAATATT TAACTGCAAT
63051  CTTGAATTAT AAAGTTGAGA TATATATATA TATGTATCAA GATCTCAACT
63101  TGATGTAAAG TAAATGAGCA GTTACCTGGC GGATTTTTTT TTTTTTAAAT
63151  AACTGATTTA ATCCATAATC CCATAACAAA CATAGCTTCA CCTCAGTATT
63201  TTCTTTCTTT CTTTGTTCAA CAGTGCTCCG ATAAGGGAAT GCTAGAAAAT
63251  AGATGAGAAG TACTGAAAGA CCTTTTTTTT TAATTGATTA GAAAAGTAAG
63301  TCTCTAGGGT CTTTGAATGC TGGAATTTTT TTTTTTTTTT TTGTCTTTCC
63351  CATCTGTGGC AGCTAAAACA AAAATCACTC AAAATATTCA GGTTTACATG
63401  TTAGCTCTCT CTCATAGGGA GCTGCCATAC CTCACAGTTC AAAGTGTATT
63451  CTATAGATCA GTAACATTAT ACTGACATGT AATTGCAATT TACTATGCAG
63501  CAAAAATGAT TCAAGAAGAA AAATAACCTA CAGTGTCTGT ATACCTTTGT
63551  ATACACAATT GCTTAAGTTA CTCTGCTTTT AACATTGTA CTTGGATAAA
63601  ATGCTTATGT CTGTATAGGA ATGTCACAGT GCAAGATGCT GCTAGCCCAG
63651  GCACAAAGTA TTAAAATTAT TTTGTGAAGA TTGGTGGTTG TATTAAAACT
63701  GCTGTGCCAT TATACCTCCA AAATATTGAA AAGCTCATTC ATACTGCTGC
63751  TTATACCTCA AAACTTCTTT ACTTAGATTG TTATCTGCTG GGTAAAAGTA
63801  ACCCAAATTT ACTCTGAGTT AAGAAGAGTG GATGAACATT GAATGTTGAG
63851  AAGCACTTAA GAGTATACTC TAAAACACTG TGGTTACACA CACACACAAA
63901  ATTATGGTCT GTAGTCCAGG CAAGCCTCAA ATTCCAGCTC AAGTTTATTT
63951  TTAAGGATTA GTTGAGCAAG TTTGGAGTTG GAAGTGAGAG AATCGTGTTT
64001  AAAGGAAAGG GTAGGTCATC CACAGAACAG CTTTCAGTCA TTACAAAAAA
64051  AAAATACTTC TTGCTTTTAT ATTACCATCT TCCCCCATTA GGCCTACCTG
64101  CATACTGTGC TTCATCAAAT CTAAGATCAC CTCACAACTA TACCATTATT
64151  TTAGGCACCA CTAAAAGACA GTGTATTGCT AACAAAACTA TGATAAACCA
64201  TTGATAATAT ATCCAGATTT CAGAGATGTT ACAGTGCATC TTAGTTGATG
64251  AAACAAAAAT ATACAAACA TGAGACACAG TAAAAATGAT AAGTACCACC
64301  TCATTATACC TTTTCACAAG CAAATAGTGG CCAAAGATGT GAACGGCCAG
64351  ACACGGTAGC CGACATATGT AATCCCAGAT ACTCTGGAGG CTGAGGCAGA
64401  GGATCACTTG AGCTCAGGAG TTTGAGACCG GCTTGGGCAA TATAGTAAGA
64451  CCCCACAGAA AAATGTAAAG CCAGGTGTGA TGGCACACAC CTGTAGTTCC
64501  AGCTACTGGG GAGGCTGAGC CAGGAGGGAT GGCTTGAACC CAGGAACTGG
64551  AGGATGCAGT GAGCTATGAT CACACCACTG GACTCCAGCC TGGGTGATGG
64601  AGTGGGACAG TGTCTCTTTA AAAAATGTGG GCCAGGTGCA GTGGCTCGCA
64651  CCTGTCATCC AAGCACTTTG GGAGGCTGAG GTGGGAGGAT CACTTGAGCC
64701  TAGGAGTTAA GAGACCAGCC TGGGCAACAT AGACTCCACA CAAAAAATTT
64751  TTTTAATTAG CTGGGTGTGG TGGCATGCAC CTATAGTCCC AGCCACATGG
64801  GAGGCTGAGG TGGAAGGATC ATTTGAGCCC AGGAGATTGA AGCGGCAGTG
64851  TGTGGTGATT GTGCCCCTGC GCTCTAGCCT GGGCAACAGC GAGACCTTGT
64901  CTCAACAACA ACAACAACAA AAGGCTATCT ATTGTGGGTA CACTGCCTAT
64951  GGGGTAGTCC TGCTCCACAA GGAGCAGTTT TTAAAAAAAA AAAGTTTAAG
65001  AAGTGTTTTA TGTAGCACTT TTTTCATATT TACATTTACT CACCATATGG
65051  CTTCAAAAAT CATAAACATA CTCAACTAAA ATTACAGATC ACCATTGTCC
65101  TCAATGACAC AATTTTTGTA TGGTGTACCT TACCTGTAAT TCTATTTCCT
65151  ATGGGAGGAT TTAAGAGATA TCTTAGGAAC ACTATTTAAA GGGATTTACT
65201  GAAGTGCCAA CCTTGTGAAT GATTTTACCT CAAATTGTTC AGTGGTAAGA
65251  AAGGTAATAA AGCATTAGT TGTGCCTTTA AGTAGGCTAA TTTTTTTTGT
65301  TTTGTTTTGA GATGGAGTCT CTCTCTGTCG CCAGGCTGGA GTGCAGTGGT
65351  GTGATCTCAG CTCACTGCAA CCTTTGCCTC CCGGGTTCAA GCGATTCTCT
65401  CGCCTCAGCT TCCTGAGTAG CTGGGATTAC AGGCGCATGC CACCACGTCT
65451  GGCTAATTTT TCTTTTTTTT AGTAGAGACA GGGTTTCACC ATTTTGGTCA
65501  GGCTGGTCTC AAACTCCTGA CCTTGTGATC TGCCCACCTC AGCCTCCCAA
65551  AGTGCTGGGA TTACAGGCGT GAGCCACTGC ACCCGGCCTT ACCAGGCTAA
65601  TTTTTAAAAA CATGCGTTTT TAATTACCAG GATTTACCTG ATAAAACTAC
65651  TCTTTGTCAA GGTTGTAGGA CTTCTGAAAA GACAGAACTA GCTTTGTTGC
65701  GTTTCACGAA GGACAGATCA GTTCGTCTGT ATAGGCTATA AGCAGGTAAG
65751  TAGTGCACTC TATTGGTGAA GGATTCTGT TGTTTTGGAA AGCCAACTAT
65801  AGCTGGCTGC ATGGAGGGAA ATCCAAAATC CAGATGACGT GGTGTGAGTC
65851  AATGGGATGA GAAACACTGG TATTTTCTTT ACAATTTCAT TTTACAAAGA
65901  GCACATTAAA CTAAAATTTT ATGAATTATG ACTTAATCTA ATAGTTCAAC
65951  AGCAGACTCA AGAAAAGCAC AGATGTGATT CTAACAGAAG ACTACTCATA
66001  TAAACAGGTT TAATGCAACA TGGAATGCAA AAGATTAGAA CCATTAAAAT
66051  ATTTAATTCT TCAACTTTAA AAAATTAAAT AAAATCAAAA TAGGATAATG
```

FIGURE 3, page 21 of 29

```
66101  ACCAGAATAG TGCCATTATA ATCACATCAA AAAGCTTCCA TTAACATTTT
66151  ATGAATTTGG CAATCTAGTA CAATACATTA AGTATTGTGT TTCACTCAAT
66201  TTTGTGATAC TCCATTTTTG AAAAAACTTA GAGGCTTCAG ATACCCATGA
66251  AAAGAAAAAA ATCAGGGTAG AAACACATAG GCTGAGGTTT GCTAATTCAC
66301  TGTTTACAGA GGACCTTAGA TGTCCCACTA TAATTGCTCT TAGGTATTTT
66351  TAACAAATGA ATAGTCATAA TTCACAGAAA AGACAAGTGG TACTTTTTAT
66401  CTACATAGAC TATACTATAT AAACTTTCAG TAAAACATTT AAATTGTTTT
66451  ACTTTTAATC TTGTCAAGTA ATTTTCATTT CTTCTACTTC AAAAGGTTGA
66501  CCAGGTTGTT TGCCTGTATT GGGATCAACG AATGTTGGAC TATACTATGT
66551  TTAGTTATAA TAACTAATTT ATCCACCCTG ACTTAATATG TGGGAAACAA
66601  TACACCCCTA AGTGTATTGA GATGTTTCTT TGAAACAAAA ATATTTAATT
66651  TTATGCATGT GATAAACAGC CTTATTCAAT GTATACTTTT TTTAAATGAG
66701  CAACACAGAT AGCAGACATA TAACTCCTTA TTACCCATAC TCTTGACTAC
66751  CAAGAAAGGA AGCCAAACTT TTAGAAAAAT ACAATGCAAG AAAAGATTCA
66801  AGTTAAAAAT ATATTCCTTT GGTTAAAAAT CATCCCCTTT ATAATATTCA
66851  TTTGTAATCT AAATTCACAG CATGTCCCAC CAGCCCAAAG TAATCTTCTA
66901  AATGTCATTA TACTTGTAGT ATTACAATGT TTTTTCAGTC CAGTATTTAT
66951  GGAGGTCACT CGGCTGCAGC AACAAAATAT TTCAACTCTA GGAAGAGTGT
67001  AGCCTTGTAG CATTAGCCCC TTTGACAATT TTCTTACAAG ATTTTTACTT
67051  TAGAAACCTC CGACACATGT AGTTTCTTC AGATACAGTA TATCCAAACT
67101  TTTTATAGAA ACCAACATTT TGTGGTAGAC ATTCAAGGGT AATCTTGTAA
67151  CAGTTCAGTT TCTTGCTTAG CAAAGTAAGG GTTGATAATA ACCTGAAATT
67201  TAAAAGGGG GTAGGGTGAG CAGATAGCAT TTATTAATAA AAATTGATTC
67251  TAGTAACAAT ATGAATTAAT GTTATAAAAC TTAAGTTTCC TTAGAAACAG
67301  GTTTAGATTA TGGCTTTTCC CACTGCATTC ATGTAAGTTG ATAAGCATTT
67351  AAATCACCAA AGCATTTTTA CTTAGAGTCA AATATACTTT TATCTAGTAA
67401  TCTCCAGCTC ACTAATAAAC AGGACAAATA CAAAACTCAC CCTAAGCCCT
67451  CTTTAAAAAT GAAATTTAAG GCTAGGTGCA GTGACTCATA CCTGTAATCC
67501  TAGCACTCTG GGAAGCCGAG GCAGGCGATC GCTAGAGCCC AGGGGTTTGA
67551  CACCAGCCTG GGAAACACGG CAAAACCCCA TCTCTACAAA ATATAAAAAT
67601  TAGTAGGGCA TGATGGCACA TGCCTAAAGT CGCAGCTACT CCAGAGGCTG
67651  AGGGGGAAG ATCACCTGAG CCCAGAGAGG TCAAGGCTGC GGTGAGTAGT
67701  GATTGTGCCA CTGCACTCCA GCCTGGGCAA CAGAGTGAGT CTCTGTCTTG
67751  AAAAAGAAAA ACGAATTTTA AGATGCATGT TAACACTAAA AACTCAACCT
67801  TTAAAAAAAA AAATGACCAA AATTATTTTG TAAAAATTCT TTATTTAAAT
67851  CTATTTAAAC AACTTCGGAG CAGTCGACAT ACCCACATAA AATGAGTACA
67901  TAATAGCTTT GCTCTTTAAT CATTTTTAAA GCTACTTTAA TATTTGTGAA
67951  GGTGTGTATC AGATTAACTC AAGATTGGTC TAATTAATAT GAAGTGGAAA
68001  CAAAGCAAGT CTACATCTAT ACAAAATTTC TTAATGAATC CAAACCCAGT
68051  ATTAAAGTGT GGATCTAAGT GCCTTAGAGG ATAAAAACTA TAAAAGATAT
68101  ACAAACTTGA AGGGTCTGCC CATGTTTGAA CAGACTAAAA AATCCTATTT
68151  TTAAAAAAAA CAAAAGACCT TGACTGAAGT ATGCCTGGCT GGTTGCAGTG
68201  GCTCATGCCT GTAATTCCAG CACTTTAGGA GGCCAAGGAT CACTTGAGTC
68251  CAGAAGTTCG AGACTAGCCA AGCAACATA GCAAAACCCT ATCTCTATAA
68301  AAAATTAGCT GGGTGCAGCG GCATGCACCT GTAGTCCCAG CTACTTGGGA
68351  GGCTGAGGCG AGAGGCTCAC TTGAGCCCCA GAAATTCAAG GCTGCAGTGA
68401  GCTGTGATCG TACCACTGTA TACTCCAGCC TGGGCAACAG AAAGAGATCC
68451  CATCTCTTAA AAAAAAAAA AAAAAAAAA AAAACATAA ATTATATAGA
68501  CTAGAACACA AGAAATCGGT CTGTTTTGTT CACTGAGGTA TTCCAAATAC
68551  CTAGAATAGC ATCTGGTACA TAAGCAGGTA TTTAATATTT GTTAATTCCT
68601  TAAAACTCAG AAGAGTTAGT GTTAAAAAGC AAGTTCTTGG GCCAGGCACA
68651  GTGGCTCCCA CCTGTAATCC CAGCACTTTG GGAGGCCAAG GCAGGAGCAC
68701  TGTTTGAGAC CAGCCTGAGC AACATGATGA GGCCCCATCT CTACAAATTT
68751  TTAAAAATTA GCCAGGTGTG GCGTGTACCT GTAGTCCCAG CTAATTGGGG
68801  GGCTGAAGAG GATTGCTTGA GCCCAGGAGG CTGAGGCTGC AGTGAGCTGA
68851  GATTGAGCCA CTGCACCTCA GCCTGGGTGA CAGAGCTGTC AAAAACAGAC
68901  CCTGTCTCAA AAACTAAAAA TTATAATAAA TAAGAACTAC AAGTTCTTAT
68951  AAAATGGCAA TAAATCAATA CCACTTATTT ATATTTATTT TAAATGATTT
69001  AGATATATAC AGTGAAGGCT GTTTCAGTAT GTATTTCTAC AACTTATGAG
69051  AATGAGAGAT CACAGAATAT TCTGTAATAG TTGAACATTT CCTTTGTTTT
69101  TAAATATGAC AGAGAAGCTG AGGCAAATCC GATTAGCCCA AAAGTTTATC
69151  TCCTACTAGG ACGAGAGCAT TACTATAAAA AGTTAGTAAT TTAAAGATGT
69201  TACTGTCTGT AAAGAAGTAT GCTTCCAATT TTCAAACTTT AAGGCAAAAT
```

FIGURE 3, page 22 of 29

```
69251  ATGTATAATA ATACTTTATT TCTTCATGAA ATTCAGTCTA AACTATTAGA
69301  GTGAGAATAA GTTCAGAATT AATGAAGCCA AAAAGAACTT CAAACAAGTA
69351  TCTTGTTAAG AAACTAAATT GGAACAAAAT TTATCCAGGG TTACCTTGTT
69401  TCTGCCTACT TACAATTTGC CAAGCTGCTT TCCTCTGCAT TCATCACTAA
69451  CAACAACATC TTCTACTCTT CCTCTCTGAA AATATTTACA ATGTTTAAAG
69501  GAGTAAGCAT TTACTTTTGT TTTTAGCTAA AACGAGTTGG TAAGAATTTA
69551  CTGATAATAA GTAGTATATT TTGTAAACTT GAACTTAACA GAAATCAAAT
69601  GCAAAAAATA TTATACAGTG AAGGCTGTTT CAGTATGTAT TTCTACAACT
69651  TATGAGAAGG AGAGATCATA GAATATTCTG TAATAGCTGA ACATTTCCTT
69701  TGTTTTTAAA TATGACAGAG AAGCTGGGGC AAATCTGATT AGCCCAAAAG
69751  TTTGTTTCCT ACTAGTATGA GAGTACTACT ATTAAAGTT AATAATTTAA
69801  AGATGTTTTT ACTTATTAGA GGAAATAGTA TGAGTCAAGT TGTGACCTAA
69851  ACTTGTTTTG GCTATGTCCC CAACCTTCCC ACCCCATTGT CTTTAAACAA
69901  ATATCAGGAT CAACATCACC AAAATGTAAC CTTTTCATGA ATATATCCAT
69951  CATTCTACTC CTTGCTTACT AGCAAGTTAT TTAGATATC CAAATAAAAT
70001  TAATGTCTAG TACAGAAACC CCACCGAAAT TCCTAAGTGT GACAGAACAC
70051  ATCCCAAGTG TTCCTACCTT ATTCTCATTG AATTAAGGTT TTCTCTCCCT
70101  CTTTTTTTAT TTACTATTTT ATGTGAGTTA TTGAGGGATG AAAGGGCACT
70151  ACATGCATTA GATGTATCAT AATTAGAACG GAATAATCTG AACCCTTTAC
70201  CATGTGGAAA CAAATTTATG CTAACGTGGT ATATTCAGAG TTGTTTTTTT
70251  TAAAGAGTA ACATTAGGGA TTTTGTGCAT TACTGCTAAG TTGTTTGGTT
70301  TCTCTATGCC TATACCAAAT TGATCCACCT TACAGAACAA TTTTAGCATA
70351  CAATTCATAC TGTTATACAT TTTCTTTCTT AAAGCTCTCA GAACACACTG
70401  GGAAAAGGGA TTTCTAAGAG GCACTGAAAA TCAATGAGAA AACAGATTTG
70451  TCTAATGGAA ACTCAAAGTC AGTTGTGCTA GAAAACAGCT GTCCATTTTA
70501  TTTATAAGCA GCACATACCT TAGCACAGGA ATGGATGAAT TTATGTTCTA
70551  TAATCAGAGT TGCCGTAGCA ACAATCTGTC CTAGAGTCAC ATCTTCTACA
70601  ACTGTAACAT AATAATCCCC AGATTTCTTC ATATGCTCAA AAGATTCTGT
70651  GGAAATTGGA TAACAAAGTG TTACATAGTA GACATTCAAT TTTATGGGGA
70701  GCCAGAAAAA TATTAGGATT AGCTGACTTA ATTACTAAAT GTTTAAAGCT
70751  GTTTTACCAT AGTAATTTAC CTTCCATTTC TAAAGAAAAT ATTACCAAGT
70801  AGTTGAAATA TCAGCAATTA GTATCAATTG GAATATAACC TACACATTCA
70851  AAATATCTGC TAGCAAAATA AAGACTAATA TAGCTATTTT AGATGAACAA
70901  CACTTAAAAT ACAAGTAAAT GGCTGATGTT GCCACTTCCA TGACTAATGA
70951  AAACTTCAAT TTCTTCATTT ACTTTAAATA GATCTCTTTA ACTTTTATAC
71001  TCAATAGATA TTCAAATATA ACCTTTGCAC ATTTTAACAA GAGCATGTTT
71051  ACATGGCTCA ATTCTAGAAT TTTTAGTCTT TTGCTTTCAA AATATTTTTA
71101  CAAAATATAT TTTAATTTTC CCTTTGTGAT GGAAAGTGTT TTGTGATAAC
71151  ATGACTTGCT CTTGTTGCT TTGAGAGCAC CTTGCAAGGA AGTAAAAACA
71201  TATCTGTTTC CAAGTAACTT TTCCAAGTCA CATAGCAAAT AGGTGCAAAG
71251  ATACTTCCCC TCAAATGGAT TTTCAGTACT ATTGCTGAAA TAACATGGTT
71301  TCTCATCTAA TTCATGTGCA TGCAAAGAAA AAATTCAGGA ATAAAAATTG
71351  AGGCTAATAG TCTCTCATAT TGGTAATTTC CTATGGGGCC TCATTCCAGA
71401  TAGAGATCTA AAATGGGAAA AAGAAATTCA GTGAATGAAA ATAAACAATG
71451  AGTAATCAGT AATGATGGTC CTCATTCTCA GGAGGGTCAA ATAGCAATTC
71501  AATACAAAAT TCCCTATTAT AAGGAAATGA AGAATTGTAA TTCCTCAGCT
71551  ATTAAATATT ACTAAATATT TAGTAATGAT AATAATACTT CATTTCCTTT
71601  ATAACAGGAA AAAGCAGTGG TAGAGCACTG GACAGAATTA AGGTTTTATT
71651  CCTCACCGTA GCAATAACTA CCTGTGATCT TGGGCAAGTC TTTGGATCTC
71701  TCTAAATTCC TATTTTCTCC TATGTCTAAA AGAAGAGGGG CAGGGGACGG
71751  GTGGACTAAC TCTTAAGATG CCTGCTAACC TTAAACTTCA ATACAAATAA
71801  ACCCCAAAAT AAATTTAAAG CGTATAGTCT TGCTTTTTTG ATTTGGTAAT
71851  GAAATTTCTG TAAATAACCA CAGTAAGGGA AATACTACAA TAAAAAAACG
71901  AAAACCTCT AGAGCTAACA CCTAGGTCCT ATGGTACAAT AATTATCTAA
71951  TAAAGTAGTC AGATAGTTTG CAAAACAAA GTTACTGGTA CATTTGGATT
72001  CTAGAACAAC TCAGCCACAT TAAACATTTG TATAAAACAG CTAATTTGTT
72051  CTTTGAATAA TTTCCAGCTA TTTGAACAAA AACAGAAGTG GCACTGAAC
72101  AGCTCTAAAC AAAAATGAAA TCATGTTTCC CTTTATTTCA GGAAAAAGAG
72151  GTTATAGTAC TTACTCATAA ATTGTTCAGG GCTGACAACT CCAGTCTCTG
72201  TTAGCTGACC CAATACCTTA AAAAACCTA GTTTTGAAAA ACAGATTTCA
72251  AATTACGAGA ATAGCAAAAG GAAGACAGTA TGAAAATAAG CAATATATTA
72301  AGCAGGTGGG CTTACAGGCA ATTATTTTTT CAGAACTTTC TATAATCTTT
72351  TAATTATTAG AATAAAGTGA ACCCTATTCT TCTATAATCA CTACATATAA
```

FIGURE 3, page 23 of 29

```
72401  CAAAAATAAC AGGTTTTACC AGTGCTTCTG CCTGCATAAG ATGTTTTAAA
72451  TAGTGCTGAC CTTAATATCC AGTATTTATA GACCCAGAAC ATACATTCTT
72501  CAATGTATTA TATTTTACAT TAAGTTCAAT GCAAAGGGTG CCAGATTTTC
72551  CCAAATATGT GATTTGGTTT TACTTAAAGG TGCAACATGG CTAAATACAA
72601  TATTCGTAAA TTAAAGTATA AGTAACACTG TTGAGATTAC ACTCTTTAAA
72651  ATTGTAATTT CTAGTGAATT TCATTAGTGT TACCGGAAAT TGATGTGAAC
72701  AGTGCACCTG GAATTTTGAA AATCTTAACT TTCCTACACT CAATAATTAG
72751  GCCAAAATTA GGCCCTTCAG GCTGTCTAGC AAAGAGATAA TTGTGAAAAG
72801  GACAAAGTTG ACTTTTAATT ACCAAAGTTT AAGGAAGTTA ACTTGGAGAA
72851  TTTAGATGTT AAAAAGAAA TAACTGTATA AAAACCCTTT CAATTTATCC
72901  AAGGAAAATT ATTTCCACCT TCATTCCCCA ACCAGCTTCT TAAGATCCCT
72951  CCTTATGTGT CATCATACAT GATAATTTAA TTTTTGTTTA TGAGAAATCT
73001  TTTTGGCTTA ATTAGGAAGG AGTGATGTTG TATTTAAGTC ATTTTAAATA
73051  TTTCACAGTA ATATTTGGTC TTAGCCATGA CACACACTCA TTGGTATTGA
73101  GTGTCCATCA CTTTAAAAAC TAAGTATTAT ACAAAAAATA GTCCAAAAGT
73151  CAAATATTTA AAAAAAATTA TCTGCATCAT AATGTTTAGA GAAAAATGGA
73201  AGGCTAACTC TAATTTTACA CAGGATTTTG TACATTACCT CTATTTAAGT
73251  CAGCAGTACA AAGAGGCCTC AAAACCAAGC CTTCTCCAGG ATGTGTTGGG
73301  GAAATGGCTG GAGAAAATGT AGCTGTATTC TGACTCCAGT CCACTTCTTT
73351  GAGTAGACTT GGGTCAAACA TAGGAGTTTC ATCAGGTTTC ATTTTTCTAG
73401  TAAGGTCTAA AATAAAAATT TGAATATTAA GTCACTTTAT TTAATAGAAG
73451  GAAAATTATG ATTGTTGAGA AAGTTAATAT AAATTAATGC AATTAGAAGC
73501  ATTCTTTAGC ACATATGCGA GATATTTTAC TGCAACCCAG CCTGAATCTA
73551  ACATTAAATT CCACAACTAC AGATAAATAG AAAAATCATG CCTACTATCA
73601  GATAAAAAAA TGGCTAAGTG ACTAAATTAG TAAGTTTTAA ACTATAAAAT
73651  CCCATTTATT ATCAAGTCTT TTTTTTTTTT TTTTTTCAG ACAGTCTCAC
73701  TCTGTTGCCC AGGCTGGAGT GCAGAGGCGT GATCCCGGCT CACTGCAACC
73751  TCTGCCTTCT GGGTCAAGT GATTCTCCTC TTTCAGCCTC CTGAGTATCT
73801  GGGATTATAG GCACGTGACA CCACGCCCGG CTAATTTTTT TGTATTTTTA
73851  ATAGAGACGG GATTTCGCCG TGTTAGCCAG GCTGGTCTCA AACTCCCGAC
73901  CTCAGGTGAT CTGCCCGCCT CGGCCTCCCA AAGTGCTGGG ATTACAGGCG
73951  TGAGCCACTG CGCCCGGCTA GTATCAGGTC TTTTAAAACA TGTTTTTCCT
74001  CTGGGTTGGT GCTACTAAAT GAATAGCTGA CTTTTCATGG GCTCTTAAAT
74051  TTTTTACATT ATGTTCTTGG ATTTTATTAT TGAGCCAAGA AGGCATCTGT
74101  TTCAACAGGA AATTGCAAGG GGAAAAAAAT TTTTTTTAAA AAAGTAATCT
74151  CTTAGTCTTA CTTGCCAATA AAGAAAACTT TCAGCTGTGC ACGGTGGCTC
74201  ACACCTGTAA TACCAACACT TTGGGAGGCC GAGGTGGGCA GATCACCTGA
74251  GGTCGGGAGT TCGAGACCAG CCTGACCAAC ATGGAGAAAC CCCCATCTCT
74301  ACTAAAAATA CAAAATTAGT CCGGGCGTGG GGTATACCG CGTGTAAACT
74351  TATTTTCCAT CTATGATGAA AAGTTAAGAA TATTCTGCCC TACAGCATAC
74401  TGTGACTTAT GAAATAAGGA ACAATTGGGG GTTAGGTTAT TGGGCAAATT
74451  GGTCTCTCAT TAAAATATGG TTTCTTTAAC TGGATATAGA AATAAGTTGG
74501  GGACTGCTTT TTTTGGATCT CTAATCCAAA AATCCAAAAC ACTCCAAAAT
74551  TTTGAAACTT TATTGAGGGG CCAACATGAT TGCCACAAGT GGAAAATTCC
74601  ACATCTGGTA TAATGGACAA AAACTTTTCC ATGCACAAAA TTATTTTAAA
74651  ATATTGGGGT AAAATATTTG GGCTATCTGG ATAAGATGTA TATGAAACAC
74701  AAATGGAATT TTGACTTTGG GTCCCATCCC CAAGATATTC TTCATTATGT
74751  ATATTGAAAA TATTCCCCAA ATCTGGAAAT ATATCCTATT TTTGAAATAC
74801  ATTATGTGTT TCCAAAACCT TGAAACATTT TTTGGGCCCA AACTTTTGGA
74851  TAAGGAATAC TCAACTTTTA ATTTGTTGGG AAGCTTGTT TTTTAAACAT
74901  TTTTGGGCTG GAAAAAAGCC CCCTGGCCCC AAATTTATCC CTTTGAATGA
74951  ATTGGTTTAT CC
```

FEATURES:
Start: 19364
Exon:      19364-19420
Intron:    19421-34110
Exon:      34111-34143
Intron:    34144-35683
Exon:      35684-35737
Intron:    35738-39940
Exon:      39941-40038
Intron:    40039-45810

FIGURE 3, page 24 of 29

```
Exon:    45811-45871
Intron:  45872-46578
Exon:    46579-46615
Intron:  46616-47002
Exon:    47003-47042
Intron:  47043-47133
Exon:    47134-47184
Intron:  47185-48943
Exon:    48944-49016
Intron:  49017-57568
Exon:    57569-57602
Intron:  57603-57761
Exon:    57762-59835
Stop:    59833
```

SNP's:

| Position | MMajor | MMinor | Context |
|---|---|---|---|
| 3114 | G | A | AGGCTGTTTGTTATATGGACCACCAGGTTGGTATTGAATTATTTCTACTCCACCAATAAG<br>ATAAATGAATTAAGGAATTAAAAAAAAAAAGACAATTTTTTTATTTTTATTTTTTTGAGA<br>CACGGTCTCACTCTGTTGCCCAGGCTGTAGTGCAGTGGCACAATCTGGGCTAACTGCAAC<br>CTCTGCCTTCCGGGCTCAAGTGATTCTCCCACCTCAGTCTCCCACGTAGCTGGGACTGCA<br>GGCGTGCATCACCATGTCTGGTTAATTTTTGTATGTTTTGTAGAGAAGCAATTTTGCCAT<br>[G,A]<br>TTGCTCAGGCTATCTCAAACTCCTGGACTCAAGCGATCTGCCCACCTTAGCCTCCCAAAA<br>TGTTGGGATTACAAGCATAAACCACTGCGCCTGGCCATAAGGTGGAAATTTGATGTGGGC<br>AGTTCCAACTTCTCCTCTCTTCAGAGTGAGAATGAGATAGGATATTTATGTCTACTGTTC<br>TTTGAGGCATGCTTAGTGCATTTGTGCCTCACAGTACATTTATCTTAACAGGCCATGTGA<br>TTCTAGTGCAACAGTCCTCAAATTGTGGTTCACAGACCCAGAGGTGCTTTCATGGACTCT |
| 4004 | - | A | TCCAGCCTGGCTGACAGAGTGAGACTCCTTCTCAAAAAAAAAAAAAAAAAAAAAAAAAATT<br>TTTTATATAAAGCAAATGTACCTATAGCATACTGCTTGACATATGTAGCCCCACAATGAC<br>ACAAAACAAAAAACTAAAATGTTGTTTGGCTCTTCCACTGTGTTGACATTTGTGCTGATG<br>GTGCAAGAGCACCATGGGTAAAATTAAATTACTTGCACTGTAGTGTGAATCAGCATTAGT<br>GGCATGAAACGGTGCTAGTTAGTAGCCATTGCGTTCTTGACTGCCACATACTTGCAGTGT<br>[-,A]<br>AAAAAAAAAAAAAAGTCAGTTTCACTATAAAGTCCTTGGTGAAACAGTAAAAATTATTAAT<br>TTTGTTAAATCTTCATCTTTGGGTAATATTTTGTGTTCTTCATGATAAAAGGGAAAATAA<br>ATATAAAGTACTGCTGCATATTGAATAAGATAGTTGTCTTTAGGAAAAGCACTTGTGCAG<br>TTATTTAAGTTGCCAGCTGAATTCATTGCTTTTTATGGAATACTATTTTTGCTTGAATGG<br>ACCATTTACAGATATGCTGTGATTATCAGACTGGTTATTGGTTATTAGTTATTGATTACT |
| 4514 | T | G | TTTTTATGGAATACTATTTTTGCTTGAATGGACCATTTACAGATATGCTGTGATTATCAG<br>ACTGGTTATTGGTTATTAGTTATTGATTACTCAAGACTGGTTTTTGGTTTATTTGGCGCAC<br>ATTTTTTCCAAAGCGAACAAATTAAGCCTGTCATGTTAAACAACTGACACCATCTATTGC<br>CATTGATAAAATATGAAATGTCAAGTGAAAATTAGAATTTTTAGAAACATATATCTGGCA<br>CTATGTGGTTGAAGCTTTTTCTTTTTTCTTTTCTTTTCTTTTTTTTTTTTTTGATAAGG<br>[T,G]<br>GTTACTCTGTTACCCAGGCTGGAGTGCAGTGGCGTGATCATCCTGGCTCGCTGCAACTTC<br>TGCCTCTTGGGCTCAGGTGATTCTTCCACCTCAGCCTCCTGAGTAGCTGGTACTACAGGT<br>GTGTGCCACCATGCCAGGCTAATTTTTGTGTTTTTAGTAGAGGCAGGGTTTTGCCATGTT<br>GCCCAGGCTGGTCTTGAATTCCTGGGCTCAAGCAACCCGCCCACCTCAGCCTCCCAAAGT<br>GCTGGGATTACAGGCATGAGCCACAATGTCCAGCCACGGCAGCTTTCTAATATATTAATA |
| 7570 | A | G | TAAATGTAAAAGAACCTTTTTCCCTCTCTTAATCTGTAATTGTGACTTGTATGAAGTAGA<br>TACCACAATGAATCAGATGTTAGTTTAACCAATTTTAATAAATAACCTTTCATGGCCGGG<br>TGTGGTGGCTCATGCCTGTAATCCCAGCACTTTGAGAGGCCAAGGTGGGCAGATCACCAG<br>GTCAGGAGATCGAGACCATCTGCCAACATGGTGAAACCCTGTCTCTACTAAAAATACAA<br>AAATTAGCTGGATGTGGTGGCACATGCCTGTAATCCCAGCTACTGAGGAGGCTGAGGCAC<br>[A,G]<br>AGAATCGCTTGAACCCAGGAGACGTAGGTTGCAGTGAGCCGAGATCACACCACTGCACTC<br>CAGCCTGGCGACAGAGCGAGACTCCGTCTCAATAAATAACCTTTCACTTTAACAAAATGA<br>GAAATGTTACACCAAAATCAAGTCTAACTTTGTCAGCATAATTCTTGCTCTTTAATTTTC<br>ATCTTAATGTTTTAAGCCACAGACTGTTATGTTCTGTTTTCTTAAATGATGGTTGTAGAG<br>GAAAAGAGTAATGCATATAAATTTCCAAATCTACTATCTTAGGTGGTCGTCGGTTTTCTG |

FIGURE 3, page 25 of 29

| | | | |
|---|---|---|---|
| 11672 | C | G | CTGGAGGAAAGGCAGAGTACATAGATGCTTATGATGACAGGTTCTTAGATAGTGCAGGAA<br>CTTGTGGAAGTGTTTTTTTCTGAATGCTTCTGTTTTCTCAGTGAAGTAGAATGCACGTTC<br>AGAATGAAGATAGGGAAGTGTTCTTAGAGATTTGAGGACAAAGGAGAAGGTATAAAGTCA<br>TTATCTATGGAAGTGAGGGATTGGACTAGGGTGCAGGCCAGTAAAACATGGCTTGTGAAC<br>CAAATTCTGCCTGCCCTGTGTTTTGGAAACACACAAAGTTTTGTTGTAACCCAAGCATG<br>[C,G]<br>TCATTTATCTGTTGTCTATGGCTGCTTTCCTACTGGAATAGCTGAGTTGAATAGTTACAA<br>CAGAAACCATATGGCTTGCAAAGCATACAGTATTTACTCTCTGGCCCTTTACATAAAAAG<br>TTTGCTGACCTCCAGACTAGGGAAATCTAGTATAATTTCCAGGCAGCCTTAAAAACTCTT<br>TAGAAGTTAATGGTCCAGAATAATGACAAATAGCTGATTGTTGAATTTCACTATCTTCAT<br>TGCCCCTGTTAGAGAGTTTTGAGCTGGAAAGACCGAACTGAACAAAGGATGTCAATGTAT |
| 11897 | A | C | ACATGGCTTGTGAACCAAATTCTGCCTGCCCTGTGTTTTGGAAACACACAAAGTTTTGT<br>TGTAACCCAAGCATGCTCATTTATCTGTTGTCTATGGCTGCTTTCCTACTGGAATAGCTG<br>AGTTGAATAGTTACAACAGAAACCATATGGCTTGCAAAGCATACAGTATTTACTCTCTGG<br>CCCTTTACATAAAAAGTTTGCTGACCTCCAGACTAGGGAAATCTAGTATAATTTCCAGGC<br>AGCCTTAAAAACTCTTTAGAAGTTAATGGTCCAGAATAATGACAAATAGCTGATTGTTGA<br>[A,C]<br>TTTCACTATCTTCATTGCCCCTGTTAGAGAGTTTTGAGCTGGAAAGACCGAACTGAACAA<br>AGGATGTCAATGTATAGGTTTCTTCCACAAATACTGAGCTCTTGCTAGATGCCAGATACT<br>GTGCTAGCCTTGGGAATTCTTGCTCTCAGGAAGCTTACAATGAACTTAAACCTGATTAAA<br>GACAATTCATGAATATATGTGTGATTTCAAATAGAGAACGACATGCCCTATATTGCCTGA<br>CCAAACGGTGCATCATCAAAGTTATTCAAACTGTAGTAGCCTGTGCTGTCTTACTTCTCT |
| 14523 | T | C | GATTAAAATTGTAGTTCTTTTTTAACTAGGTGGGACATTCACATCTGGAAACATACTGAA<br>ATTTTTATCTTCTTTTTAGACTTGAAGGCTTTTTTGTTAACATTTTTCGTAAGTTAAAAT<br>ACACTTGATTCAACTACAGTTGCCCTTCCTGTTCAGGTCCTGACATTATCTCTTTTGGAT<br>TATAATACATCTCTATTTTATTTTTTCTTTTGAGACGGAGTCTCACTCTGGCCCAGGCTG<br>GAGTGCAGTGGCATGATCACTGCTCCCTGTAGCCCAGACCTGATCATTTCTCCTTTATCT<br>[T,C]<br>CCAGTAGCTGGGACTATAGGCGTGCGCCACCACACCCAGCTAATTTTTGTATTTTTTGTA<br>GAGACGGGTTTCACCATGTTGTCCAGGCTGGTCTCAAATTCCTGGGCCCGAGTAATCCAC<br>CCACCTGGGCCTCCCAAAATGCTGGGATTACAGGCACAAGCTACCAGGCCTGGCCAGGCA<br>TCTCTTGTGCAGATTTACTTATTCACTAAAGTGATTTGGAAAATAGCCATGTGTGCAAGG<br>TTTACAAAAATAACTTACCTAGTTTCACTGTAGCTTTCTAAACAAGTTTTGAAACTTTGT |
| 16586 | C | T | AGCTTCACATTTATTCCATAGAATTATATTGTTTTTCTTATAATGAACATATATATTCATA<br>TGTGATATATAGCAGTCATGTTGTTTTATTCTCTACAGGTATGTTCGCAATTCGTGCTGA<br>TCATGATTTTGTAGTACAGGAAGACTTCATGAAAGCAGTCAGAAAAGTGGCTGATTCTAA<br>GAAGCTGGAGTCTAAATTGGACTACAAACCTGTGTAATTTACTGTAAGATTTTTGATGGC<br>TGCATGACAGATGTTGGCTTATTGTAAAAATAAAGTTAAAGAAAATAATGTATGTATTGG<br>[C,T]<br>AATGATGTCATTAAAAGTATATGAATAAAAATATGAGTAACATCATAAAAATTAGTAATT<br>CAACTTTTAAGATACAGAAGAAATTTGTATGTTTGTTAAAGTTGCATTTATTGCAGCAAG<br>TTACAAAGGGAAAGTGTTGAAGCTTTTCATATTTGCTGCGTGAGCATTTTGTAAAATATT<br>GAAAGTGGTTTGAGATAGTGGTATAAGAAAGCATTTCTTATGACTTATTTTGTATCATTT<br>GTTTTCCTCATCTAAAAAGTTGAATAAAATCTGTTTGATTCAGTTCTCCTACATATATAT |
| 16644 | T | C | TATGTGATATATAGCAGTCATGTTGTTTTATTCTCTACAGGTATGTTCGCAATTCGTGCT<br>GATCATGATTTTGTAGTACAGGAAGACTTCATGAAAGCAGTCAGAAAAGTGGCTGATTCT<br>AAGAAGCTGGAGTCTAAATTGGACTACAAACCTGTGTAATTTACTGTAAGATTTTTGATG<br>GCTGCATGACAGATGTTGGCTTATTGTAAAAATAAAGTTAAAGAAAATAATGTATGTATT<br>GGCAATGATGTCATTAAAAGTATATGAATAAAAATATGAGTAACATCATAAAAATTAGTA<br>[T,C,A]<br>TTCAACTTTTAAGATACAGAAGAAATTTGTATGTTTGTTAAAGTTGCATTTATTGCAGCA<br>AGTTACAAAGGGAAAGTGTTGAAGCTTTTCATATTTGCTGCGTGAGCATTTTGTAAAATA<br>TTGAAAGTGGTTTGAGATAGTGGTATAAGAAAGCATTTCTTATGACTTATTTTGTATCAT<br>TTGTTTTCCTCATCTAAAAAGTTGAATAAAATCTGTTTGATTCAGTTCTCCTACATATAT<br>ATTCTTGTCTTTTCTGAGTATATTTACTGTGGTCCTTTAGGTTCTTTAGCAAGTAAACTA |
| 17969 | A | G | AATAGAAAATGGAGTGGTCAAGTTAGCCATCTCATACTCAAAATTATTGTACAGTTCTAT<br>TTCTATGTGTTGGCAGTGCATTTTATGTGACAAAAAGTAGAATGTAGGGGGAGGTTTAAG<br>TCAAATATCTATGTGATCTTTTCACTTATAATTTGCATTTAGTTAAGGAGTGACTATCTT<br>GCCTTTTACCTTTGTGCTGGCGGTGGTTTTTAAAGAATCAATTTGGTGTACAAATCCTT<br>TCTTTCTTTTTTTATTTTTGATTTTTTTTGAGATGGAGTTTCGCTCTTGTTGCCCAGGCT<br>[A,G]<br>TAGTGCCATTGCACTATCTCAGCTCATTGCAACCTCCGCCTCCCGGATTTAAGCGGTTCT<br>CCTGCCTCAGCCTTCTAAGTAGCTGCGATTACTGGCATGCGCCACCACACCCAGCTAATT<br>TTTGTATTTTTAGTAGAGACGGGGTTTTTCCATGTTGGTCAGGCTGGTCTCAAACTCCCG<br>ACCTCAGGTGATCCACACGCCTCAGCCGCCCAAAGTGCTGGGATTACAGGCGTGAGCCTC<br>CGCGCCCGGCCCAAATCTTTTCACCATGGGTTTACAGGCATAACGCCACCACACCCAGGG |

FIGURE 3, page 26 of 29

| 18117 | C | T | TAATTTGCATTTAGTTAAGGAGTGACTATCTTGCCTTTTACCTTTGTGCTGGCGGTGGTT<br>TTTTAAAGAATCAATTTGGTGTACAAATCCTTTCTTTCTTTTTTTATTTTTGATTTTTTT<br>TGAGATGGAGTTTCGCTCTTGTTGCCCAGGCTATAGTGCCATTGCACTATCTCAGCTCAT<br>TGCAACCTCCGCCTCCCGGATTTAAGCGGTTCTCCTGCCTCAGCCTTCTAAGTAGCTGCG<br>ATTACTGGCATGCGCCACCACACCCAGCTAATTTTTGTATTTTTAGTAGAGACGGGGTTT<br>[C,T]<br>TCCATGTTGGTCAGGCTGGTCTCAAACTCCCGACCTCAGGTGATCCACACGCCTCAGCCG<br>CCCAAAGTGCTGGGATTACAGGCGTGAGCCTCCGCGCCCGGCCCAAATCTTTTCACCATG<br>GGTTTACAGGCATAACGCCACCACACCCAGGGAATTTTAAAATTGTTTTTTAGAGAGGGG<br>GGTCTTACTATTTTGCTCAGGCTGGCAAACTCCTTTTAAAAGATATTGAAAGCCATCTGG<br>TTTATTATTTTTATTTCAAAATATAATAATGGAAGAAATTTTACAGTATTATATACAATT |
| --- | --- | --- | --- |
| 18518 | C | A | GCCCAAATCTTTTCACCATGGGTTTACAGGCATAACGCCACCACACCCAGGGAATTTTAA<br>AATTGTTTTTTAGAGAGGGGGGTCTTACTATTTTGCTCAGGCTGGCAAACTCCTTTTAAA<br>AGATATTGAAAGCCATCTGGTTTATTATTTTTATTTCAAAATATAATAATGGAAGAAATT<br>TTACAGTATTATATACAATTTACTGAGTCAGCTATCAGTTCCTTTTTCTGATTTTTTTCT<br>AGTTGCCATTCTTGATATTTTCTAGGTAATCTAAACTGAGTTGTATTTTCAAGTACTCTT<br>[C,A]<br>AAATACTTTAAAAAATTTTAAATTGAGCCGTTTAATTCTTTGCTTAAAGGTGATGGGTAT<br>TTTATTTTCTGTATGGCACCACGTGATTTTAAATTGAACTCTTCATTTATTAGTCATTTG<br>GTTATAAACTCAGCATAGATTGCGCAGAATTTTGAGAGGGGAGAAACTATAGCTTTCCTT<br>TCGGATGCCACTGGTGGGTAGCCTGTTTTGCCTGTTTGTTCTTATGTTAAAGAAGGGCTC<br>TACGTCCTGTCTGGAAAGGGCGGAGCTGGCTCGGACCGCCCCACTGCCTTTCCCAGGACC |
| 19882 | G | A | TGAGTTGCTCGTCCTCTCCAGACCCCGCGGAGGGGCAGCGTCTGGTGTACTTACATTTGA<br>GAAGAGGAAAAGCAATCCCTTAGTGCCCTAGGCTTGGCATCCAGGACTGACCTGGAGTAAG<br>GTTCCTCTTTTATTGTCAAAGTAACAAGAGAGCGAAGTTGGTTTAGTCTCCTTTTGAGGA<br>ATATCTGTGGTGTAAACGATTCACTTGTGGGACACATGGCCCCACATGTGAAATAGACTC<br>GGCGCCTGAAGTTTGGAAGCGCGCCTTCGAAAAGTTTCCCAAAGTTTTTTGTTTGTTTTT<br>[G,A]<br>GACAAAGCTATGACCCGCACAACAAAGTGTCTCAAAGCTAGCTCATCTTAATCTGAGAAC<br>TCTTAATCAGAAATCTTGACCTTTGGAGGAAAATTAATATTGAAAGTAAAATACTATATA<br>CCTTTTCTCCTGGTTTCTAATTTGTGGCTATTTTTACTCCACCTTAGATCCCTGCCTGCT<br>GTTTCTACTCGGATTTTTTTCATCTGTTGCTAGTTTAACATTTTACGGCATTGCAGACT<br>ACTAAATTAGAATTTTCTGGAGGCTAAATTAACAAGACGAAGATACTCAGCTATACTTTA |
| 20988 | G | - | TAAGAGTAGAGACTTTGTTTGTGACTATCACTGTTGCAAAATGTAGTGCAGTGGTGTGAT<br>CTCGGTTCACTGCAGTCTCGAACTCCCATGCTCAAGCCATCCTTTCACCTCAGCCTCTGG<br>AGTAGCTGGGACCATGCCGGGCTAATTTTTGCTTTTTTTTTTTTGTAGCGATGGGTTTT<br>TTCTCCAGGCTGGTCTCGAACTCTTGGCCTCAAGATCCTCCCGCCTTGTCCTCCGAAAGT<br>GTTGGGATTACAGGTGTGAGCCACTGCACCTGGCCCAAGAATATACTCATGGTTTTTTTG<br>[G,-,T]<br>TTTTTTTTTTTTTTTGACACAGAGTTTCACTCTTGTTGCCCCAGGCTGGAGTGCAGTGGC<br>GCTGTCTCAGCCCACCGCAGCCTCTGCCTCGGGTCCCGGTTCAAACAGTTCTCCTGCCTA<br>AGCCTCCTGAGTAGCTGGGGATTACAGGCGCGCACCGCCAGGCCCAGCTTTTTTTTTTT<br>TTTTTTTTGAGACAGAGTCTCACTCTGTCGCCCAGGCTGGAATGATCTTGCAGTGGTCG<br>ATCTGGGCTCACTGCAAGCTCTGCCTCCCGTGTTCACGCCATTCTCCCGCCTCAGCCTCC |
| 20999 | - | T | ACTTTGTTTGTGACTATCACTGTTGCAAAATGTAGTGCAGTGGTGTGATCTCGGTTCACT<br>GCAGTCTCGAACTCCCATGCTCAAGCCATCCTTTCACCTCAGCCTCTGGAGTAGCTGGGA<br>CCATGCCGGGCTAATTTTTCTTTTTTTTTTTTTGTAGCGATGGGTTTTTTCTCCAGGCT<br>GGTCTCGAACTCTTGGCCTCAAGATCCTCCCGCCTTGTCCTCCGAAAGTGTTGGGATTAC<br>AGGTGTGAGCCACTGCACCTGGCCCAAGAATATACTCATGGTTTTTTGTTTTTTTTT<br>[-,T]<br>TTTTGACACAGAGTTTCACTCTTGTTGCCCCAGGCTGGAGTGCAGTGGCGCTGTCTCAGC<br>CCACCGCAGCCTCTGCCTCGGGTCCCGGTTCAAACAGTTCTCCTGCCTAAGCCTCCTGAG<br>TAGCTGGGATTACAGGCGCGCACCGCCAGGCCCAGCTTTTTTTTTTTTTTTTTTTGAG<br>ACAGAGTCTCACTCTGTCGCCCAGGCTGGAATGATCTTGCAGTGGTGCGATCTGGGCTCA<br>CTGCAAGCTCTGCCTCCCGTGTTCACGCCATTCTCCCGCCTCAGCCTCCCGAGTAGCTGG |
| 21465 | A | G | TTTTTTTTTTTGAGACAGAGTCTCACTCTGTCGCCCAGGCTGGAATGATCTTGCAGTGG<br>TGCGATCTGGGCTCACTGCAAGCTCTGCCTCCCGTGTTCACGCCATTCTCCCGCCTCAGC<br>CTCCCGAGTAGCTGGGACTGCAGGCACCCGCTACCACACCGGGCTAATTTTTTGTATTT<br>TTAGTAGAGACGGGGTTTCACCATATTGGCCAGGATGGTCTCAAACTCCTGACCTTGTGA<br>TCCGCCTGGCTTGGCCTCCCAAAGTGCAGGGATTACAGGCGTGAGCTACCGCGCCCGGCC<br>[A,G]<br>ATATACTCTTAGAAAACAGGAGGTCATATTTAGGCTAGTTATAAAAATGAATTTATACTT<br>AACATACAATAATGTGAATGAAGAGTATGCTTTTATTTATTTATTTATTTTTTGAGACG<br>GAGTTTCACTCTTGTTGCCCAGGCTGGAATGCAGTGGCGCGATCTCCGCTCACTGCAACC<br>TCCGCCTCCCACGTTCAAAAGATTCTCCTGCCTCAGCCGCCTGAGTAGCTGGGATTACAG<br>GCGCCCGCCACCACTCCCGTCTAATTTTTGTACTTTTAGTAGAGACGGGGTTTCACCATG |

FIGURE 3, page 27 of 29

| | | | |
|---|---|---|---|
| 21625 | C | T | GGGCTAATTTTTTTGTATTTTTAGTAGAGACGGGGTTTCACCATATTGGCCAGGATGGTC<br>TCAAACTCCTGACCTTGTGATCCGCCTGGCTTGGCCTCCCAAAGTGCAGGGATTACAGGC<br>GTGAGCTACCGCGCCCGGCCAATATACTCTTAGAAAACAGGAGGTCATATTTAGGCTAGT<br>TATAAAAATGAATTTATACTTAACATACAATAATGTGAATGAAGAGTATGCTTTTATTTA<br>TTTATTTATTTTTTTGAGACGGAGTTTCACTCTTGTTGCCCAGGCTGGAATGCAGTGGCG<br>[C,T]<br>GATCTCCGCTCACTGCAACCTCCGCCTCCCACGTTCAAAAGATTCTCCTGCCTCAGCCGC<br>CTGAGTAGCTGGGATTACAGGCGCCCGCCACCACTCCCGTCTAATTTTTGTACTTTTAGT<br>AGAGACGGGGTTTCACCATGTTGGCCCTGCTGGTCTGGAACGCCAGACCTCAAGTGATCC<br>GCCTGCCTCGGCCTCCCAAAGTGCTGGGATTACAGGCTTGAGCCACCGCGAAGGAGTATG<br>CTTTCATATCCTCAAAATGATTCAGTAATTTCAGCACTTAACTGCAAGCAACCTTACAAA |
| 26291 | C | T | ATTTTAGTATTGTGTATATAGGATTCAGCACTATCCTCAAATGTATGAACATATCCCCTG<br>TGGATAAGGGGGGACTACTGTATTTGTAAAAGTTCATATTTCATATTTCAATGCATATAA<br>GAATTATTTTATCTAATGGTTACAGTCTATATCCTTCATTGATGTGTTTATTTGAGGGTC<br>TTTGAACATTTTTGTAACTTTTCTCTATCCAAATGCAGTTTTATAGATCATTTTTATGGA<br>AAGGAAGGAGATAATTCGGAAGGATGTTTAACATGTGGTACTTTCTACCTCATGTTGAT<br>[C,T]<br>GAAAGATTTTCACTTGTGAATTAATTTGTCTCAGAATCATGGTGTTTCACAATAGAGGGT<br>TATTTTGGTTTATCTGGCTTGCCTTGGTTTGGTTAATGTGGTTGAACTGCTTGGCTACTC<br>ATAAAGTTTGGGAAATTGATTTCTACTAATTAATTACAATAGTAACTTAAAATAGATCAT<br>TGCTGGTGTATATGGAGATGCCTCCATTAATACCACGGTTTCTAAAATGATAGATTTCAGG<br>AGTAGTGTGAGCAGGCTGAGATTAAGAATTAAGTGTGATAGTGGCAAGACTTGGTTATTA |
| 28012 | T | C | AGTCAGCACCACACCCAGACAAACTGACACAAAGTATCATCTATTATTATTCTAAGGGCC<br>CATTTATCTTTCTCCAGAATTGTTCTTCTAAATTGCCTGTATACCTCTACCCCCATGCTA<br>TATAAAGGGTATATAAACTCCTAAATATCACTTTTTTTTTTTGTATACACGTTTCTTT<br>CCTGTGATACCCCCATGCACATAATGAATCTGTATACCTTTTCTCCGTTTAGTTTATTTC<br>ATAGACTGGTTTGAAATATCACGGATTTTGTTTGTTTTTGGTATACACTTTTTAAAAATA<br>[T,C]<br>CACTTTTTTTTTTTTGGTATACACTTTTCTTTCCTGTGATACTCCCATACACATAATAAA<br>TTTGTATACATTTTCTCCATTTAGTTTATTTCATAGACTGTTATCGAATCCTGATGGTAG<br>AGGGAAAGTCTTCCTTGCCTTACACAAGTATTTCCCAGAATATATTTACACCATTCCTTG<br>ATATGTGTTGCCCTGTTTTTTTTTCTTTAATTACACAAAATTTAGTGATTTCACTTTAGA<br>TAAATTCAAAAGTACGCATTTCTTTAATTGATTTTCTTCTTTATCACAGCTCTGACAAGT |
| 28030 | T | G | ACAAACTGACACAAAGTATCATCTATTATTATTCTAAGGGCCCATTTATCTTTCTCCAGA<br>ATTGTTCTTCTAAATTGCCTGTATACCTCTACCCCCATGCTATATAAAGGGTATATAAAC<br>TCCTAAATATCACTTTTTTTTTTTGTATACACGTTTCTTTCCTGTGATACCCCCATGC<br>ACATAATGAATCTGTATACCTTTTCTCCGTTTAGTTTATTTCATAGACTGGTTTGAAATA<br>TCACGGATTTTGTTTGTTTTTGGTATACACTTTTTAAAAATATCACTTTTTTTTTTTTGG<br>[T,G]<br>ATACACTTTTCTTTCCTGTGATACTCCCATACACATAATAAATTTGTATACATTTTCTCC<br>ATTTAGTTTATTTCATAGACTGTTATCGAATCCTGATGGTAGAGGGAAAGTCTTCCTTGC<br>CTTACACAAGTATTTCCCAGAATATATTTACACCATTCCTTGATATGTGTTGCCCCTGTTT<br>TTTTTCTTTAATTACACAAAATTTAGTGATTTCACTTTAGATAAATTCAAAAGTACGCA<br>TTTCTTTAATTGATTTTCTTCTTTATCACAGCTCTGACAAGTTGCTTCAGGAAGATAAGG |
| 33671 | A | C | CAGAGCCTGGCCTTTTAGTCTATTTCGATTCTTCATTTCAATTCACTATACTTTTTTTCT<br>AAGTTTTAAAATATTTTTTATCTTTTACCATTGACATTTTGTGTTGTTTTACAGCTTCTT<br>TATATTGGTCTGCATTCCAAAGACAAAATGAAGTCTCTTATGTTTTGTGATATGTGTTAA<br>AATAATTGAACTAGACAAGAATGTTAGGCCCAAGTGAGATGAAGGAAAGGCTCTTTGATA<br>AGCATTTGGCATTTTAGATCAGAGATGGCAAGTACGTATGACATAGCATTCTTCTTTTAT<br>[A,C]<br>CATTTCAGATATTATTTGTTGATCAGACACTCTTCTTCCTGTCTTGGACCACACAGTGTT<br>TTAGGTATCTGCTGTCAGTTGATCAGAGTTGGCATGAGAAACAAAAAAAAATCTATTGGCA<br>TCTCTGACTTAGAAGATCAGTTTTGGGAGAATCTTCTGGAATATCTATTCTATTCTTAAG<br>TTTAATGAGTAAATTTCATCCATTTTATGAAGTAACATAACAATTCTGGAAGCCTAGTTAT<br>TTAAAGAATGCTTTAAGCTTTGTTTCTTGTCACTTCAATTTTCAGATGTTTGTGAAACCA |
| 37703 | A | G | CCATTATCTAAAAACAACAACAAAAAATAATAATGGAGATAAACCTAAATGGATAAACTC<br>CTTTTTAAACACTCATTTACTGTTATTATTTTGTGGGAGAGGAGTGGGGTCTTGCTCTGT<br>TACCCAGGCTGGAGTACAGTGGCGCGCTCTCATAGCCTCACTGTAACCTCAAACTCCTGGG<br>CTCAAGCTGTCTTCCCACCTTAGTCTCCCAAGTAGCCAGGACTACGGGCACACACCACCA<br>TGCCTGGCTTAATTCTCAAAGTTTTTGTAGAGATGGAGTCTGGCTATGCTGGCCACATTT<br>[A,G]<br>CTTAAGTATATCTTTTTATTAAATTCAAATACAGTTTAAATAAAAGGGACAAATTTAGGG<br>CCTTTGTAATTAGTAAACGGTTTGTTTTTGTAAAGTTTTTCTACTGTTTTAAATGTGAG<br>GTAAGGTCATAATTTGCTTCATATTAGGTTGGTGCAAAAGTAATTGCAGATCTGCCTCTG<br>AAAAGTACAAATCTATTCGCTGTTACGTTAGGGCTCTATTTGATAGTTTATTTTTATT<br>TAGTAGTAGTCTATTGGGCCTTCAAAACTTGTTTAAGCATATTTATACATAATTATGTGC |

| 39269 | C | G | AACTTATTATCTGGTAATTTCTAGAATTGTCATGTTAAATTGCTTTAAGTATGGAGCCAA AAGCACTACAGGTTGAGTATCCCTAATCTGAAAAATCTGAAATGCTCCAAAGTGAAACTT TTTGAGTGTCAGCATGACAGCACAAGTGAATTCCACACCTGACCCCATGTAATGGGTCAC TGTCAAAATTTTGTTTCATGCACCAAATGACTGTATGAAATTACGTTCAGAGTATATATG GTGTGTGTGAAACATAAATGAATTTTGTGTTTAAACTTGGATACCATCCCCAAGACATCT [C,G] AGTATGTATATGCAAATATTTCAAAATCTGAAATCTGAAACACTTCTGGTCCTACCTTGG GACCAGCATTTTAGATAAGGGATACTCAACCTGTATTGAATATAATAAGATGTCATTGAA GTTGCCATTTTTAACTTCAGGAAAATTTTTAAATGGTAAAAGGTTAATTAGATTCTGTGA AGTATGTAAATTAATTCTGACTCTTAAAGTATACTGGGAGAGGCAAGGAGTTGTCTAGAG ATTTGGGTTCCAGTACTGCTGTTAACTAGGTCGGTGATGTCCAAGTATTTGGTAATGTAA |

```
POSITION      Allele 1    Allele 2
3114          G           A           Beyond ORF (5')
4004          -           A           Beyond ORF (5')
4514          T           G           Beyond ORF (5')
7570          A           G           Beyond ORF (5')
11672         C           G           Beyond ORF (5')
11897         A           C           Beyond ORF (5')
14523         T           C           Beyond ORF (5')
16586         C           T           Beyond ORF (5')
16644         T           C           Beyond ORF (5')
17969         A           G           Beyond ORF (5')
18117         C           T           Beyond ORF (5')
18518         C           A           Beyond ORF (5')
19882         G           A           Intron
20988         G           -           Intron
20999         -           T           Intron
21465         A           G           Intron
21625         C           T           Intron
26291         C           T           Intron
28012         T           C           Intron
28030         T           G           Intron
33671         A           C           Intron
37703         A           G           Intron
39269         C           G           Intron
```

Map:
Bac accession number: AL139317.2
Human chromosome 14

FIGURE 3, page 29 of 29

SEQUENCE LISTING

<160> NUMBER OF SEQ ID NOS: 3

<210> SEQ ID NO 1
<211> LENGTH: 1218
<212> TYPE: DNA
<213> ORGANISM: Homo sapien

<400> SEQUENCE: 1

```
aacaccacgc gtccggcagc ggcatggcgg ccgggtgtaa gacgcccgac cctcctcttc      60
cctgtcttcg ccgccgccgc tgctggagtc actgggaccc tgtagtctgc gtgtgttagt     120
tgtaatcccg ccgccctcct gtcagccctc cgctccgccg gccctccttc cttccgccgc     180
cgcagccagc ccgagggtcg gccggctgtg taacactctc ccacccacc caccagcccg      240 cgggccagca ccatggagga cgtgaagctg gagttccctt ccttccaca gtgcaaggaa      300 gacgccgagg agtggaccta ccctatgaga cgagagatgc aggaaatttt acctggattg     360
ttcttaggcc catattcatc tgctatgaaa agcaagctac ctgtactaca gaaacatgga     420
ataacccata taatatgcat acgacaaaat attgaagcaa actttattaa accaaacttt     480
cagcagttat ttagatattt agtcctggat attgcagata atccagttga aaatataata     540
cgttttttcc ctatgactaa ggaatttatt gatgggagct tacaaatggg aggaaaagtt     600
cttgtgcatg gaaatgcagg gatctccaga agtgcagcct ttgttattgc atacattatg     660
gaaacatttg gaatgaagta cagagatgct tttgcttatg ttcaagaaag aagattttgt     720
attaatccta atgctggatt tgtccatcaa cttcaggaat atgaagccat ctacctagca     780
aaattaacaa tacagatgat gtcaccactc cagatagaaa ggtcattatc tgttcattct     840
ggtaccacag gcagtttgaa gagaacacat gaagaagagg atgattttgg aaccatgcaa     900
gtggcgactg cacagaatgg ctgacttgaa gagcaacatc atagagtgtg aatttctatt     960
tgggaaggag aaaatacaag agaaaattat aatgtaaaat ggtaaaaaca taagtagttt    1020 tttttttcaat tacatgttgc ttccagacat acttctctgc aacttgttga gcaacatttt    1080
aagatgttgg acttctgcaa tagatgacac tgatggtttt actccttttt tttaaaaaca    1140
catgcgcgcg cacacacaca tgctttacaa gttttattat aaaccaagaa ttttggactt    1200
gcaaaaaaaa aaaaaaaa                                                  1218
```

<210> SEQ ID NO 2
<211> LENGTH: 223
<212> TYPE: PRT

<213> ORGANISM: Homo sapien

<400> SEQUENCE: 2

```
Met Glu Asp Val Lys Leu Glu Phe Pro Ser Leu Pro Gln Cys Lys Glu
 1               5                  10                  15
Asp Ala Glu Glu Trp Thr Tyr Pro Met Arg Arg Glu Met Gln Glu Ile
            20                  25                  30
Leu Pro Gly Leu Phe Leu Gly Pro Tyr Ser Ser Ala Met Lys Ser Lys
        35                  40                  45
Leu Pro Val Leu Gln Lys His Gly Ile Thr His Ile Ile Cys Ile Arg
    50                  55                  60
Gln Asn Ile Glu Ala Asn Phe Ile Lys Pro Asn Phe Gln Gln Leu Phe
65                  70                  75                  80
Arg Tyr Leu Val Leu Asp Ile Ala Asp Asn Pro Val Glu Asn Ile Ile
                85                  90                  95
Arg Phe Phe Pro Met Thr Lys Glu Phe Ile Asp Gly Ser Leu Gln Met
            100                 105                 110
Gly Gly Lys Val Leu Val His Gly Asn Ala Gly Ile Ser Arg Ser Ala
        115                 120                 125
Ala Phe Val Ile Ala Tyr Ile Met Glu Thr Phe Gly Met Lys Tyr Arg
    130                 135                 140
Asp Ala Phe Ala Tyr Val Gln Glu Arg Arg Phe Cys Ile Asn Pro Asn
145                 150                 155                 160
Ala Gly Phe Val His Gln Leu Gln Glu Tyr Glu Ala Ile Tyr Leu Ala
                165                 170                 175
Lys Leu Thr Ile Gln Met Met Ser Pro Leu Gln Ile Glu Arg Ser Leu
            180                 185                 190
Ser Val His Ser Gly Thr Thr Gly Ser Leu Lys Arg Thr His Glu Glu
        195                 200                 205
Glu Asp Asp Phe Gly Thr Met Gln Val Ala Thr Ala Gln Asn Gly
    210                 215                 220
```

<210> SEQ ID NO 3
<211> LENGTH: 74962
<212> TYPE: DNA
<213> ORGANISM: Homo sapien
<220> FEATURE:
<221> NAME/KEY: misc_feature
<222> LOCATION: (1)...(74962)
<223> OTHER INFORMATION: n = A,T,C or G

<400> SEQUENCE: 3

| | | | | |
|---|---|---|---|---|
| ttgaaatcca | aaaatatctg | aagctacatt | tggacccctg | taaataatgt | aatgtataag | 60 |
| gatttttcca | aaataagtct | taatttcagt | tttcatatat | caacaaaaag | gtactattag | 120 |
| gagtacatag | ttgccacact | tgagacatat | tccaaatgca | tacacctaac | ggtactacta | 180 |
| ttacagaaca | gcacattcta | atccacatat | acacgagttt | taattaaatt | tagcactatg | 240 |
| tctataatca | gaatgaatac | ctggaataca | tgtttctagc | aggaatattt | gttagcagct | 300 |
| ttaaggtact | tgaaatcacc | ataatcattt | ctattttaaa | tttaaatttc | actactgggg | 360 |
| taaattccat | gagggaaggt | tgtggctatg | aattttatt | tattcttttt | cttttgtggt | 420 |
| aaatatggag | aacttaccaa | atctcttata | tagcctggct | gtagatggca | atgcgaggaa | 480 |
| agaaaaagga | agcagaaaga | aaaaaaaagg | caatcagaaa | aaatggcaac | gaagcaaaga | 540 |
| aaaagttgcg | gtcacctgca | aaccaaaatt | ccagccaaaa | gtcatgcaaa | aaactacttt | 600 |
| aggtagaaac | caagcaaagt | aaatgcaaga | atgaaaaatg | aaaatgagga | agcagcaatt | 660 |

-continued

```
actttccatt tagaacactg agaaacactc cacattattt tagaatgtta aatgttgcta      720
aagaacctaa gggtagaaat ttgtagggag aagataaaaa gagcaaatat ttctttcccc      780
ctacatcgtg tacccagtta catcgtgtac ccagttctca ccggttaagg taaagccaat      840
tattttagta gcaaaataaa agtatccaaa agcctttaaa gtcttctcag atttagtcag      900
ataatatgat ccatgcactg cttttcagaa ataagaattt gaaggcataa aataagtgca      960
gtgcccatct gtttcttttt ttacacaaga aaagcaaacc cctcagttac catgtgtttt     1020
ttgcatcctt tttcctggaa gggaaaacaa agagatgccg tatactacat gaggaatttc     1080
ggctttatgg cattagtcat ttccatttag attaacataa atcaacatat agaataattc     1140
ttcaaaattt aaaaatccag tttgagagtc atatttattt aaaaataccc acagcatgtt     1200
tagttaatat atatataatt gaagggaatt aaagtaggtt aaatacaaca ggttattttg     1260
atagacccaa aagaaaacta cgagtctatg cccaggtagg gaagaatgtc cttgtggcct     1320
gcacatcttc ctacagcctc cagaacgcaa ctggatacag cttaataatt actgagcact     1380
atgtccagtg tgactagtgt ggtatctgac acacagtagc aactaaactt ctgaatgtca     1440
ctacttacta ggcaccaggg caataacatc atggtcgcta ttctctggaa acaatttttt     1500
tttctgacac ggagtttcac tcttgttgcc caggctggag tgcaatggcg ccatcttggc     1560
tcactgcaac ctccacctcc caggtacagg tgattctcct gcctcagcct cccaagtagc     1620
tggcattata ggcgtgcacc accatgcctg gctaattttt gtagttttag tagagatggg     1680
gtttcaccat gttggccagg ctggtctcga actcctgacc tcaggtgttc cactcacctc     1740
ggcctcccta agtgctggga ttacaggtgt gagccaccgc acctagccca acacaactat     1800
tcaatagaaa tttctctctc ggtcaggcat ggtggctcac gcctgtaatc ccagcactct     1860
gggaggctga ggtgggtgga tcatctgagg tcaggagttc aagaccagcc tgccaataca     1920
gtgaaacccc atctcttcta aaagtacaaa aattagccag gtgtggtggt ggcgcctgta     1980
gtcccagcta ctcaggaggc tgagacagga gaatctcttg tacccgggag gcagaggttg     2040
caatgagcca agatcatgcc attgcactcc agcctgggca acagactctg tctcaaaaaa     2100
aaagaaattt ctctcttaag ttactggtac tataagtaat ttaaattgga ctttcagatc     2160
ttcaatttct ctagtctcta ctttcttcc ttgaatcagt cttgagagca gaacatactg      2220
ttctttaaaa gctgccgtgg caaaatgcca acagataaaa attgtatata ccttttctct     2280
tggtatgttg tcaaatccat cccccatttt agaattattt tgtgttgtat tttcaaatgc     2340
aaactagtat agatcttttg agttgtgttt tttgtttata tgttcatttg acttaactga     2400 ttttttttgtg gtataatttt tcattgaggt ataattcat taaaaaaatg tagattctta     2460
agtgtacatt tcaaatatgt ttggacaagt tatatatctg tgtaaccatc accccaatca     2520
agtgtgtggt ttatttaaaa aacattattt gaaatttttt agatttaaga gatcttaaat     2580
ctacctggag caaaacctct taatataaat ggttttacct agcatggaag tctaggtcta     2640
ttaagaatta tgatgtgtac acctaactaa ggtgatattt gacttagagt atttgaaagt     2700
acattaaaaa tcttgactaa cttttttaaga aagatttaac ttcttttcta ggtgatagaa     2760
ttacctctta caaacccaga gttatttcag cgtgtaggaa taatacctcc aaaaggctgt     2820
ttgttatatg gaccaccagg ttggtattga attatttcta ctccaccaat aagataaatg     2880
aattaaggaa ttaaaaaaaa aaagacaatt ttttatttt tatttttttg agacacggtc      2940
tcactctgtt gcccaggctg tagtgcagtg gcacaatctg ggctaactgc aacctctgcc     3000
```

```
ttccgggctc aagtgattct cccacctcag tctcccacgt agctgggact gcaggcgtgc   3060
atcaccatgt ctggttaatt tttgtatgtt ttgtagagaa gcaattttgc catgttgctc   3120
aggctatctc aaactcctgg actcaagcga tctgcccacc ttagcctccc aaaatgttgg   3180
gattacaagc ataaccact gcgcctggcc ataaggtgga aatttgatgt gggcagttcc    3240
aacttctcct ctcttcagag tgagaatgag ataggatatt tatgtctact gttctttgag   3300
gcatgcttag tgcatttgtg cctcacagta catttatctt aacaggccat gtgattctag   3360
tgcaacagtc ctcaaattgt ggttcacaga cccagaggtg ctttcatgga ctctgtaagg   3420
tcaaaactac tttataatac tgaaatgtta agccaggcgc agtggctcac acctgtaatc   3480
ccagcacttc gggaggccga ggcaggcaga tcaccagagg tcaggagttt gagagcagcc   3540
tggccaacca acatgatgaa accctgtctc tactaaaaat acaaaaatga gccaggcgtg   3600
gtggcgtgca cctgtaatcc cagctactcg ggaagctgag gcaggagaat tgcttgaacc   3660
tgggaggcag aggttgcagt gagccgagat tgccccactg cactccagcc tggctgacag   3720
agtgagactc cttctcaaaa aaaaaaaaaa aaaaaaaaa attttttata taaagcaaat    3780
gtacctatag catactgctt gacatatgta gccccacaat gacacaaaac aaaaaactaa   3840
aatgttgttt ggctcttcca ctgtgttgac atttgtgctg atggtgcaag agcaccatgg   3900
gtaaaattaa attacttgca ctgtagtgtg aatcagcatt agtggcatga aacggtgcta   3960
gttagtagcc attgcgttct tgactgccac atacttgcag tgtaaaaaaa aaaaaaagtc   4020
agtttcacta taaagtcctt ggtgaaacag taaaaattat taattttgtt aaatcttcat   4080
ctttgggtaa tattttgtgt tcttcatgat aaaagggaaa ataaatataa agtactgctg   4140
catattgaat aagatagttg tctttaggaa aagcacttgt gcagttattt aagttgccag   4200
ctgaattcat tgcttttat ggaatactat ttttgcttga atggaccatt tacagatatg    4260
ctgtgattat cagactggtt attggttatt agttattgat tactcaagac tggttttgg    4320 ttatttggcg cacatttttt ccaaagcgaa caaattaagc ctgtcatgtt aaacaactga   4380
caccatctat tgccattgat aaaatatgaa atgtcaagtg aaaattagaa tttttagaaa   4440
catatatctg gcactatgtg gttgaagctt ttttcttttt tctttttcttt tctttttttt   4500 tttttttgata aggtgttact ctgttaccca ggctggagtg cagtggcgtg atcatcctgg   4560
ctcgctgcaa cttctgcctc ttgggctcag gtgattcttc caccctcagcc tcctgagtag   4620 ctggtactac aggtgtgtgc caccatgcca ggctaattt tgtgttttta gtagaggcag    4680
ggttttgcca tgttgcccag gctggtcttg aattcctggg ctcaagcaac ccgcccacct   4740
cagcctccca aagtgctggg attacaggca tgagccacaa tgtccagcca ggcagctttt   4800
ctaatatatt aatacttaaa gacttttctg atgagataag tggtgagaat aacaaaaatt   4860
ttttataatg tgtggtggaa aatgtcaaca tttggaagat ttgcataact caaccagtag   4920
tttccaaata atcaatgctt gatattaaaa tattcataag taaaagatcc agtcagtgca   4980
caggatagac caatgtattt taatgtaaca gaagtttctg tcatagtcca tgttgtaagt   5040
agatagctat tataaaaaag acaaaagtgt ttgcaagatg tagagaaaag agaagaacc    5100 cttgtacact actggtggga atgtaaatta gcacagccat ttttgaaaac atggaggttc   5160
ctcaaaaaac taaaaataga attaccatat gattcagcaa tcccacttct gggtttatat   5220
ctaaaggaat tgaaatcagt gtgtcagaga tagctgcact cccatgatta tttcacaata   5280
gccaagatat agaaacagcc taaaaattgc ccatcaatgg atgaatggat aaagaaaatg   5340
tggtagccgg gtgcagtggc tcatacctgt agtgccaaca ctttgggagg ccgaggcggg   5400
```

```
cggatcacct gaggtcggga gttcgagacc agcctgacca acatggagaa accccgtctc    5460
tgctgaaaat acaaaattag ctgggtgtag tagttcatgc ctgtaatccc agctactcgg    5520
gaggcagagg caggagaatc acttgaacct gggaggcaga ggttgcagtg agctgagatc    5580
atgccattgc actccagcct gggcaacaag agtgaaactc catctcaaaa aaaaaagaaa    5640
aagaaatgtg gtaaatacac acattggaat actattcagc cttaaaaaag gaaactctgt    5700
catttgtgac aatatggatg aatctagagg atgttatact aagtgaaata agccagacac    5760
agaaagacag ttaccacata atctcatttt catgtgaatt cttaaaaaat tgaactcgta    5820
gaaaccaaga gtagaatggt ggttaccaga agttgtggtg gtgtatgggg ataggggaga    5880
tgttggtcaa aggatataaa gttcacttag acaggaggaa taagttctag gtgacatatt    5940
gcatagcatg gtgactataa ttaataatgt attagctatt tcaaaattgc taaaagtaga    6000
ttttaaatgt tctaaccaca aagtaatgct aagcatgtga ggcgatggat atgttgattt    6060
gcctgattta atcattcttc aatatataca tgtatcataa tttaacccat aaatatacaa    6120
tttatttgtc aatttaaaat agattttaaa aattataaca ttttgattaa aattttaatg    6180
ttgacagcag aagtactttg gaattttttt ttttttttt ttttttgaga cagagtcttg    6240
ctctgtcacc caggctggag tgcagtggcg agattataag ctcactgcaa cccccacctc    6300
ccggattcaa gcgattctcc tgcctcagcc tccccagtag gtgggactac aggcatgtgc    6360
caccacgctc agctaatttt ttgtattttt agtagagacg gggtttcact gtgtttcgat    6420
ctcctgaccc tgtgatctgc ccgcctcagc ctcccaaagt gctgggatta caggtgtgag    6480
ccaccacacc tggccaagta ctttggaatt ttaaatgaaa attctatttta ggatttagct    6540 ttcattttgg aaaatttact tgccaaacga ttatattctt aaaaggattt taaaaatttg    6600
tttcacatag gccgggtgcg gtgggttctg cctgtaatcc cagcactttg ggaggctgaa    6660
gtggcaggat cacctgagcc caagagttca agaccagcat gcgccaacac agagagaccc    6720
cgtctctgaa aaacaaacag acaaacaaaa aacttagctg tgcgtgatgg cacatgcctg    6780
tcatcccagc tacttgggag gctgaggtgg gaaaatcgct taggtctggg aggtcaaggt    6840
tgcagtgagc tgtgatctcg ccacactccc agcctaggtg acagagtgat tgcctgtctc    6900
aaaacaaatt ttttttctacc ttaccatcta attaagactt cttttgtcat tcttaggtac    6960
gggaaaaaca ctcttggcac gagccgttgc tagccagctg gactgcaatt tcttaaaggt    7020
aaagggaaga ttatttttgta cttattgaaa tttaatttta cttgaattat cttatattta    7080
ccttactgtt tttcctttaa tcaggttgta tctagttcta ttgtagacaa gtacattggt    7140
gaaagtgctc gtttgatcag agaaatgttt aattatgcta gagatcatca accatgcatc    7200
atttttatgg atgaaataga tgctattggt aagaataaca cccttgttga aagttttagg    7260 acttttttt aaatgtaaaa gaaccttttt ccctctctta atctgtaatt gtgacttgta    7320
tgaagtagat accacaatga atcagatgtt agtttaacca attttaataa ataacctttc    7380
atggccgggt gtggtggctc atgcctgtaa tcccagcact tgagaggcc aaggtgggca    7440 gatcaccagg tcaggagatc gagaccatct ggccaacatg gtgaaaccct gtctctacta    7500
aaaatacaaa aattagctgg atgtggtggc acatgcctgt aatcccagct actgaggagg    7560
ctgaggcacg agaatcgctt gaacccagga gacgtaggtt gcagtgagcc gagatcacac    7620
cactgcactc cagcctggcg acagagcgag actccgtctc aataaataac ctttcacttt    7680
aacaaaatga gaaatgttac accaaaatca agtctaactt tgtcagcata attcttgctc    7740
```

-continued

```
tttaatttc  atcttaatgt  tttaagccac  agactgttat  gttctgtttt  cttaaatgat    7800
ggttgtagag  gaaaagagta  atgcatataa  atttccaaat  ctactatctt  aggtggtcgt    7860
cggttttctg  agggtacttc  agctgacaga  gagattcaga  gaacgttaat  ggaggtaata    7920
tttggtaaag  ggggtttata  aagaaaccaa  tgtttattaa  atgaagaact  gaacattgca    7980
tatttgatag  tcaaaatata  tagaacattt  taaatgaaat  atgaaatttg  aaaatattgt    8040
caggaacaaa  catgtttctc  tatcacaaac  tctaagcaaa  atgactactg  gaaaataagg    8100
ctatctgcca  aattccattt  ggtatacacc  tgtactattc  tgtgttttt  tgagtagatc    8160
agtcattcat  atatttaaat  tcttatgaat  gtgatcttgc  ggtagtttta  tgaagacatt    8220
ttttgtaatg  gtcatattaa  gactgttggc  aataaatgag  ctataattat  gtatgaagct    8280
gctctaaaaa  ttattttttt  ctctcacttt  attgctgaga  ctgaggcaac  taaaatagtt    8340
ttgataattg  aagaggatag  atgacagaat  gaaagaatgc  acataaagcc  ttcctccagt    8400
tttacctttc  cccactccaa  attctgtgaa  agtgatatca  agagtccaaa  tacattttcc    8460
acttcaaata  gaaactaggt  agcatgggta  atgcagtgtc  aaattctttc  tccttagaag    8520
tatttgaaaa  atcttttttc  ataaattata  cagatccgct  cagaagataa  catagcattt    8580
ggaaattata  aaatctctta  gaaaccttaa  attgagatat  ttttaaataa  cacaaatact    8640
cattttatt   caagtaacta  atatatcatc  aactaacaca  ttgtcaggac  tagctatatt    8700
tttagagagg  tttgttaaat  gcagtaaagg  tttttcattt  attcaagaaa  acttagaaa    8760
ttgaggacaa  tattttttat  gtcttttagt  atttctgtgt  acagtagaat  tatttgaaaa    8820
aataggccag  gcatggtggc  ttctgcctgt  aatcccagca  ctttgggagg  cccagctggg    8880
cagatcatga  ggtctgagca  ttgagaccag  cctgaccaac  gtagcgaaac  accatctcta    8940
gtaaagatac  aaaaattagc  tgggcgtggt  ggcgtgtgcc  tgtaatccca  gttactcagg    9000
aggctgaggc  aggagaattg  cttgaaccca  ggaggtgagg  ttgcagtggg  ctgagatcgc    9060
cccattgcac  tccagcctgg  gtgacagagc  gagagtctgt  ctccaaaaaa  aaaaaaaaa    9120
aaaagcagtc  ccagctactc  aggaggttga  ggtgggagga  ctggtcgagc  ccaggaggtg    9180
aaggttgcag  tgagcgatga  tcaggccaca  gtactccagc  ctgggtgaca  gagtgaaact    9240
ctgtctcaaa  aaaaaaaga  catcaaaata  tgcaatgttc  attatcagtt  tattatcaaa    9300
tttgtagaaa  aatctttgta  tccatttatc  ctaatataaa  tgttatgtct  gacatatcat    9360
aagcacttta  tatattggat  tttattatta  gcttttcctt  taaaaaataa  ttgatgaaat    9420
tttggacatt  ggaaattaga  tccacatagt  ttaatttcat  aattcttgac  atgatggaag    9480
ccttcagatt  tattaaaact  acctggtagc  tatagaaaga  tacatagcta  ttaaaaggta    9540
cataatctag  cttagaactt  tgaggctaga  aagtatatcc  ctttatataa  gagagagaaa    9600
aagaattcta  tcaaatgacc  attctgaaga  tagaacatat  ctatctgtag  acaatacatt    9660
tcatggcatt  agacatataa  aaggtgtgtg  ctatttttt  taatggttag  aattttgta    9720
aaatctgatt  cttaatattc  ttagttactg  aatcaaatgg  atggatttga  tactctgcat    9780
agagttaaaa  tgatcatggc  tacaaacaga  ccagatacac  tggatcctgc  tttgctgcgt    9840
ccaggaagat  tagatagaaa  aatacgtgag  ttaagattct  ttacctactg  tccatttccc    9900
tttgtgccca  tttctttttc  catacttcac  ttcaccttcc  actgtatttt  aaaaaagata    9960
aaactggact  ataaaataat  ttttatttt   cagatattga  tttgccaaat  gaacaagcaa    10020
gattagacat  actgaaaatc  catgcaggtc  ccattacaaa  gcatggtgaa  ataggtaagg    10080
aagtcatcta  ttttatatgt  atttacattt  ggtaaatgaa  gaaaaatact  tttagaaatt    10140
```

```
actgatagtt tcctaaatct ggttttaaat tcagcaaatg tggtggtttt aaattcagca    10200
aatagttatt gagcatctac tataagctag gaaccattgt aagtgttttg taagggctga    10260
caatatagca aggaacaaaa cagacaaatt tctgccatta gagaacttat attcttgtta    10320
ggaaaaaaca gataaagtta gtaaaacaaa gtataataga tgatgataag tgctatggag    10380
aaaaataaag caagaaagtg gggggcgggc atggtggctc actcctgtaa tcctaatggt    10440
tttggaggcc gaggcagaag gaccgcttga ggccaggagt ttgaggttgc agggagctat    10500
gatcatgtga ctgcactcca gtttggcaag acgctgtttc aggggaaaaa aaagaaaag    10560 ggggatagga aattagggaa gtgccaggac caggcatgag gatatgtttt taaatgacag    10620
ggaggattag cacagggaag gccttaccaa gaaggtaatt tatttttttag agacagggtc    10680 tcactcttgc ccaggctgga gtgcaatggt gtgatcccag ctcactgcaa cttctgcctc    10740
ccaagttcaa atgatcctca cacctcagcc tcctgattag ctgggactac aggcacacac    10800
caccaaccct ggcttgtttt tttgtaggga tggggtttca ccatgttgcc caggctgatc    10860
ttgaactact gggctcaagc aatctgccca cctcggccac ccaaagttct gggataacag    10920
gcgtgtgcca ctgcacccgg cctggttgtt tgtttgtttg ttttttaaat tgattcctgt    10980
taaatgctga caataggtca gataaagagt tctcagagta gacctttgga tttaactata    11040
tggaggtcat tggtaatctt gtcaaaagta gcttcttggg agtggtggag gtgaaagcct    11100
atttcagatg ggtttcagag agattgggag gagaggcatt gagtttagac atttctttta    11160
agagttctac agagggggca gaagaagtag aaggggaatg ccgatgagga gttggcagag    11220
ttttctataa gatggaagag tttatgaccc ccctgccctt tttttttttt ttttaataat    11280
gctactggga atgacctagg agaaagagaa attggcaatg ttctttcctt gaagagggat    11340
tggccctata tatatgtgta cttttatgag actggaggaa aggcagagta catagatgct    11400
tatgatgaca ggttcttaga tagtgcagga acttgtggaa gtgtttttt ctgaatgctt    11460 ctgttttctc agtgaagtag aatgcacgtt cagaatgaag atagggaagt gttcttagag    11520
atttgaggac aaaggagaag gtataaagtc attatctatg gaagtgaggg attggactag    11580
ggtgcaggcc agtaaaacat ggcttgtgaa ccaaattctg cctgccctgt gttttggaa    11640 acacacaaag ttttgttgta acccaagcat gctcatttat ctgttgtcta tggctgcttt    11700
cctactggaa tagctgagtt gaatagttac aacagaaacc atatggcttg caaagcatac    11760
agtatttact ctctggccct ttacataaaa agtttgctga cctccagact agggaaatct    11820
agtataattt ccaggcagcc ttaaaaactc tttagaagtt aatggtccag aataatgaca    11880
aatagctgat tgttgaattt cactatcttc attgcccctg ttagagagtt ttgagctgga    11940
aagaccgaac tgaacaaagg atgtcaatgt ataggtttct tccacaaata ctgagctctt    12000
gctagatgcc agatactgtg ctagccttgg gaattcttgc tctcaggaag cttacaatga    12060
acttaaacct gattaaagac aattcatgaa tatatgtgtg atttcaaata gagaacgaca    12120
tgccctatat tgcctgacca aacggtgcat catcaaagtt attcaaactg tagtagcctg    12180
tgctgtctta cttctcttcc tattctgtat cagatccatt gttgctaccc caatcctata    12240
gctctttgat tcatgtctgt tatgtgggtg gatggagaac tcactttatt actgctacca    12300
tagatctgat acttcaccac ttgaatcttg cacagaaacc agagaagcta gctaatgcat    12360
gctgtagcat ttaaaaattc catgtgatac aattatgtat gattacattt cagttttgct    12420
atactttata tttggcttgt atgattaaag taaacaaagt aaattccatt gttataattg    12480
```

```
gttttgagtg ttataggttt attcaaatcc aagatttgat tacagttttg ataagagtca   12540
cagcttaaca ggtatctgga gttcacatgt gcatagctat ttcactgtat aaaaatagat   12600
taagatattt tgagattttg gtgatatttc ctgttttttaa agtttcaggg gtgtgtctaa   12660
ttcttcttgg tgctggttta tttaacagaa gtcttagttt ttggatatta atattgtgga   12720
aagttaacag agctgatgtc tagctgatca aactcaaagt aagctcttca gtttaaattt   12780
tcgatgtggg cataaatcaa gtaaggtct aattttttaaa actaatttcc agtattttt   12840 ctaaacagat tatgaagcaa ttgtgaagct ttcggatggc tttaatggag cagatctgag   12900
aaatgtttgt actgaagcag gtaagggttt aaagtacagt tttactattg attttgattt   12960
ttaaaatttg ctgaaactgt tttgagttta tctgaaagcg gagcatagac tttgcaagga   13020
tttgggttca tgctgttctt ttaggaatcg attccaggaa ataggagaag cagggcaagt   13080
gagatggaaa gagggaaagc taatatgagg gtgcaccatt gaggtaggtg ctgtaggaaa   13140
gggaggttag atctcagaga agcatacaga atgccttcca ggatcaccca gctgaaagtt   13200
gggagactag aacattgatt taccagtact catcccccat tggatgagat ttgtccttgg   13260
tagtgttgac tcctttgcac ttctacctgc cttagggcag aatgtggaag gagaggcatg   13320
taatagaaca ctggccccct aaagtaagtc tgaggtgcta cagaattgcc taccacacct   13380
gtggctggaa ttagaatggg ccagcaccag aggtatctgc tgcaaaatga attgtgtatg   13440
ttgtctaata ctagtctgtg agcagtgttt tgaaagattg atttatgaat tatgtgatca   13500
tgccatttgt gtaaaatgta gtatttaaat ataattctct gtggattgtg tgatactatt   13560
tttttcactt ctacatggta tgtaaaaatt gtgtgatgct attttatttt ccagtaccaa   13620
gtagctttaa taccctacct agaatcattt agttttgtc ttccatacag aatctttaaa   13680
tagaaaaaat aaacttctac agtatagtta ctgactttat aggttataga ttttcttaag   13740
tattagaata tgtgatttcc tcttgctttt catatcatgt ttagccttag taaattcaac   13800
acagtgttta aagtggctgc tcagggaggg cttctcagta caggtatctt catgggtatt   13860
gggtatgctg tgagtcagta tctgcatcag atatgcaggt cagatacttc tgttcacgtc   13920
tagaaatgct gtcaatgcaa attagggtaa atcatgctca cagagcgtta tcaataaact   13980
aaactattta gaggtaaact gtcatatagc ttgaacaagt tagagtaatt tatgacattc   14040
tctttccaaa atgtaaacca gaccaaatta ttatcagaag attgctttgg ttagattgta   14100
atccaaatgc aagctgtgca gtgaacctaa aggctgttgc tatcaaaata tacgcttttt   14160
ttccttacat attcttacaa atttacccttt agttattgca aatgagctat aacttctgtg   14220
tggattaaaa ttgtagttct ttttttaacta ggtgggacat tcacatctgg aaacatactg   14280 aaattttttat cttcttttta gacttgaagg ctttttttgtt aacatttttc gtaagttaaa   14340
atacacttga ttcaactaca gttgcccttc ctgttcaggt cctgacatta tctcttttgg   14400
attataatac atctctattt tattttttct tttgagacgg agtctcactc tggcccaggc   14460
tggagtgcag tggcatgatc actgctccct gtagcccaga cctgatcatt tctcctttat   14520
ctcccagtag ctgggactat aggcgtgcgc caccacaccc agctaatttt tgtattttt   14580 gtagagacgg gtttcaccat gttgtccagg ctggtctcaa attcctgggc ccagtaatc   14640 cacccacctg ggcctcccaa aatgctggga ttacaggcac aagctaccag gcctggccag   14700
gcatctcttg tgcagatttta cttattcact aaagtgattt ggaaaatagc catgtgtgca   14760
aggtttacaa aaataactta cctagtttca ctgtagcttt ctaaacaagt tttgaaactt   14820
tgttattttt taaaaatcag tcatttccat tcacccggtt tctaggacaa catagattgt   14880
```

```
ttccttatgt agaaatctag aaaggaagta atccttgaaa tcttctatat taactccctc  14940
attttatgta agtgaaaatt caatacaggc agatcctcag tggaaatttt agaattcatt  15000
taattagtag atagcaataa acttacctgc tttagtttat catgagttag gattatctca  15060
aaatctggga cccatatcca taacacaact aatgttaaaa aaactgcata caaggaaact  15120
tttacccctt tgtcaaatac tgtttgagaa ggtacttgtc aaaagttga aggaaaaat   15180
tgagttgtga tactcaaata tgaatcaaat aaaaatacca atttgtacat aaattaggta  15240
aattttaaca catgaataat gactccgagt tttgctaaaa cccgctgttg gctttctata  15300
tgattcccta ttctcaacgt ttttgattat taacaaagaa tggctatcaa acttactcaa  15360
gatttttttt cccccataaa tgtgtgcctt ccagcaaatt gcttcctgtc aagttaagtt  15420
acgcttaaaa tgtgtatgtg ttggtagttt tgattgcttc ggttttttat gcttgttttt  15480
attaagagct acaatcagat acagggacca tttaagcctg attttatttt attttatttt  15540
tttgagacag agcctcactc tgtcacccag actggagtgc agtggtgcga tcttggctca  15600
ctgcaacctc tgcctcccgg gttcaagcga ttctcctgcc tcagcctccc aagtagctgg  15660
ggttacagat gcccactact acgcccagct aattttgtg ttttagtag aaacggggtt  15720
ttaccatgtt ggctaggctg gtctcgaact cccgacccca ggtaatccgt ccaccttggc  15780
ctcccaaagt gttgggatta caggtgtgag ccaccgtgcc cagccttgaa ccggatgtta  15840
aatattcata taatggtcat acctgttttt gttttagaac ataatcacaa caccgctatg  15900
gatttttttt tttttttttt ttttgagatg gggtctcgct ctgttgccag gctggagtgc  15960
agtgccacta tctcagctca ctgcaacctc cgcctcctgg gttcaagcca ttctcctgcc  16020
ttagcctccc gagtagctgg gactacaggc gcgcgccacc atgcccagct aattttttt   16080
ttttttgta ttttagtag agatggggtt tcaccgtgtt ggccaggatg gtcttaatct  16140
cttgacattg caatctgccc atcttggcct cctaaagtgt tgggattaca ggcgtgagcc  16200
accgcacccg gcctgtggat tttaattgaa aaagatagt ggttttagc aaattacaac  16260
tactggctca gaagtaataa atctaagctt cacatttatt ccatagaatt atattgtttt  16320
tcttataatg aacatataat tcatatgtga tatatagcag tcatgttgtt ttattctcta  16380
caggtatgtt cgcaattcgt gctgatcatg attttgtagt acaggaagac ttcatgaaag  16440
cagtcagaaa agtggctgat tctaagaagc tggagtctaa attggactac aaacctgtgt  16500
aatttactgt aagattttg atggctgcat gacagatgtt ggcttattgt aaaaataaag  16560
ttaaagaaaa taatgtatgt attggcaatg atgtcattaa aagtatatga ataaaaatat  16620
gagtaacatc ataaaaatta gtaattcaac ttttaagata cagaagaaat ttgtatgttt  16680
gttaaagttg catttattgc agcaagttac aaagggaaag tgttgaagct tttcatattt  16740
gctgcgtgag cattttgtaa atattgaaa gtggtttgag atagtggtat aagaaagcat  16800
ttcttatgac ttattttgta tcatttgttt tcctcatcta aaagttgaa taaaatctgt  16860
ttgattcagt tctcctacat atatattctt gtcttttctg agtatattta ctgtggtcct  16920
ttaggttctt tagcaagtaa actatttgat aacccagatg gattgtggat ttttgaatat  16980
tattttaaaa tagtacacat acttaatgtt cataagatca tcttcttaaa taaaacatgg  17040
atgtgtgggt atgtctgtac tcctcctttc agaaagtgtt tacatattct tcatctactg  17100
tgattaagct cattgttggt taattgaaaa tatacatgca catccataac ttttttaaga  17160
gtatgattca acgtaatatt tgctaatatg tgactgggtt ttcttggttt atgtaagacg  17220
```

```
ataggtccct gttgaggatg tgaaggtctg gaccctcttc caggaaaaat tctaacatac    17280
aattttgcgt atactataat ttcaggaaat ttattgtttc ccaagctcat ccaaggattc    17340
tttaggtatg tatggatacc tggctaagag tgtatgatgt aggggatgta ggagtgtcag    17400
aaatgttcaa aacatgattt ctgttaccta tacatgattc ttatatcatc tggcaataaa    17460
agctataaca aagtacacaa aggaatcatc attgggcatc ataattatt aaagatgctg    17520 gtgaaaagaa aagacaactt cagtttcata aacactaaag aaccaaaaat acatgaccta    17580
gctaattata caataattct tcaaattaaa aacttcctag caggatatta tgtgcctttt    17640 tataatttt agaaagatga acagttaaaa tagaaaatgg agtggtcaag ttagccatct    17700
catactcaaa attattgtac agttctattt ctatgtgttg gcagtgcatt ttatgtgaca    17760
aaaagtagaa tgtaggggga ggtttaagtc aaatatctat gtgatctttt cacttataat    17820
ttgcatttag ttaaggagtg actatcttgc cttttacctt tgtgctggcg gtggtttttt    17880
aaagaatcaa tttggtgtac aaatcctttc tttcttttt tattttgat tttttttgag     17940 atggagtttc gctcttgttg cccaggctat agtgccattg cactatctca gctcattgca    18000
acctccgcct cccggattta gcggttctc ctgcctcagc cttctaagta gctgcgatta     18060
ctggcatgcg ccaccacacc cagctaattt ttgtattttt agtagagacg ggttttttcc    18120
atgttggtca ggctggtctc aaactcccga cctcaggtga tccacacgcc tcagccgccc    18180
aaagtgctgg gattacaggc gtgagcctcc gcgcccggcc caaatctttt caccatgggt    18240
ttacaggcat aacgccacca cacccaggga attttaaaat tgtttttag agagggggt      18300 cttactattt tgctcaggct ggcaaactcc tttaaaaga tattgaaagc catctggttt     18360
attattttta tttcaaaata taataatgga agaaatttta cagtattata tacaatttac    18420
tgagtcagct atcagttcct ttttctgatt tttttctagt tgccattctt gatattttct    18480
aggtaatcta aactgagttg tattttcaag tactcttcaa atactttaaa aaattttaaa    18540
ttgagccgtt taattctttg cttaaaggtg atgggtattt tattttctgt atggcaccac    18600
gtgattttaa attgaactct tcatttatta gtcatttggt tataaactca gcatagattg    18660
cgcagaattt tgagagggga gaaactatag cttttccttc ggatgccact ggtgggtagc    18720
ctgttttgcc tgtttgttct tatgttaaag aagggctcta cgtcctgtct ggaaagggcg    18780
gagctggctc ggaccgcccc actgcctttc ccaggacctt cactcgtcct gtcccaccgc    18840
agccccgcct cctccacgcc gggtgagctg tggcctagca gcatccgagg ctccgccccc    18900
cccacccccc agcgtctgcg ctctagcgaa ggggcggagc agggcggtgg cgcgctgaca    18960
cctggcggcg gcggagggcg ggcagaaggc gagcgtgggc tgggattggc tgaggcgacg    19020
cgggtggagg gggcgggaag gaggcgggga gacgggttgt cgggctggtt cctgtgctgg    19080
atcctgggcg gcctgagggg tacggagact ctggggagg gagacggcag cggcatggcg     19140
gccgggtgta agacgcccga ccctcctctt ccctgtcttc gccgccgccg ctgctggagt    19200
cactgggacc ctctagtctg cgtgtgttag ttgtaatccc gccgccctcc tgtcagccct    19260
ccgctccgcc ggccctcctt ccttccgccg ccgcagccaa cccgagggtc ggccggctgt    19320
gtaacactct cccaccccac ccaccagccc gcgggccagc accatggagg acgtgaagct    19380
ggagttccct tcccttccac agtgcaagga agacgccgag gtgagtcgct cccgtggctg    19440
ccacgcacag gcctctccct gtggctccgg ccgaggggcg accccagtcc caaccgtct    19500 tagccgccac ctgtacgggc gccctgcctc ctaagggcgt cccgggacct ctgaagccga    19560
gcggtcggct ccaatcccca ctgagttgct cgtcctctcc agaccccgcg gaggggcagc    19620
```

-continued

```
gtctggtgta cttacatttg agaagaggaa aagcaatccc ttagtccota ggcttggcat    19680 ccaggactga cctggagtaa ggttcctctt ttattgtcaa agtaacaaga gagcgaagtt    19740
ggtttagtct ccttttgagg aatatctgtg gtgtaaacga ttcacttgtg ggacacatgg    19800
ccccacatgt gaaatagact cggcgcctga agtttggaag cgcgccttcg aaaagtttcc    19860
caaagttttt tgtttgtttt tggacaaagc tatgacccgc acaacaaagt gtctcaaagc    19920
tagctcatct taatctgaga actcttaatc agaaatcttg acctttggag gaaaattaat    19980
attgaaagta aatactata tacctttcct cctggtttct aatttgtggc tatttttact    20040
ccaccttaga tccctgcctg ctgtttctac tcggattttt tttcatctgt tgctagttta    20100
acattttacg gcattgcaga ctactaaatt agaattttct ggaggctaaa ttaacaagac    20160
gaagatactc agctatactt tagtaggatt aagaaagaaa atctaacatc gctagttaaa    20220
aataccttta aagtagttgg gaaaaataaa gccctatttt taggagacca ttcaatttat    20280
tccgaatatt tattctattg aatatcttca ttggaggttc acttttttt tttttttttt    20340 tttgagacga gtcttgctc tgtcgccagg ctggagtgca atgtggcgcg atctcggctc    20400
actgcaacct ccgccttccg ggttcaagcg attctcctgc ctcagcctcc tgagtagctg    20460
gaactacagg cgcgcaccac cacgcccagc taatttttgt gttttaggg gagacggggt    20520 tcaccatttt ggccagggtg gtctcgatct cctgaccttg tgatccgccc gactcggcct    20580
cccaaagtgc tgaaattgca ggtatgagcc accgcgcccg gcctaggttc acttttttgt    20640
ttggagggct ctcttgtggt attgatgctt gacaattaca tttgttttaa gagtagagac    20700
tttgtttgtg actatcactg ttgcaaaatg tagtgcagtg gtgtgatctc ggttcactgc    20760
agtctcgaac tcccatgctc aagccatcct ttcacctcag cctctggagt agctgggacc    20820
atgccgggct aattttcctt ttttttttttt ttgtagcgat gggttttttc tccaggctgg    20880
tctcgaactc ttggcctcaa gatcctcccg ccttgtcctc cgaaagtgtt gggattacag    20940
gtgtgagcca ctgcacctgg cccaagaata tactcatggt tttttgttt ttttttttt    21000 tttgacacag agtttcactc ttgttgcccc aggctggagt gcagtggcgc tgtctcagcc    21060
caccgcagcc tctgcctcgg gtcccggttc aaacagttct cctgcctaag cctcctgagt    21120
agctggggat tacaggcgcg caccgccagg cccagctttt tttttttttt tttttgaga    21180 cagagtctca ctctgtcgcc caggctggaa tgatcttgca gtggtgcgat ctgggctcac    21240
tgcaagctct gcctcccgtg ttcacgccat tctcccgcct cagcctcccg agtagctggg    21300
actgcaggca cccgctacca caccgggcta atttttttgt attttagta gagacggggt    21360 ttcaccatat tggccaggat ggtctcaaac tcctgacctt gtgatccgcc tggcttggcc    21420
tcccaaagtg cagggattac aggcgtgagc taccgcgccc ggccaatata ctcttagaaa    21480
acaggaggtc atatttaggc tagttataaa aatgaattta tacttaacat acaataatgt    21540
gaatgaagag tatgcttta tttatttatt tattttttg agacggagtt tcactcttgt    21600
tgcccaggct ggaatgcagt ggcgcgatct ccgctcactg caacctccgc ctcccacgtt    21660
caaaagattc tcctgcctca gccgcctgag tagctgggat tacaggcgcc cgccaccact    21720
cccgtctaat ttttgtactt ttagtagaga cggggtttca ccatgttggc cctgctggtc    21780
tggaacgcca gacctcaagt gatccgcctg cctcggcctc ccaaagtgct gggattacag    21840
gcttgagcca ccgcgaagga gtatgctttc atatcctcaa aatgattcag taatttcagc    21900
acttaactgc aagcaacctt acaaataatg tagaggagtc ccacattcca ggtgaagaaa    21960
```

-continued

```
ttgtacctta ctgaaaataa gtgatgtgcc aaattaacaa cacagtagca caagacacag   22020
aaggacctcg gcctcctaat tcattgttct ttttaataca cttcaattct tccctgccct   22080
aatcttaaaa attctagttt aaaattttcc cggactttgc atttaatctg ttactgtgta   22140
tatcattatg tatgccttat tcctgcaaaa ctgataaatt cttgctggga atatatacct   22200
gtcttttctg tgtgggactt gaaaacacac tcttttttt atgctaccag atgtgtgggg    22260 gttttttccat accaagcagt tttccagcag gcatgaactg aatgtcccat aattcaattc   22320
tgacacatat gtacctgaag ttagtcagat cccacaggtt aatgggctca gtcccgcaag   22380 gctgcccca acctcagatg gtaatcacaa gtagtaggtt gtcacctata cactcctgac    22440
tgactgtaaa tcagggttcc cgttactccc tccttggttc agttaacttg ctagagtgac   22500
ttacaggact cagggaagta catttacggg tttattataa aggatactac aaaagatcag   22560
tgaacagcca gtaggaagag atgaataggg caaggtatgg gggaaggggc acaccaccat   22620
cccagtgtca ccagtagagt catgattgca agctgtccag gttcttggcg ttttgaacaa   22680
agaattggac aaaactccaa gcaaagaaag aatgaagcaa caaaagaaca aaagcaggga   22740
tttattgaaa acaaaagtac actccacagt gtgggagctg ccctagcagc actccccccc   22800 gaccccgct gctttaccga atcttcttgg gtccaaatac cccctagaag tttcccattg    22860
gccattccat gctcacctca tgtaaatgaa gaggtggctt gcaattggtc tgattggttg   22920
ccagacccac ccccacatca gtccgcttgg ttgtggacag cgaccattca gtggctagag   22980
tgaagttaca aagttgcaaa cgaagattcc acccgcagtc agtctgattt gttgaggaca   23040
gccaatttcc cgtctactgt gcagaaaagg taggtggttt gcaacgggag tagcctctgg   23100
tccttttgtt acttaggcgt ggaaagttag ggttttccct tcaagttagt tctgggaagt   23160
cggggtgaaa cagccttaga ttccctgcct ccagaccta ttcacctgcc tcactagcac     23220
ctccagtgtt ttcatccaga agctcaacaa atcttattca acggttttta tagaacttca   23280
tctccatccc ctcccataga ggtgtgtgtg tgtgtgaggc tgagagttca accctcttgt   23340
cacatggtct ttctggtgac tggccccacc ctaaatcact tcattagcat aatcaggttt   23400
gatcaaaaat agtggctcat aaataaccaa agacactcct attagaaaat tccaagagtt   23460
ttaggaggac tgtgacagga actggagaga aagaccatgt atttcatatt atatcacagg   23520
gacagaggta atggttaaag ctagtggata atgatgcaag tattgtctgc tgaaagccaa   23580
ttcgttccgt atttcttaat attgcatgtt tggtatcttt tggttgcaag caacaaaaac    23640
gaatttaaga aaagaagaa gtaattaaat ccggccgggc gcggtggctc acgcctgtaa    23700
tcccagcact gtgggaggcc gaggcggacg gatcacgagg tcaggagatc aagaccatcc   23760
tggctaacac ggtaaaaccc cgtctctact aaaaaaaaa ttagctaggt atggtggcgg   23820
gcgcctgtag tcccagctac ttgggaggct gaggcaggag aatggcatga acccgggagg   23880
cggagcttgc agtgagccga gatctagcca ctgcactcca gcctgggaga cagagcgaga   23940
ctccatctca aaaaaaaaa aagtaattaa atccagaagg gtagtggtgc agctagtttc   24000
aaggatttga ccaaacccag gtattataaa gcatcagaac tgcctttgtc tctcatgagt   24060
tcttatctct actttctctc agagtctctg ctttctctct ggcttctcca agatgtgaag   24120
cttggccatc tggggtcaca cctttatgag cttggttatt gaggaataaa actgaacact   24180
tccagcttct gtgtttgaaa tctagaggaa ttgcccaatt taattcatgt tcccacactt   24240
tggatcagtc actgtagcca ggaaagggca gatacaatga ggggcccat ctaggtcata    24300 tccctaattc cttggctaga ggagtgaagt ttattgttgg tagccctccc accaaaacca   24360
```

```
taggaacatt tccacaggta gagggtactt tctgggctga taaaactata catagggggcc   24420 acataaataa actattaaat aggagcatat agttattcat aataaactga ctaataagca   24480
ctgttaattt tctaatctcc agtgagataa tgtaaagtgt caaatggtct taagtagtta   24540
gagtgatcag ccagcattgt ttctttgaca cagggagcac tacctggaaa tccaaattac   24600
agaccaaatt taataaaaac ggaattcaag cagagagttc agggaatgct tttaatgtta   24660
atgtgatcaa gctatgatag gttgatgatt ctgtcacctc tacaagaata ttactttcac   24720
gtttcttgaa atattggtat tctttgtata ggacagtgct aacaaaaatt tagatcagtc   24780
agtttgtgaa aagattgtta cttttttttgt ttaaaactttt ttcatgaatt tccattgttt   24840
tgaagatgaa atttaaaccc ttgacattat ttccagggtc ctgtatggtc tgacatctgc   24900
atacctctct aacctcatta tgagctactc ttcttgctcc tttctctgta agccctagcc   24960
atatttatct tctctcagtt cctggaatgc tttaatttcc accccccgcc ttcagagcct   25020
ttatgtttgc tatttttcccc tgccttggct gccagcacct tccttaccct cacctaatta   25080
actgcttacc cttgggttag atcccacttt aggcaacatt tcttcagaga gcttttcct    25140 gtttgccagt ttctctaact cctttcctca tcctctagac tggttcaatt ccccagctac   25200
tatggcactt ggtactttaa tacttacctt tgtaacattt aacaatttt ggtcattgtc    25260 tattttccat ttagactgaa cctttcataa gagagcttag atattaggaa gaaggagtag   25320
ctgatagtac caattttttaa gcaaattggt tgtagctggg gctattggtt ttataattta   25380
aaagttaatg ttttatcttc tcttctgaca gaaagtgaaa tatttatttc cattgcagtt   25440
tagcaacttt ccatgtttcc ctttccattt ttcttgtgaa tcccgtagta caggatcaaa   25500
gataggaatt atttaacata catggctgag gattcctttt ctagctcctt tatttagaat   25560
ggtgcttttt aacccttact ctagagtaag gaattttttta aaaatactga tgcctggacc   25620
ctaccagcac ctattgtagt ttaatttatc tgaatgaagc tagatgattc taatgttcag   25680
tcaggtttaa aaaattgctgg tttagaaaat atcttgagta ctcttctgcc cctccagtcc   25740
ctgcccacct tctcttttta tttgagtgaa acatttttctt ttctcctttg atttaagcaa   25800
agctcaagct tggtgtggga atgaaaggaa aaggactttg gagggattta cctatttttt    25860
ctaggagaga aagtgcaata ctaacttttc tgttttgtgg aatgtcccag tgcaagtcta   25920
gtattctgat gtttttttttc ttcccccaaac tgttgccccc cacctccagc ctatgtacaa   25980
tttgtgtttt attttagtat tgtgtatata ggattcagca ctatcctcaa atgtatgaac   26040
atatcccctg tggataaggg gggactactg tatttgtaaa agttcatatt tcatatttca   26100
atgcatataa gaattatttt atctaatggt tacagtctat atccttcatt gatgtgttta   26160
tttgagggtc tttgaacatt tttgtaactt ttctctatcc aaatgcagtt ttatagatca   26220
tttttatgga aaggaaggag ataattcgga aggatgtttt aacatgtggt actttctacc   26280
tcatgttgat cgaaagattt tcacttgtga attaatttgt ctcagaatca tggtgtttca   26340
caatagaggg ttatttttggt ttatctggct tgccttggtt tggttaatgt ggttgaactg   26400
cttggctact cataaagttt gggaaattga tttctactaa ttaattacaa tagtaactta   26460
aaatagatca ttgctggtga tatggagatg cctccattaa taccacggtt tctaaaatga   26520
tagatttcag gagtagtgtg agcaggctga gattaagaat taagtgtgat agtggcaaga   26580
cttggttatt agacgtgtgt tcagacggat gtgtggtaga agaagactat gagcattcag   26640
acttaaaatc ttggttagta agatccatag acaggcaggg ttttttttgtt tgtttgtttg   26700
```

-continued

```
ttttaacagg ttggagtgca gtggcaggat ctcaactcac tgcaagctcc gcctcccggg    26760
ttcacgccat tctcctgcct cagcctcccg agtagctggg actacaggcg cccgccacca    26820
tgcccggcta atttttttgta ttttttggtag agacggggtg tcaaccatgt tagccaggat   26880
ggtctcgatc tcctgaccct gtgatccacc ctccttggcc tcccaaagtg ctgggattac    26940
aggcgtgagc cactgtgccc ggccaacagg caggtttaag gtttgttctg taggtggtaa    27000
tctgggttag ggcagcaaag aaggtggatt ctgagatcag catctgatga taacaccagg    27060
aatagttcca aatgaacttt tctgtgagag aaagctttct aggtttcaaa ggatccatac    27120
ctattgcagt aattactaat gttctctgaa gaaggcttct tatctgtcct gtgactagga    27180 ataattttc attccctcct actatacaac ttgcttttcc ctcttataat atcttccata     27240
tatatatata tctcaagaga gtctttcatg ttgtattaca tataaccctta tggaaagctc   27300 aaaagttctt tgaagcctct tgttttgcta aaaggttcag gtaaattttg cattctatcc    27360
catatgtgcc tgtttgtttt aatataaaaa ttgtttaaat tagtaaccag tgaaaatact    27420
gtttctccct aaagaatttt tttgataaaa ttgatacttc agtggctttg agtgtctttt    27480
ggcatattgc caaatgaagg tgttgaggaa atgccactcc aaaatatgac accttgatat    27540
attgattact ttaagttgga aacacttgca aagtagcaaa tgcaaagaaa cactttctct    27600
gaactcctgt tacctaccta aggacagatc ctccaaaaga agctcaatttt gctcctaggg   27660 agtttgatca accagggaag attgtctctt atcactggag aggagagtaa aagtcagcac    27720
cacacccaga caaactgaca caaagtatca tctattatta ttctaagggc ccatttatct    27780
ttctccagaa ttgttcttct aaattgcctg tatacctcta cccccatgct atataaaggg    27840
tatataaact cctaaatatc actttttttt ttttttgtata cacgtttctt tcctgtgata    27900
cccccatgca cataatgaat ctgtatacct tttctccgtt tagtttattt catagactgg    27960
tttgaaatat cacggatttt gtttgttttt ggtatacact ttttaaaaat atcactttt    28020 ttttttttggt atacactttt ctttcctgtg atactcccat acacataata aatttgtata   28080 catttttctcc atttagtttta tttcatagac tgttatcgaa tcctgatggt agagggaaag   28140
tcttccttgc cttacacaag tatttcccag aatatattta caccattcct tgatatgtgt    28200
tgccctgttt ttttttcttt aattacacaa aatttagtga tttcactta gataaattca    28260 aaagtacgca tttcttttaat tgattttctt ctttatcaca gctctgacaa gttgcttcag    28320
gaagataagc ctggctgtta gactacttga gaatctttta aaagaaaaa agtcaataac     28380 atttagtgca gtagatctct gaaatgcatc tattttgtgc ttattctgtg tcaggcactg    28440
tgcttatcat tagggtacc atgactaaaa agagtatttg gcctaaagtc tttaaaaact     28500
gttttctttt tcctttcttt cttttttttt ttttttttt tttcgttgag atagggtctg    28560
tctctgttgc ccaggctgga gtgcaatggc accatgatga ctcactgcag cctcgacctc    28620
ccaagcccga gtgatcttcc tgcctcagcc tcccaagtag ctaggacctc agtcatgcac    28680 caccacccgca cctggctaat ttttttaattt ttgtagagat gaggtctccc tatattgccc   28740
aggctggtct tgaactcggg ctcaagctat cctcctgccc cagccttcca aagggctggg    28800
attgcaggtg tgagctacca tacctggcta aaaactcat atataaaaag attaccataa     28860
cacattggta agttaaagaa tctaggctgg gcgcggtggc tcatgcctgt aatcccagca    28920
ctttgagagg ccgaggcagg tggatcatga ggtcaggagt tcaagaccaa cctggccaag    28980
atggtgaaac cccatctcta ctaaaaatac aaaaattagc caggtttggt ggtgggcgct    29040
tgtaatccca gctactcagg aggctgaggc agataattgc ttgaacctgg gaagcggagg    29100
```

```
ttgcagtgag ctgagatcgt gccactgcat tgcactccag cctaggcgac agagcgagac    29160
tccgtctcaa aaagaaaaaa aaagtatcta gtaaacaatt acatttccct cattgctggc    29220
ttagaaatta catgctttat ttctattctg ttaatatcca taaattagtc attattttat    29280
gcagccaata tttgtttaat tgtaactgta tgtttgccgt aaagttcatt cttacattga    29340
aagactgtat agtatattga ttcagagaat gaactctggg ttcagactat ctggatccaa    29400
aatcaagtta cttaggttct ctatgactaa aatagacagt gatagtatcc cttcttcaaa    29460
gaacatttta acttttttc tttaaagata ttttttccgag catatattct taattaacag    29520 ttgttttgt cctgccacta tgaatgaatt atttgtgtcc tctggcttct gttcatgcaa     29580
ttgagaagtc agtgtccatc tgattgtcct tcctttgtgt gtaatctgtc ttttgtctag    29640
ttgatctttt ttaataaagg taaaatttat atagtgtaat gtacaaatag taagtgtgca    29700
gttcattgag ttttgatgaa catacactaa tccaccccat caagatacaa gaacattcta    29760
ttagcataga aggttacatc tatttccagg catttcctct cccattccac aataggaaac    29820
cagatttcta tcaacataga ttagttttcc ttgctcttga acttgataca aatggaatca    29880
tgcaaatgga ctcttttgtg tgtggctttc ttcactgagc ataatgtcaa tgaaattcat    29940
ccatgttgtt gtgtttatga gtacttcgta gactttatc cctgagtact actattcctt     30000
tgtatgaaga gaccatagac atttgagttc tttgagacta caataaataa agctgctata    30060
aatattcatg tataagtctt tgtgtggata tatgtttta tatatatata tattttttt      30120 tttttttggg taaagcctag gagtggaatg gctagatatt ataatagggt aggtgtatgt    30180
ttaccatttc attttacatt cccaccagca atgtgtgaga gtcccagttg ctccacatca    30240
tcaccagcat ttggtgttgt caattttttt aactttaacc attctaatgg taggtaatga    30300
tatcttttga ttttactttt gagtttcgtg tgtgtgtgta tgagagatgg agtctcactc    30360
tgtcacccag gctggagtgc agtggtgcaa tctcggctca ctgcagcttc cacctcccag    30420
attcaagcaa ctctcctgcc tcagcctccc gggtagctgg gactacaggc gtgccacctc    30480
catgcctggc taattttttat atttttagta gagacagggt ttcaccatgt tgcccaagct    30540
ggtaaacttc tgagctcaag tgatccgcct acctcagtct cccaaagtac ttggtaattt    30600
acaggtgtaa gccaccgcac ctggcctatt cactgatttt taatttcaat tatacttctt    30660
atttctacat attctgtgtt tttaaaaatc aatttcttag tctggtcata ttttgatact    30720
ctaatttctt taaattttttt atattttcg ttattgctta taatatctgc agttttgtaa    30780
gtgtaactca gttgtttctg cttcctgtgg tggctcattt cctgttttta aattagtttt    30840
tgattgtgag cttgttggga ctttatctgt gtgaattatt tctgatctag gtttaaggtg    30900 tgttttcta gagaatatgc atttgcttct tccaggaatc cagggatgca atctacccag     30960
gaccacttac attaaattct cacttggcct cacaaaagta actgaattct aaccccaaac    31020
ttgagtggat gccagattgt ggttaggaag accccactcc accactacca atacctaccc    31080
agagccaaag ctaggaagga caagagtact cacttctgtg ggatgagttg agttttttgtt   31140 tttctttctt tccctagttt atctttcact gaggatgttg cctttgggag ttctagcttt    31200
ttggtcttga tctgagttcg actttgagca gatcatagac tttgtcttat gtttacaagt    31260
acgtttccac ttaaaataag gccgtagtga agatgtagaa caactagaag tcccatacat    31320
tgctggtggg agtgtacagt ggtttttacaa aacttttggc agtatctagt aaagccaaac    31380
ataggcctac cctgtgtcaa aagacaaaat tacaacaaat ttagcttaaa aatctaactc    31440
```

-continued

| | |
|---|---|
| acttttatta gtggttcatg aatcaggcag tgtgtcatca aaagatttag aaaaggcatt | 31500 |
| tcagtgtgct gagcagagga agttgaattt ataggcaaaa tctagctaaa taaagcagaa | 31560 |
| atgaaacaaa aagtggattg gtcatttcaa agttagtttc tttatagtat aaaacacag | 31620 |
| gggacttcct tatgctggct caggataact ggcctccttc tgattgattg ctatgaatct | 31680 |
| tttgatttt tttttttttt tgagatggag tttcactgat gttgcctagg cctggagtgc | 31740 |
| aatgccacga tctcatctca ctgcaacctc cgcttccagg catcaaggga tcctcctgcc | 31800 |
| tcaccctccc acgcagctgg gattacaggc tccctccacc atgcctggct agttttgta | 31860 |
| tctttaatct agaaggaccc ccaccctgca gcccaggcga cagactgata ccccacctaa | 31920 |
| agagatccac ccgcctcatc ctcccaattt gccaggggc agactgcatt ccaccggtcc | 31980 |
| ctgatttggg tgcttaaaac tcagaatttt cttggggatt ttggtctccg acgttatcgg | 32040 |
| ggaaaactgt ttttaacctt ttattttgaa acaatttag gatctttgaa aagttgcaaa | 32100 |
| aatcctccat ggaattccat ttacccccttc ccccagtttt ttcttagnnn nnnnnnnnn | 32160 |
| nnnnnnnnnn nnnnnnnnnn nnnnnnnnnn nnnnnnggc tcccgcccca tgcctggcta | 32220 |
| attttttgtat tttagtaga gatggagttt caccatgttg gccaggctgg tctcaaattc | 32280 |
| ctaacctcag gtgatccacc cgcctcagcc tcccaaagtg ctgggattac aggtgtgagc | 32340 |
| caccgcgccc ggcttttttga tttttttaaa ctgtcattac tcgggttta tagtctacta | 32400 |
| ctatattgct gagaacagtt ttcaagatta aaaataaaaa tgttttctgt ttctcttagt | 32460 |
| taaaaaaaaa aacctgtctc tcattgtagg attattattc tctcttttca ttatagatgt | 32520 |
| atactatttc taccttctgt gttaaaaata cttttctggg ccgggggcag tagctcactc | 32580 |
| ccgaaatccc agcactttgg gaggccgagg cgggcagatc acgaggtcag gagatcaaga | 32640 |
| ccatcttggc taacacggtg aaaccccgtc tctactaaaa gcacacaaaa aaattatggc | 32700 |
| gtggtggtgg gtgcctgtag tcccagctac tcgggaggct gaggcaggag aatggtgtga | 32760 |
| acccgggaga cggagcttgc attgagccga tcgcgcca ctgcactcca acctggatga | 32820 |
| cagtgtaaga ctcggtctca aaaataaaa aataaaaaa aatactttc tgacttagag | 32880 |
| aatctgggtg aagggtaaat ggaattcctt gtactatttt tgcaactttt ctataatcct | 32940 |
| aaaattgttt caaaataaaa ggttaaaaaa atattttcca gactacttca gaaacctaat | 33000 |
| tactaataat aattctgagt tttaagcaac caacttagaa acttttggaa tgcagtcaac | 33060 |
| ccactgacaa atgaggacta tctgtactat agtattttt tagacggggt ctcagtctgt | 33120 |
| caccctagct ggagtggtgg ggtgatctca gctcattgca acctctgcct cccaggctca | 33180 |
| agcgatcttc ccacctcagc ctcctgtgta gatgggatta caggcaggct ccaccatgcc | 33240 |
| caacgaattt ttttgtattt ttagtagaga aggggtttca ccctgttcc caggctggtc | 33300 |
| tcaaactcct gagctcaagc aatctgcctg cctcggcatc ccaaagtgct gggattacag | 33360 |
| acatgagcca cagagcctgg ccttttagtc tatttcgatt cttcatttca attcactata | 33420 |
| ctttttttct aagttttaaa atatttttta tcttttacca ttgacatttt gtgttgtttt | 33480 |
| acagcttctt tatattggtc tgcattccaa agacaaaatg aagtctctta tgttttgtga | 33540 |
| tatgtgttaa aataattgaa ctagacaaga atgttaggcc caagtgagat gaaggaaagg | 33600 |
| ctctttgata agcatttggc attttagatc agagatggca agtacgtatg acatagcatt | 33660 |
| cttcttttat acatttcaga tattatttgt tgatcagaca ctcttcttcc tgtcttggac | 33720 |
| cacacagtgt tttaggtatc tgctgtcagt tgatcagagt tggcatgaga aacaaaaaaa | 33780 |
| atctattggc atctctgact tagaagatca gttttgggag aatcttctgg aatatctatt | 33840 |

```
ctattcttaa gtttaatgag taatttcatc cattttatga agtaacataa caattctgga    33900
agcctagtta tttaaagaat gctttaagct ttgtttcttg tcacttcaat tttcagatgt    33960
ttgtgaaacc aagtctgcta ttttaataaa atgttcttaa agtataatgt aactttaaaa    34020
aatctacata cttgtgtgtc acatctttag cctttaattg ggtgactttt taaatgttat    34080
ctacttttat tcttatgttt tccttcccag gagtggacct accctatgag acgagagatg    34140
caggtatggc aaccttttct ttgttcaaac caacccatgt tattatcata ataagaacct    34200
tagtttatag gatttgagac ctgctgattt catgatctgt aggttcatca ttatgtattt    34260
taaataatta ttttaaatat ttaaggttaa tcttggatct taaaacgatg ggaaattaga    34320
aagaggaacg tagtaatagg tgtatgtgct taatgagtca ctttctcttg gttttttttt    34380 tgttttttt tttttgaaac agagtttcgc tcttgttgcc caggctagag tgcaatggca    34440
cgatctcggc tcaccgcaac gtccacctcc cgggttcaag tgattctcct gcctcagcct    34500
cccgagtagc tgggattaca ggcatgcgcc accacaccca gctaattttg tatttttagt    34560
agagacaggg tttctccttg ttcaggctgg tctcacactc ctgacctcag gtgatccagt    34620
gacctcaggt gatccaccca ccttggcctc ccaaagtgct gggattacag gcatgagcca    34680
ccgtgcctgg ccaatgagtc actttctttt tcctcacgtg aaaaattgga tactttcttt    34740
gtattccttt tgaaagcagt ttgctttctc tgtttgtcta gataagttag ggagagttgt    34800
ctgtacaaca aataagcatt gttcattttg tgtccgattt taatcaact tccacaatta     34860 agtcttctag aagatcaaat tgaatacttt cagtttggaa tgaattaaac gatagctaac    34920
cctcatagca gttcattttc ttttgcattt cataccattt accgtcaagt ctgtttgccc    34980
caggattaag cagtatcttg ttcctgggaa tcccatgact tctaaaaatc tgttactttt    35040
ctctcttaat gaaagttcac tttgaaaaaa taggtgagta cctatgaggc attttacttg    35100
gtgttaggag gaatgcaaag atgactaaat gtaatttctg cccacaaaag cctggtggaa    35160
gaaatcagtt ttatatacaa ataattatga cttatagaac tgaactataa agttactgtt    35220
agtatctagg gtatgatata tccagactga aagctttctg tattgaattt acataaaata    35280
aatttgaatt caacatctgg aaggtacata cttgttgaaa ttttgtcaac tgcaaaatat    35340
ttgaatttgg aattttttatg ttacagtaat aatttgcttc tattaactat agataatagt   35400
tttaggtcag gcacaggagt tcatgtctgt aattccagcc gtttgggagg ctgaggcaga    35460
aggatcacta gagcccagga gttccttatc agcctgggca acatagtgag acttcgtctc    35520 tatttttaa agaaaaaaa aaagattaaa aaaatagata atagttccaa tcttgttgta      35580
tcttgtgctg cttttgattt ggccaaataa ggtttgtctt atttatatag ccttatagat    35640
ttaaattgct gatggtaaat acctcaaatt ttttttttc taggaaattt tacctggatt     35700
gttcttaggc ccatattcat ctgctatgaa aagcaaggta tgaactttgt tagattcatc    35760
aagagagact tttattaacc aacttttctt gggtaagttt tttagtaata aagagtttta    35820
ttttagggag catccacaaa tactgtctgt taacagtaat tgtcactctg gagtaccttc    35880
ctctttccct atttactag accagtagtt ctcaagtgtt tcaccacaaa tcagagtttt     35940
tgttttttcc tcatgaaatt tgtatgtttg aaagatttac caaataactg accttttaata   36000 acttatttac tctctaaaac actagacatc tgtaattgct aatcatagct tcagaacaat    36060
atgagatgta gttaaagccc aaaataagga atttcaatgt ttagttaaac cttccttatc    36120
aagggtaaga ctgtgtgtgt taattgaaag tcattcacct tagttctgtt ttgccagcca    36180
```

```
gactttagag agctagttgg tatccccgct ctgaaatttg aaactttttg agcaccagta   36240
tgtcactcga aggaaatcct cactggagta tttcggattt cggattttg gattagggat    36300
gctcaattat aagtataatg caaataggca aaacaaacaa atccaaactc tgaaatattt   36360
ctggtccctg gcattttaaa taagggatat tcaatccgta tagatattct acatagtcaa   36420
actttaatgg acttactcag ttgcagttaa aataggtaga tctcatttta ataaatatag   36480
caatgttctt gccacttcta aaagattcaa tgctactaat tctctttgag ttacaacgtg   36540
gaacatatca cagatgtctt tccccaatac tttgcctatt cagaagtcag tatacttaaa   36600
ttgtgtttga tatatccata atttaatttg atgttcttag gaatttaacc ggttttaaaa   36660
ggtcattgat tttgaaactg gaagatttt ttgacagttg agacatggct aagagtaaac     36720
ctggtcatct tgatgatttt tgcttagttg gaaagatagg gagttagtaa aataagtac    36780
tagggaaagg ataggcagg taactataga catagccgta atttattttg taaaagacag     36840
atgtaaacaa ggttattgtc catataattt gctattcacc aagtactagt cttccagatg   36900
gttttagata atttacattt ttgaaattcc cactgtactt tataaatata catacagtat   36960
ttatcacatt aaattaaagt atttgtttaa aggtctatct cctcaatggg aggctgaggc   37020
aggcggatta catgaggcca ggagttcgag accagcctgg ccaacatggc aaaacccgt    37080
ctctactaaa aatacaaaaa ttagctggtt atggtggtac acacctgtaa tcccagctac   37140
tcacgaggct gaggcgcgag aattgcttga atctgggagg tagaagttgc agtgagccaa   37200
catggcacca ctgtactcca gcctggtgaa cagagtgaga ctttgtctca aaatgaaaca   37260
aaaacacgca caaaaaaagg tctagttctt caaaacttct tttcttgaaa tgtcaccatg   37320
gtcttattag acaggaaaag cctctgtggc agtttatttc ccaccctagg taaccataat   37380
atagcccata tttctttca taccattatc taaaacaac aacaaaaaat aataatggag     37440
ataaacctaa atgataaac tcctttttaa acactcattt actgttatta ttttgtggga   37500
gaggagtggg gtcttgctct gttacccagg ctggagtaca gtggcgcgct ctcatagctc   37560
actgtaacct caaactcctg ggctcaagct gtcttcccac cttagtctcc caagtagcca   37620
ggactacggg cacacaccac catgcctggc ttaattctca aagttttgt agagatggag     37680
tctggctatg ctggccacat ttacttaagt atatctttt attaaattca aatacagttt    37740
aaataaaagg gacaaattta gggcctttgt aattagtaaa cggtttgttt ttgtaaagtt   37800
tttctactgt ttttaaatgt gaggtaaggt cataatttgc ttcatattag gttggtgcaa   37860
aagtaattgc agatctgcct ctgaaaagta caaaatctat tcgctgttac gttagggctc   37920
tattttgata gtttatttt atttagtagt agtctattgg gccttcaaaa cttgtttaag    37980
catatttata cataattatg tgcatcgtct tgtgctttct cacattcata agtagatag    38040
gaaaactcca taggcatcaa gtgtaaacga aggacttaat gttgaatttg ttgtggaaat   38100
tggcacaaat ctcaatatag aacattggtt aattattaat cttaccaaat gcttatctca   38160
ctttccctaa ctcaagttat actcaagaaa tacaaagata attgaattct aatctatgct   38220
gacataaaac ttgctgcaga aattaacact taaaacttgc aaattatatt gtcttagccc   38280
aggctgctca aacaaaatac catagacagg gtggcttaaa caacagacga ttatttgagt   38340
tctggaggct ggcaagtcca cagtcatggt ccggctctgg tgaggaccct cttgctggct   38400
cgcagatccc tcccttcttg ctgtatcctc acacggccaa gagaacgagt tcttgcctct   38460
tcttacaagg gtacaatcct gtcatggagg tttctaccct catgacctca atctaaaact   38520
gattatcttc cagagactcc accatcacat cttgggggta aggatttcaa cataagaatt   38580
```

```
tgaggtgatg caaacattta gttcataaca catataaatt attttttttt actttgctca    38640
tgaattatta gtgctactgt tttgtactat ttaaaatgca gaaatggga attaaatata     38700 taggatttaa aacaatgtgt caagaaattc aaggttatct gattctcatg ccatcgtgac    38760
ttgttagttc atttattgaa caggtaatta ttgaacaact taactagtta tacatacttg    38820
atacttaagt gaattgtatt atacatttta cacatactat gtatcagtga acaaataaaa    38880
atcttttctg tcatggaact taatgctcta ggtaataaaa taacatctat aaactcactt    38940
aaacttatca ctagcaaatg aaaacttatt atctggtaat ttctagaatt gtcatgttaa    39000
attgctttaa gtatggagcc aaaagcacta caggttgagt atccctaatc tgaaaaatct    39060
gaaatgctcc aaagtgaaac ttttgagtg tcagcatgac agcacaagtg aattccacac     39120
ctgaccccat gtaatgggtc actgtcaaaa ttttgtttca tgcaccaaat gactgtatga    39180
aattacgttc agagtatata tggtgtgtgt gaaacataaa tgaattttgt gtttaaactt    39240
ggataccatc cccaagacat ctgagtatgt atatgcaaat atttcaaaat ctgaaatctg    39300
aaacacttct ggtcctacct tgggaccagc attttagata agggatactc aacctgtatt    39360
gaatataata agatgtcatt gaagttgcca ttttttaactt caggaaaatt tttaaatggt   39420
aaaaggttaa ttagattctg tgaagtatgt aaattaattc tgactcttaa agtatactgg    39480
gagaggcaag gagttgtcta gagatttggg ttccagtact gctgttaact aggtcggtga    39540
tgtccaagta tttggtaatg taactgtttt atgtcttagt ggttctctct aaacaataaa    39600
gattgcagtc aatatatatt aactaccatt tattaaacac ttgctgtgtg tcccaggtgc    39660
tatgccaaac atcttacata aaggttccat caagctctaa aattgtaggt atgaaatatc    39720
cctgttaacc ttttgaggac attaatgtat taatcttgaa tcattgaaat atcttgctgc    39780
ccacttcagg tatattataa aattagcttt aattccctgg acttaagcag agatgtgggt    39840
tctgtgtatt ttcaaacatc tgtgttatat agtaagatga tgtttgatat tttaaaatat    39900
ttatcttccc tgtcctcccc ctgctttttt ttttatacag ctacctgtac tacagaaaca    39960
tggaataacc catataatat gcatacgaca aaatattgaa gcaaacttta ttaaaccaaa    40020
ctttcagcag ttatttaggt aagaattatt gctatgattt gtaaaacact taatgaagtt    40080
tcatttcagg ttttgtacca tcagttgttt ctgtacatat ctagtttgta aaaatgggtc    40140
atatagtaca tagttttttta aaataaattt tacttaaaat acttaaataa attatgccca    40200
taatgcagaa ttcaaaggt tcaaaagagt gtatattgtc aagaagtttc tgggaaagta     40260
aaaataaaaa agaatttaaa aataatgtat actgaaaaat aggttttagt gtacattatt    40320
ttatctcttg agggataaag gaattgagta tctaggggat aggtttaggg aaacagcatc    40380
tactgttacc tctttattgg gtagttttg agtgttaggt taaatttatg agcatagtct     40440
tatagataaa tttttttta cattggcttt ctttttact ttatattttt tggagattgg      40500
tttatatcgg tatgtatatc aaactgctta ttctttttaa gttgcattgt aatccattgt    40560
atggctatac taaaatttat tcaattagtc tgttagatat ttagattgtt ctggccttg     40620 tactaatatg tatagcatat agtgactatc attgtacata ttactcaatt tatatgtgag    40680
catattgata gggcttattt gcagaattgc tggatataag agtatgaaca ttttaaattt    40740
tgatagatgt tgcagattgt tttccagtgc gttgtatcag tgtacattcc cattatcaag    40800
tatgtgagag tgactcttcc cttagtatct ctccaagacg gaattgtgaa acattttaa     40860 tttctcaaag tctaatggag taaaaatggt atctcatttg atgttcttat ttatcttgta    40920
```

```
agttcagttg agcatgtaat ggttttaat gttctttatt ttaacttcat ttttaaaata    40980
gagtatatta cgcatggtac aaaagtgaaa ggatatgtaa acatatataa tgaaagtaac    41040
tctactttt ctcttaaccc aagccacctt gctcctatcc tgggaggcag cttcttcctt    41100
caatatctat gtaaaagtat atatgttaaa aatattttag gccagcacgg tggctcacgc    41160
ctgtaatccc agcattttgg gaggccgagg tgggcagatc acctgaggtc aggagttcga    41220
gaccagcctg gccaacatgg caaaacccca tctctactaa aacaaaaatt acctgagcgt    41280
ggtggcacat gcctgtaatc ccagcagctc aggagactga gcaggagaa ttgcttgaac    41340
ccagaaggca gaggttacag tgagccgaga tcacaccact gcactccagc ctgggcaaca    41400
gagcaagaca ccgtctcaaa aacaaaacaa aacaaaacaa aaaaaaaaca gtgctgtggc    41460
ttacacctat aatcccagta ctttgggagg ctgaggaggg tggatcacga ggtcgagatt    41520
gagactgtcc tggccaacac agtgagaccc cgtctctact aaaaatacaa aaattatctg    41580
ggcgtggtgg cacatgcctg tagtcccagc tactcaggag gctgaggcag gagaatcact    41640
tgaacctggg aggcagaggt ttcagtgagc caagattgcc ccactgcact ccagcctggc    41700
gacagagcaa gactctgtct caaaaataaa aaaaaaatt taatgctctg ctttatttt    41760
acaatgaaac caatctataa atatctgtaa atacaagata catactctaa aatacattgt    41820
gtgaacatat aatagaatac tatgtaacca tgaaaaagaa tgaaatatat gtatgtgttt    41880
ggatttggga tgatctccaa gataatgcat tacatgaata aagcagggtg tggaacaatg    41940
tatatatttg caatgtgttg agtaaatata tatatactac attccatata tttattctta    42000
atatatgcat agaaaatttc tggaccaaga ggctagaaac ttcatagtga ttgcttctaa    42060
gaaggaaat tcagggcctg tgatggtaga gggacgtatt tttctttcgt ttttaattt    42120
gtttttttt gttgttgttg tttttttttt ttttttgaga tggagtctca ctctgtcacc    42180
caggctggag tgcagtggtg tgatcttggc tcactgcaac ctctgcctcc tgggttcaag    42240
cgattctcct gcctcagcct cctgagtagc tgggattaca ggcatgtgcc accacaccca    42300
gctaattttt tttttttttt ttttttgga cagagtttcg ctctgttgcc caggctggag    42360
tgcagtggca tgatctcggc tcactgcatc ctccgcctcc caggtttaag caattctctg    42420
cgtcagcctt ctaagtagct gagattacag gtgcccacca ccactcccag ataattttt    42480
ttgtattttt agtagagacg gggtttcagc atcttggcca ggctgatctt gaactcctga    42540
cctcttgatc cacctgcctc agcctcccaa agcactggga ttacaggtgt gagccaccgc    42600
acctggccta atttttgtat ttttagtaca gacggggttt caccatgttg gccaggctgg    42660
tctcgaactc ctgacctcgt gatctgccca cctcggcctc ccaaagcact gggatttaca    42720
ggcgtaagcc actacgctca gccgagggac atatttttca tggtaccctt gatatccatg    42780
ggggattgcc tccaggaacc cccatgaata acaaaatcct cagatgctca agtcccttat    42840
ataaactggt gtaatatttg catataacct gtgcacattc tctcatatac attaaatcat    42900
ctctagatta cttctaatac ttagtacagt gtaagtgctg tgtgaatagt attggatttt    42960
attttatta tttttagtgt tgtattttac cttattttt gttaatgttt tttattgttg    43020
tcggttgaat ccacaggtat gaaattcttg gatatggagg gctgactctt tactttgta    43080
gtgttttt tttacaccat atttagttta ttaaaactag ttattaaaaa ggaatatccc    43140
aaaacactga ttttttttt ttttttttt tttttttgag acagagtctc gctctgtcat    43200
ccaggctaga atgcagggct cactgcaacc tctgcctcca agttcaggc aattcttctg    43260
cctcagcctc ctgagtagca gagattacag gcatgtgcca ccacgcctgg ctaattttg    43320
```

-continued

```
tatttttagt agagacgggg tttcaccatg ttggtcaggc tggtctcaaa ctcctgacct    43380
cgtgatccgc ctgccttggc ctcccacagt gctgggatta caggcgtgag ccactgcgcc    43440
cggcctgaat tttttataat tatgaaagaa atacttttttt tttttttcaaa gataggatct    43500
ttctctgctg cccagcctgg attgcattgg catgatttct gttcattgta gccttgacct    43560
cccaggctca agcaatcttc ctgcctcagc cttccaagta gctgggacta caggtgcacc    43620
accggatcgg gctaattttt tttttttttt tctagagatg gggttttgct gtgttgccca    43680
ggctgttctt gaactcctga gcttaagcga tctacccacc tcagcctccc aaagtgctgg    43740
ggttacaggc atgagccacc acacctggcc atgaaacact tattctttat aagtacttcg    43800
gaaggtatag aatgacacca agaaaaatat ttaaatcatc tacagttcca caattcagag    43860
aaaacacttt tgttaacatt tggaatattt ccttttaaat cgttctctgt tgtgtatgtg    43920
tatttacgta tatatgcata gaattattaa agaaaatgag aatgttgtat tttaaaatat    43980
caaactatat aaggtgaaac taatcttaag aaaaaacaaa aaagccaaaa aatcatacta    44040
ttcatttcta atgtgtacag acttttttgtt ttaaattata atgttgtttg tgcaggttct    44100
ttatcctaat ggaagaacca tttctcctta aacttttaca atactagctt cttagagatt    44160
gatagttcta ctagcagtgc ttgacactga aaatgttatg cgttaaaata tttaatttca    44220
ttctgagtta acattttttcc cctgaagcat tatttttatgt aactggaata cccagtcact    44280
tcaggataca gtcattgtcg aaatccttgt aggttaaata ttggattttc ctcagatcct    44340
gaggttcagc ttctgtgttt tttttttgttt gtttttttgt ttttttttttt ttgttttttga    44400
aacagagtct tgctgtttca cccaggctgg agtgcagtgg cacaattttg cccactgca    44460
acctctgcct cccgggttta agtgattctc ctgcctcagc ctcctgagta gctgggatta    44520
caggtgtgca ccaccatgcc tggctaattt ttatatttttt agtagagatg gggtttcacc    44580
atgttggcca ggatggtctt gaactcctga cctcaggcaa tccacctgcc tcggcttccc    44640
caagtgctgg gattacaagc atgagccacc atgctcagcc tcagcttctc tgtattaaag    44700
tcctgaattc tttgaagttg ttaccaccta aatgatcatt gaaaaactgt attttttagt    44760
gcaaaattgt tcttaaaact aatttaataa cttagctaat tgcctatagt tgtgttaata    44820
aacagtggtc ttagaaacgc ttagaaatgg aagttttttta caaaataag ctaacatatt    44880
taaaatgcct tttaagtatt ttgtaaagtg taaaattcag tacaggtgct ctctcagcta    44940
gttttttttt tttttttttt ttccccttta ctaaagatga gttcaaacag tgaatgtttg    45000
actcctggtt ccatagacca taccttccgt ttttatttgt tcgttctctt agactttgga    45060
cttcctctga aatgtcctct gtaggttcat gagcaggagt cacaggacca cttagagaac    45120
aatcttctgg tcttagagaa attggtagaa ataaaagaat aacataacga ttacaggtac    45180
ttttgtcttt atttctaggt ccactctaat ctagaggaat gtatcttcct gcttgtgatt    45240
tttctatttt aaccagatgg ttcattatat gcaaataaaa tatgtattta tttttgagat    45300
aagaatcttg ctctgttacc caggctggag tgcagtggcc caatcacagc ttactatatc    45360
cttgacttcc aggctcacac agttctacct cagccccctt agtagctggg actataagtg    45420
cacaccacga cacccagcta attttttaat attctgtaga gatggagtct ccctctgttg    45480
ctcaggctgg tctcgaatcc ctgggctcaa gtgatcctcc caccttggcc tcccaaaaga    45540
gtttcttttt gctgggatta taggcatgag cccattgtgc ccagcctgat ggatttttta    45600
aatacttaaa tatcagagat gttaacatgg tgtttcaggt tttaatgcct tcaagcaatg    45660
```

-continued

```
taaaatctac cacacagttc ttgggaatat gatactttga aagttgtttt gcattcttgc    45720
catggttaac aagaaataat gagttatttt tttaaagtac cttaagtgtt ttacttaaag    45780
tgtgcttatc acaaaatact ctattttcag atatttagtc ctggatattg cagataatcc    45840
agttgaaaat ataatacgtt ttttccctat ggtaggtacc agtattttt aaatatcatt     45900 taaaatttat ttatgatttg acttcttagt tgtgctttt tttttttttt ttttttttt     45960 tttgagacaa gagttttact cttgttgccc aggctggagt gcaatggcgc aatcttggct    46020
caccacaacc tctgcttccc gggttcaagt gattttctg cctcagcctc ccaagtggct    46080
gggattacag gcatgagccg ccatgcccag ctaattttgt attttagta gagacggggt     46140 ttctccatgt tgatcaggct ggtctcaaat tctcgacctc aggtgatctg cctgcctcag    46200
cctcccaaag tgctggcatt acaggcgtga gccaccgtgc ccagccctt taattgtgct     46260 tgtaaagctt gctactttta ctttgctatg actgaaaatt atgtgattgt gttttaaaa     46320 gaattatttg tagaaaattt tttatgatct ccagaaattt gaggaatcat attgtgaatg    46380
tattggactt aaattaaatt ttggcttctt taatttttt ggacttgtaa tagttctatt     46440
tatagcattt tggaaattgg tgaatcaaaa taattttat acatataaat taggaaattg     46500
ttttcaatag gtttcatttt gtttcattat atgcatttat tttatgctta cattaatcca    46560 catgtcttt gcctccagac taaggaattt attgatggga gcttacaaat gggaggtaaa     46620
taacatttcc tttccttaac taatgtttat attttgatta tttgttaatt ttttagttgg    46680
tatttgtctt aaatgcagga tatggaagtt acaattatat gtagtagctt actcccaaat    46740
ttgtattttc ccaattactt gtttcatttg gataggcttt ctggagtatc cctgtagact    46800
gttttcaaat tctctgtgag ctttcagttt ctttaataag agtctgctat attctctaca    46860
cagttgataa taacaaattg taaagatttg aagatatcca agtgattata gtatataagg    46920
agttacttta ctgtggtttc aatgtagttc agctactgac tcaggtgttt ttctattaga    46980
ataatgaatt catgtttttc aggaaaagtt cttgtgcatg gaaatgcagg gatctccaga    47040
aggtatgaag ttagaaataa tctttctttc tataacattt aattaatggg ctgtattttc    47100
tggttgtttt taaaattatt ttcccctctt cagtgcagcc tttgttattg catacattat    47160
ggaaacattt ggaatgaagt acaggtaaga aaatacccta aaacctagcc acagtttaaa    47220
ttctcattaa aatgaaactt aatgggaata gtttggaagt ttgaagttct tattcccctg    47280
attatttttc atgtagtcat gtttgattag gcaggcccctt attccatgat tagtcttaac    47340
ctaatttatc tacttgtata gatatgcata ggctaatatg gaaatcctat ggaaaactac    47400
ttacctacca caagggaatt ggttggtatg agtataaaaa ctcgtgacca caaatgttag    47460
tgcttgcctt atttaaaggg ctaatttatc atgttctcct ttaacaatag ttggatgaaa    47520
aattacctag gaattgttg cagcatctat ttacaattca gagtagtctt tcttatcaaa     47580
aatcatcttt tccaagcatt ctgtatagat tttttaaaag atagggggtg gtaatgagct    47640
tcttgccccc aagacaaagc aaaagcctgg gccagtgtac agtatttcct ttctcagctt    47700
ttcttgttct acaaattaga aatcttatag taatcattga cacatctttc tatttcagtc    47760
cccttttata tctaaattag aatggataac tttgcttaaa aatatctatt cttaaaggaa    47820
tattatttga atacaaatat ttatttattt attttgaga cggcgtcttg ctctattggc     47880
aggctggagt gcagtggtgc gatctcagct cactgcaacc cccgcctccc agattcaagc    47940
aattctcctg cctcagcctc cctagtagct gagactacag gtgcacacca ccacgcctgg    48000 ctaattttg tattttatt agagatgggg tttcaccatg ttggccagga tggtctcgat     48060
```

```
ttcttgacct tgtgatccac ctgcctcggc ctcccaaggt gctggtatta caggggtgag    48120
ccactgcacc cagccagaat acaaatattt aattgaaaaa agattaaaca tgtattgatg    48180
gactttatgt tttatatatt gttttttatta tttcgaattt tgtcagacca ttaatgttgg    48240
aaataacttg tatttattgg gtctctgcta tgagctcagt actattatag gcactttaag    48300
cctcataaca aaagtaaata aacctcttta accagtgata gtattttgag cttgaacttg    48360
tactatatgc acaaaatgct tacattttat atatttattt tagagacagg gtcttccttt    48420
gtttctcagg ctggagtgta gtggcacaat catagctcac tgtagtctca gacttgagga    48480
ctcaagtaat cctcccacct cagcctctca agaagctggg actataccac atcactgtgc    48540
ctggctaatt tttaagtttt ttgtagagat ggggtcttac tacattgccc aggctggtct    48600
caaagtcctg gcttcaagca gtcctcctgt gttggcctct caaaggattg gggttacagg    48660
caagagccac tgcacctggc cactttacac ttacctccta ttcatagtag ttccccaagg    48720
taggtgttat tagactcttc attttaccaa tggacaaaat agagcttaga gaagttgagc    48780
aagctgccgt aagcatatag ctggtgagaa aaggaattgt gatatttaat ctcatcatgc    48840
tttttccatt acaactcatt accccctctct attgctaagt tgtatgatta tgattaattc    48900
attaaataat gctatcacat taacactctt tttctgtttt cagagatgct tttgcttatg    48960
ttcaagaaag aagatttttgt attaatccta atgctggatt tgtccatcaa cttcaggtaa    49020
cttttcttcc tctttaaggc aatcagaagt aagatataaa atcttttata catgtaattt    49080
aggtgtacaa tttactttgt gaatacttaa aattgccata atctgactac tttgatgctt    49140
tattcaagtt tatatctcta tttagaagta ttttcttggc tgggtgtggt ggcttatacc    49200
tataatcaca gcactttggg agaacaaggc atttggattg cttgaggcca gaagtatgag    49260
atcagcctga gcaacaaagt gagacccaat ctctaaaaaa taaaaaatta aaaaaaaatt    49320
agccagtcat ggtggtgcat ggctgtggtc ccagctactc aggaggctga gatgggagga    49380
ttgcttgagc ccaggagttt gaggctacag tgaacagtgt gtctttgcac tccagcctgg    49440
cccacagagt gagacccccat ccctaaaaaa ttaaaaaaac ttttttttct taaaggctgg    49500
cattaccaag aaaaaagggt taaagacaca ttatcaaatc taaagtaaaa taattgctgt    49560
tagaaatgtc tgatttttttt ttgttgttca ttttgatcac acagagcata agacagtttt    49620
gattctaagt atactaacta taacagcttt ttctattcta tgtttatctt ttccatgttg    49680
tttcatattt tgttgatgcc tggcagatgc actgacaaag atgataagtc tatgaattaa    49740
cctaattaga ccacgttgct cagtttattc caagaggcaa aatcataggc tgcagaatgt    49800
gctctggcta attacatcca attatgtagg aataaagctc atgtttcaac atcaagaata    49860
tttattacaa aatatattgt tatagttacc aaggtttaaa ttttatttta atatttaatt    49920 tactttttaat ttttactaca ttcaaaagag aaacagtgtc atctgtgttc agcctgttca    49980
tgtaaaatgt tgtcttcta actttgtaag tttcttttgcc ttttaccatg ttgtagaaaa    50040
cattgttttt tttcattttt tttaaactat ttttttaagct tttcttttttt ttgtggatac    50100 atagtaggtt aggtattttg atacaggcat gcaatgtgta ataatcacat catgaaaaaa    50160
tagagtatcc atcccatcaa tcatttatcc tttgtgnnnn nnnnnnnnnn nnnnnnnnn    50220 nnnnnnnnnn nnncctccca agtagctggg attacaggca cgtgccacca cgcccaggta    50280 attttttgtat ttttaataga gatgggatgg ccggtgtgg tggctcacgc ctgtaatccc    50340
aacactttgg gaggctgagg tgggtggatc acctgagatc aggagtttga ccagcctg    50400
```

-continued

```
gccaacatcg tgaaaccctg tctctactaa aattacaaaa attagccagg cgtggtggca    50460
ggtgcctgta atcccagcta acnnnnnnnn nnnnnnnnnn nnnnnnnnnn nnnnnnnnnn    50520
nnnnnnnnnn nntgctggaa agggatcacc tgagtatcag gagtttgaga ccagcctggc    50580
caacatcgtg aaaccctgtc tctactaaaa ttacaaaaat tagccaggcg tggtggcagg    50640
tgcctgtaat cccagctact tgggaggctg aggcaggaga attgcttgaa ctcgggaggc    50700
ggaggttgca gtgagccgag atggcatcat tgcactccag cctgcggaac aagagcaaga    50760
cttcgtcaca aaagaaaaaa aaaatagag atagggtttt gccatgttgc ccaggatggt    50820
cttgaactcc tgacctcagg tgatccaccc accttggcct ctcaaagtgc tggaattaca    50880
ggcgtgagcc accactcctg gcccaaaaat gttttatcag attttttgtga tcatttgttg    50940 gtgttcctct caccggtttg taagagctct ttttatatta tggaaatcta tttatagcct    51000
accgatttga aatatcattt ttatttttata ccaaattctg atatgtcctt tagaagtttg    51060 aagtttctt ttttaaggtg cttatggaat ggctagttct agtttttgaa ccgttaatat    51120
ggtgacttga gttactggat cacattagat tggatttcct aatattgaat catccttttg    51180
gtccagcaat ggatcccact tggttatgat agactgttct gttaatgtat tgctggattg    51240
tatttgctaa tctttttgtt caggattttg gaatcagtta aatagtaaat tggtttgtct    51300
ttcttttttt tttctgtact atccttttct ggttttacta tctctgtcac agtgttctca    51360 tttttagtg gaagctttcc atttctcttt gtgccatgga tcaatttaaa ttagattgga    51420
gttacttgtc tcttaatgca ttagtatatg gcacctgtga aatatctgac cataatgttt    51480
tatctaattc agttattcat tatttcattc attcatatat tttgacaata gaccagttct    51540
cagacaacat tcttcatttg gtgtatcggt ttgatttttt cttttctttc tttctttctt    51600 tcttttttt tttttttttt ttttttttga ggcagagtct tctgctctgt tgcccaggct    51660
ggactgcagt ggtgcaatct caactcactg caacctctgc cacctgggtt caagtgattc    51720
tgctgcctca gcctccaaaa tagctgggat tacaggtgc ctgccaccac aactggctaa    51780
ttttgtattt tcagtagaga cgaggtttca ccacattggc caggctggtc tcaaactcct    51840
aacctctggt gatccgcccg cctcggcccc cagagtgctg gggttacaga tgtgagccac    51900
tgctcctggc ctggtttgat tttctgatac ccctcaggtc actttggatg tatttatgat    51960
cttctgtgta atcattgatt tcataagagt tctacataga attaaggaaa ataatatctt    52020
gtactttaat atcttttggt tctattattt tttttcttca tctggttagt ccatgttgtt    52080
tttctgtatt ctaatttctg cttccttggt actttgcttt agtgttgttt gctgctgctg    52140
ttgtgaattt cctgagttga aaacttggtt tcttttatt ctttcaaaaa ttcaaggcta    52200
ttaattatcc tctttgcatt gtgttagtcg catgctgcag attctcatct gcattatttt    52260
tatgttatag cttgatattc tgtgatttca gttttggttt catttttat ctaatatgtg    52320 ttgagatttt ttttattgta taggtgactg ggttttaaat tttttatttt tgttcatatt    52380 tagtttatt acattgtaat cacagaatgt tttgtagtac ttgtattttt tgatgttttc    52440
tttgtggttt aatatgtagt tgttttcatg aattttatgg gcatttgaaa agaagatgca    52500
ttctgttttc aggggataaa gttaaatgta tttgtccact tgatctgtct tgggctgaaa    52560
tcagtgaatt gaaatctttt actatattgt gtttattttt tctttatttc cccttttttg    52620
gttctgcaag ttttttttctg tacttaacta tttggtacat aaaaattcaa gttaggtttt    52680
tattttagtt gtaccctgtt taaatttcag ggttttttgt tgttgttgtt gagacagagt    52740
cttgctctgt ggcccaggct ggagtgcagt ggtgcgatct cggctcactg caacctctgc    52800
```

```
ctcctgggtt caagtgattc tcctgcctca gcctcccaag tagctgggat tacaggcatg   52860
catcaccacg cccggctaat ttttgtattt ttagtagaga cggggtttca ccatgttggc   52920
caggctggtc tcgaactcct gacctcatga tcctcccacc tcggcctccc aaagtgctgg   52980
gattacaggt gtgagccact gtgcctggac aaatttcggt tattttacct tgcagttaac   53040
ctcgtttaat attgtgaatc ctactctttc tgttcgcttg ctaccttttg agttttccca   53100
ttccttttcc ttcaagcttt ctaaatcact tgattttaga tgcttttcct cagtgtagtc   53160
taggattgag ttttgctatt agatttggta tcattgtttc ctaataggtg aatttaaccc   53220
actttcattt actgaaaatg acagatacaa tcttatctat tattatttca tattatgctt   53280
tctgttttaa atgaatcctt tttttaacct tctgctatag tttaaaattt tttggtgtgt   53340
ttatgtttgt tacataattt ttaaggtttt atttatttac ttttcctttt ttttttttt   53400 tttttttgagt tagagtctca cactcttgcc caggctggag tacagtggtg tgatctcggc   53460
tcactgcaac ctttgcctcc tgggttcaag cgattcacac acctcagcct cccgagtagc   53520
tgggattaca gacatatgtc accacatcca gctaattttt gtattttgg tagagacggg   53580 gttttgccat gttggccagg atggtctcga attcctgaga tcatgtgatc cacccgcctc   53640
agcatcccga agtgctggga ttacgggcgt gagccacggc gcccagcccc ttaatcctac   53700
atttaaatag ggattcagcc caatcctatt acctgtttcc aggggtcttt attaaactct   53760
tggactttat taagaatagt ttcatggaaa ctatattccc agggaaaact atccctttgc   53820
atattggaaa aatatttttc ttttttgccct tatatttgaa tgacagtggc tagatataaa   53880
ataggtattt aatactttt ccctagtgat tttgtacaca gacctgatat taaatatttt   53940
ttgtttgttt tttatttttt ggagatggag tctcactctg tcgcccaggc tggaatgagt   54000
gcagtggtac aatctaggct cactgcaatc tccacctccc gagttcaagt gattctccgc   54060
ttcagcctcc tgattagctg ggattacagg cacatgccac cacacccagc taatttata   54120 tttttagaag agatggaatt tcaccatgtt agctaggctg gtctcaaact tccgacctca   54180
ggtgatctgc cctcctcggc ctcccaaagt gttgggatta caggtgtgag ccaccgtgcc   54240
tggcctaaat attgttttag agaagtttga aggcagacca attttaagat tcccccctta   54300
ggtgaattga tttgtatcag gagaaggttg tctagatcag cagtctccaa cctttttcac   54360
accaaggacc agtttcatga agacaatttt tccacggat ggggtggcgg gggagatggt   54420
ttcaggacaa aactgttcta tatcagatca tcaggcatta gttaaggagt gtgcaaccta   54480
gatccctcgc ataccatagg gagggatagg tttaccatag ggtttgcgct cctgtgagac   54540
tctaatgctg ctgttgatct gagaggaggt ggtgctcaga tggtaatgct ccctggagtg   54600
ccactcacct cctgctgtgt ggcctggttc ctgacaggcg atggaccgat tctggggtct   54660
gcagtccagg ggtggggacc ctcatctaga tgaccataag atgctttatc aaggtgtatc   54720
ctggtttttt atgttttttgt tttttgaggg ggtctcgcac tgtcacccag ctacagtgc   54780 agtggcgcga tcatggttca ctgtagcctt gacctcctgg gctcaagtga tcttcccacc   54840
ctagcttcct aagtagctgg gaccatgggt gcacactatc acacctggct aagttttttg   54900
tttgttgttg tttgagacaa agtctcactc tgttgcccaa gttagagtgc aatgggcaa   54960 tcttggctca ctgcaacctc tgcctcctgg gttaaagcga ttcttctgcc tcagtctccc   55020
aagttgccag gattacaggc atgtgccacc aaactcagct aatttttgta ttttttgtag   55080
agagacaggg tttcaccatg taagccaggc tggtctggaa ctgctgacct caggtgatct   55140
```

-continued

```
gcctgcctcg gcctcccaaa gtgctgggat tacgacgtga gaccacacac ctggcttagt   55200 ttttaaatt attttggta gagatgggt tttgccatat tttccaggtt ggtctcaaac       55260
tcctgggctc aagcgatcct cccaccttgg cctcacaagg tgctgggatt acaggcatga   55320
gccactatat ccggccaaga tgtatcttgt tgattgctct acatcagttt ttttctgagt   55380
cacagtgtgc ccttaccact tgcaaattca agccttccct gatttcagga aagttgtctt   55440
ctattgtgta tttacccttt tggttgttct gtttcttttt cttttagta tacccttac     55500 cccggtatag tttatgttcc cttttttctt tgttatttgc tattttctct gtaattattt   55560
gcagctttgt tcttttttt ttttccactt gattttctc acgtttgttt tccatgtccc     55620
atgctgcatt gtttcattaa atatttattt ggcattgttt tagttaggca ctgacagtaa   55680
agcagagaac aaaacagaca ataatccttg acctcacgaa acttatttag tgggagaatc   55740
agacaacaaa caaaatgtag taggccagaa gtaatgaatc caagaaaaat aaggccatgt   55800
aaggaaggtg ggacgagaat tgtatttta gaagggtggt cagaaatggg cttactgaaa   55860
agtgatattt gagcaaagac ctaaagagat gcacgtattt ggggaaaagc atttgaggta   55920
gaggaataag tgtaagtggt ttgaggtggg agcatagttc ttagaaggat actcatttca   55980
tcatagggcc agtcctctca tgacctcatc ccaacttaat cacctgccaa agtccccaca   56040
ttaagtgttt ggacttcaac atatgaatta tgaggggaat gcaaacattc aatcccataa   56100
ctgccatatt ttctttgatt aatttgttca tagttttcat ctgcttcatg gtataagttt   56160
tatggcattt tctttatgac atttggttat actcttgctt ttctgttttt gttttgtttt   56220
gttttgtttt ttcttgcaaa atctttgagt aagacctaac tggttccttc ttgattattg   56280
gtcatctttg aactggaggt attcgtctta gatcagctat ttacccaaga ataaaattgt   56340
gggaaagggg ccagaggagt ggttgggaa ggctgacagc ttgaattttc ccaggttcct    56400
ttggtggcat gaatcagtga gtaagaagca gagctcctta tcacaggt ttattttgtt    56460 taaattgata aacactgatt catattagaa tcacctgggg aatccttacc catgccaatg   56520
aaatcaaaat ctgtgagagt ggggcctagg tatataggtt ttaaagtgcc tcaggtgatt   56580
ctcatgtata tccaggctag aattgctgat ttagccttta cttttagcta tccaagatca   56640
actgatgctt ggctacatgc aaccaaattt cacttccgcc ttaccatact taaacagcct   56700
gctgcttgca aaaaatggca ggtgtaggtg ttcacatttt ccttaatatg tcccaccttc   56760
tcccataggc cactcatatt tcctgacttt gtcataccat gcaagggctt gttggtttta   56820
ttttaggtca cctttttag cgagctatga actgtaccta ctctggccca cagaggagtt    56880
atctgctatg cctagcttag gatggttcta ttttttttga aaattttatt gtgaaattat   56940
aatatagaaa atgcataaaa tgtaaataaa catccatgta actattgccg aagtatggaa   57000
acagaatgtt taccaggaca ccaaaagcct ttttcatgcc gcttctcagg cacaaatctg   57060
tttctccctc tgtaaagtaa ccactatcct gacgtagctg gtaatcaatt ccttttcccc   57120
tcattcttct cattttcagg gtaatggatg tttcctagtt tcatcaaatg ttttccttgt   57180
tttcagaaaa gagagaaaca aaaatgcctt tattcttcta tctataactg gaagcagagg   57240
actattgaga ttgccaattt aagttttgg tgttttttgg ggttttttta aacagatgaa    57300
gtcagagatc attatagcta atgccatact gactggcagt tcagcatgca gtaccctagc   57360
acaaactatt agccgggctt gatttatagt tatcagtagt tctgaattta tgagacagga   57420
attttaaact tccattctc ttcaaacaat atggcactag attttcaat acagatgaag     57480 aataccaaca gtgtatacat taatcactat tttgggtatc caagaatgta aatatataat   57540
```

```
taagttaatt aacttatttt ttttttagga atatgaagcc atctacctag caaaattaac    57600
aatacagatg atgtcaccac tccagataga aaggtcatta tctgttcatt ctggtaccac    57660
aggtaaggat ttttttcttt ttggagaaat ttgggaagaa agataatgaa aggtggagaa    57720
cttgctacaa gttacactga acaatttaaa ttgtttagaa aacttgttaa actattgagc    57780
taattccaga aggattcatt ttataatgaa taaatgtgta ctataataag cttaagtctt    57840
tcaagtagta gtacatccgt gttgtaaaga ttaaaataat acgaatctgg agaaggggcc    57900
ctaaacacgc ttaggtgatc ttattaaaag tagagggcgg ttaatacagc gtgtagcatg    57960
gctaatgtga gcttctttct cttgccatca atatttccat cctttcctcc ctctgttgct    58020
atttcagaag taccctaagc cccttatttt caaagttaat ccaagcatgc tcttaaaatc    58080
ttcctttccc aagaccttgc tacctgtgtt tatcaccttt gtttctctcc caacaaagca    58140
cacaaggcat ttttacttta tttccagttt ttcctaccct gcagttcact tcaatctttg    58200
aaccaacagt tatataaggt agtaagaaca gcttatatac ttagcactga cctggaaatt    58260
gaggacaggt gatctgatcc acaagtatag aactctttgc actctactgc actgcccata    58320
gtgagtaata tgactgtata ttcatcccca aggctcaact tcctaattgt cattgacttt    58380
ttcatttcct ttgccacatc tgtctaataa ttgctctcca catcctatag ggtccgtttt    58440
gtcagtattg ttaacattcc ttccttttt taatagtgac cttaatctag ttcaggtccg    58500
gatttgcctc ctttccaaac tcttgttatt tggtctgttc tgtacattgt ggccagactt    58560
attcccatga aagatatttc taatattgat attttttcctt tgccaaagcc tcctttggct    58620
tcattcctac aaaagtttat agaatgccat atgcccttct gattttttgg tttctttctc    58680
tcattgttct tctttatgtc tgcatttcag aaaacaactg ctgatggttt cctgtgtgtg    58740
tcttcttttc cccacctaaa atgcatcaca tttagtctcc ctattcttgg ttcatatgtc    58800
atctcctcag gaagacatga tgattaatgc actcttcctc taaccctag tcatttggag    58860 ttcccataga agcacagcac ttcatctgaa acttaatcac agtatctggg tttagcctga    58920
gggctaggat attttatctc attcaattgt attgatacta tattttatc tttatgaatt    58980 ttatagtgaa acattcttca attagaatat gccctctgaa ttaacattat tattaccatg    59040
atataacagt cctgtagggc ataagtttaa ggtcatgcca ttgttaggca aaaacacag    59100 cagaccctct gctggtttaa ctgttcccta aagttttcct ccattgagag tctaatttct    59160
tgattataac ttttggggat acagagatag ctttgattct atgtgggaga tttctgtact    59220
agcagatgct ggtatgaaga atagataaaa gaaaatctct ttatatgcta catgccttcc    59280
tttctcccaa cctagacttc gatagcttga gtggaaaaat attttcagct gctcttcata    59340
acagcctctg tgaaagcaaa aagattatct acaaaaaatt atacaaatac aagattaatt    59400
tcctaaattt tatgccctaa gtcacatgtt atggtgccct aaaaaacaat taacttgata    59460
actaaacatt tatgtattat ctcttgaaaa ggtctatttt cacactattt caaaaattat    59520
ttattttata tgcaataacct aagacataat acttgagaag gaaatatat cctgtcatga    59580 agattaaaaa gttataatat ttaggtaatt tatcacaaag gaatttacta aattttgcta    59640
tatcagttgt ggaattttca tagtgtatac atgatcactt aataacaaaa ttttacttgc    59700 tgtaacccttt taacatgaat ttatttttagt gcccttttaa tcttcatgca ataacttta    59760 ggcagtttga agagaacaca tgaagaagag gatgattttg gaaccatgca agtggcgact    59820
gcacagaatg gctgacttga agagcaacat catagagtgt gaatttctat ttgggaagga    59880
```

```
gaaaatacaa gagaaaatta taatgtaaaa tggtaaaaac ataagtagtt ttttttttcaa    59940 ttacatgttg cttccagaca tacttctctg caacttgttg agcaacattt taagatgttg    60000
gacttctgca atagatgaca ctgatggttt tactccttt ttttaaaaaca catgcgcgcg    60060 cacacacaca tgctttacaa gttttattat aaaccaagaa ttttggactt gcaaagaggt    60120
attattgcaa taatgcactt ttcatacttg aaatttattt gtatgatata aagttattac    60180
tttaaacaaa atgcaagtat gggggggattg tttataaagt ttgggtaatt tataacaaaa    60240
tttgctaagg tttgctaaaa attcatttt ctgttctata tattcatttt ttaacataat    60300
tttacagttc aattttatga tggagcctct tacagaaaca ttaacaaaat gcaggaatct    60360
gccacatttc ttttttagta taacttaata gcttaattac catttatttt tttatacttc    60420
ttccattatt aatctttaaa tcatgatcct aattagctgt ccttacttta acttgatcta    60480
attattgctt cctttcttat tactttccta atttttctat attttaaaaa ctacagtttc    60540
catgataaaa ggaaaacgtt ttgatttata gtaccaagtg cttaaacaca aggatagtgt    60600
tagattttcg agtgactttc cttttttgcat ttttttggcag taaaagccaa acgttgtatt    60660 tgttctttc agagttgtcc agcccttttt tcctttgtcc aaaatgattc taaatagaat    60720
ctaataaacc aatgtagcat tatttttttc taaatgaagc cccaaaaaag aaaagtgcct    60780
tgcatcattt aaaaaaaata attaaatcct catggcctct aaattagtat gtagaacact    60840
gaaaagttct taacattttt gtgtaattc ctttcttttt aaaccataaa ttagtttaaa    60900
ctgaaagtac gaggctggaa gaaatattag taaattattt ggaatataga atgtttactc    60960
tttcttttta tgttgtctta atgattctgt gagattgttc cggctcaaac agaagctttt    61020
ctttggggaa ggtgatttgt gggagactct agtgtatttt aaattagcat tttaatccat    61080
tcttgacatt cagttagtcc agatctgccc cataatttgc tttagtaaag tcactttatg    61140
gatttttggc tatgttttag tttgtgtgta taaaagttct aagaaaacat ttttgctatt    61200
ttaagtatgt aagggaagag aggagtgttt ttaactttt atagttgatg actttagggg    61260
tagcacaaac aaaactcctt tgtatctaac ttttctcaat cctctcttga ggtgctttac    61320
taatgggaat gatttctgta tgttcccttg gtacccaaga ggtactatgc aaagtaacct    61380
attacaccaa gttacttgct ttgctttcct ctctatgatg tgataataca gtaaaagctt    61440
tcttacccag catagtggga gagtggagat taattaaaat tgttaattaa gagttaattc    61500
ctattgaccc aggtgatatt tctcttctga tttccctccc cttcccttct cttatcttac    61560
cactgtgaaa acagcatatt gttaatctcg ttgtcgtcca gtattctgct ttgtgattag    61620
gtcttttgat gtacagtggt ctagtggagt caagattcgc attgggtttt ctaaaattcc    61680
agttgataaa agttccagat aacacagctt tcctgtatat agatcactat tgggcaggtc    61740
agcaaagatc tcttacagtg taataataat ctatgatgct tcatttagca gaaactctgc    61800
ttaaaagaat cttcataata gtaagtttag gttttaaaaa cttgtttcat aaatatacat    61860
atatcctctc tagtagtctg gccaaaagaa cagattttgt tattgataat ttgtagctgg    61920
taattttcca catttctat ccactgtaat ttttatgttg tcactgaagt gcctgcccag    61980
tactgtatat tacagtctct cacaaacact gggaaaaggg actgtcatca tcttgagtac    62040
tctgtgtgta tatatatata tatagataga tagatttttt tttttttttt gagacagagt    62100
ctctaatgtc acccaggctg gagtacagtg gcacaatctt ggctcactgc aacctccacc    62160
tcctgggttc aagtgatttt cctgcctcag cctcccaagt agctggggtt agaggcacat    62220
gccaccatgc ctggctaatt tttgtagttt tagtagagat ggggtttcac catgttggcc    62280
```

```
aggctggtct caaactcctg acctcaagtg atccacccac ctcggcctcc caaagtgctg   62340
ggattacagg cgtgagccac tgcgcctggc tgagtacaat attaatgtag acaaaccatg   62400
aagtttatta tttcatataa gaacattaca ggtttgtttt ttcttgcatg tctgtccacc   62460
taatgtttaa gtagttctgg tagctcttcc tattctttat tctatttgat tccatttctg   62520
tgattctttt attaccactg atgttttgtg atagttaact atgataaatt taactgatca   62580
tgatttatct tctagagtat ttaaataatg tatgagtgac cacccaattc caacattaaa   62640
agtgtaatct gggcccataa tttatagtga aattgtatca aaacatagggg aaactgtatt   62700 actgtccatt ttgaaaatat gaaacttgag tattgaaaat attcaaacat ggaatggcag   62760
tattctaatt tcagttagtt ggttcatgtt aatttcttac ctgttagatg tttaaactgc   62820
agtgaccttt acttgtatct actctgtggt ggaaatgtta aaccatgata gcttttgcta   62880
ccaactcaac cacttaactt ttagagcagt tttggggaga gtttatgctt catctgagtt   62940
tagaagtaat gtcagaaaat gttaagcatg tctgtattaa gaaaatataa ggtttctaat   63000
tgtcttatta atatggtaat tcaagtgaat tagaaatatt taactgcaat cttgaattat   63060
aaagttgaga tatatatata tatgtatcaa gatctcaact tgatgtaaag taaatgagca   63120
gttacctggc ggattttttt tttttaaat aactgattta atccataatc ccataacaaa   63180
catagcttca ccctcagtatt ttctttcttt cttttgttcaa cagtgctccg ataagggaat   63240
gctagaaaat agatgagaag tactgaaaga ccttttttttt taattgatta gaaaagtaag   63300
tctctagggt ctttgaatgc tggaattttt tttttttttt ttgtctttcc catctgtggc   63360
agctaaaaca aaaatcactc aaaatattca ggtttacatg ttagctctct ctcataggga   63420
gctgccatac ctcacagttc aaagtgtatt ctatagatca gtaacattat actgacatgt   63480
aattgcaatt tactatgcag caaaaatgat tcaagaagaa aaataaccta cagtgtctgt   63540
atacctttgt atacacaatt gcttaagtta ctctgctttt aacatttgta cttggataaa   63600
atgcttatgt ctgtatagga atgtcacagt gcaagatgct gctagcccag gcacaaagta   63660
ttaaaattat tttgtgaaga ttggtggttg tattaaaact gctgtgccat tataccctcca   63720 aaatattgaa aagctcattc atactgctgc ttatacctca aaacttcttt acttagattg   63780
ttatctgctg ggtaaaagta acccaaattt actctgagtt aagaagagtg gatgaacatt   63840
gaatgttgag aagcacttaa gagtatactc taaaacactg tggttacaca cacacacaaa   63900
attatggtct gtagtccagg caagcctcaa attccagctc aagtttattt ttaaggatta   63960
gttgagcaag tttggagttg gaagtgagag aatcgtgttt aaaggaaagg gtaggtcatc   64020
cacagaacag ctttcagtca ttacaaaaaa aaaatacttc ttgcttttat attaccatct   64080 tccccccatta ggcctacctg catactgtgc ttcatcaaat ctaagatcac ctcacaacta   64140
taccattatt ttaggcacca ctaaaagaca gtgtattgct aacaaaacta tgataaacca   64200
ttgataatat atccagattt cagagatgtt acagtgcatc ttagttgatg aaacaaaaat   64260
atacaaaaca tgagacacag taaaaatgat aagtaccacc tcattatacc ttttcacaag   64320
caaatagtgg ccaaagatgt gaacggccag acacggtagc cgacatatgt aatcccagat   64380
actctggagc ctgaggcaga ggatcacttg agctcaggag tttgagaccg gcttgggcaa   64440
tatagtaaga ccccacagaa aaatgtaaag ccaggtgtga tggcacacac ctgtagttcc   64500
agctactggg gaggctgagg caggagggat ggcttgaacc caggaactgg aggatgcagt   64560
gagctatgat cacaccactg gactccagcc tgggtgatgg agtgggacag tgtctcttta   64620
```

```
aaaaatgtgg gccaggtgca gtggctcgca cctgtcatcc aagcactttg ggaggctgag    64680
gtgggaggat cacttgagcc taggagttaa gagaccagcc tgggcaacat agactccaca    64740
caaaaaattt tttaattag ctgggtgtgg tggcatgcac ctatagtccc agccacatgg    64800
gaggctgagg tggaaggatc atttgagccc aggagattga agcggcagtg tgtggtgatt    64860
gtgcccctgc gctctagcct gggcaacagc gagaccttgt ctcaacaaca acaacaacaa    64920
aaggctatct attgtgggta cactgcctat ggggtagtcc tgctccacaa ggagcagttt    64980
ttaaaaaaaa aaagtttaag aagtgtttta tgtagcactt ttttcatatt tacatttact    65040
caccatatgg cttcaaaaat cataaacata ctcaactaaa attacagatc accattgtcc    65100
tcaatgacac aattttttgta tggtgtacct tacctgtaat tctatttcct atgggaggat    65160
ttaagagata tcttaggaac actatttaaa gggatttact gaagtgccaa ccttgtgaat    65220
gattttacct caaattgttc agtggtaaga aggtaataa agcatttagt tgtgcctta     65280 agtaggctaa ttttttttgt tttgttttga gatggagtct ctctctgtcg ccaggctgga    65340
gtgcagtggt gtgatctcag ctcactgcaa cctttgcctc ccgggttcaa gcgattctct    65400
cgcctcagct tcctgagtag ctgggattac aggcgcatgc caccacgtct ggctaatttt    65460 tcttttttt agtagagaca gggtttcacc attttggtca ggctggtctc aaactcctga    65520
ccttgtgatc tgcccacctc agcctcccaa agtgctggga ttacaggcgt gagccactgc    65580
acccggcctt accaggctaa tttttaaaaa catgcgtttt taattaccag gatttacctg    65640
ataaaactac tctttgtcaa ggttgtagga cttctgaaaa gacagaacta gctttgttgc    65700
gtttcacgaa ggacagatca gttcgtctgt ataggctata agcaggtaag tagtgcactc    65760
tattggtgaa ggatttctgt tgttttggaa agccaactat agctggctgc atggagggaa    65820
atccaaaatc cagatgacgt ggtgtgagtc aatgggatga gaaacactgg tattttcttt    65880
acaatttcat tttacaaaga gcacattaaa ctaaaattt atgaattatg acttaatcta    65940
atagttcaac agcagactca agaaaagcac agatgtgatt ctaacagaag actactcata    66000
taaacaggtt taatgcaaca tggaatgcaa aagattagaa ccattaaaat atttaattct    66060
tcaactttaa aaaattaaat aaaatcaaaa taggataatg accagaatag tgccattata    66120
atcacatcaa aaagcttcca ttaacatttt atgaatttgg caatctagta caatacatta    66180
agtattgtgt ttcactcaat tttgtgatac tccattttttg aaaaaactta gaggcttcag    66240
atacccatga aaagaaaaaa atcagggtag aaacacatag gctgaggttt gctaattcac    66300
tgtttacaga ggaccttaga tgtcccacta taattgctct taggtatttt taacaaatga    66360
atagtcataa ttcacagaaa agacaagtgg tactttttat ctacatagac tatactatat    66420
aaactttcag taaaacattt aaattgtttt acttttaatc ttgtcaagta attttcattt    66480
cttctacttc aaaaggttga ccaggttgtt tgcctgtatt gggatcaacg aatgttggac    66540
tatactatgt ttagttataa taactaattt atccaccctg acttaatatg tgggaaacaa    66600 tacacccta agtgtattga gatgtttctt tgaaacaaaa atatttaatt ttatgcatgt    66660
gataaacagc cttattcaat gtatactttt tttaaatgag caacacagat agcagacata    66720
taactcctta ttacccatac tcttgactac caagaaagga agccaaactt ttagaaaaat    66780
acaatgcaag aaaagattca agttaaaaat atattccttt ggttaaaaat catcccttt    66840 ataatattca tttgtaatct aaattcacag catgtcccac cagcccaaag taatcttcta    66900
aatgtcatta tacttgtagt attacaatgt ttttcagtc cagtatttat ggaggtcact    66960
cggctgcagc aacaaaatat ttcaactcta ggaagagtgt agccttgtag cattagcccc    67020
```

```
tttgacaatt ttcttacaag atttttactt tagaaacctc cgacacatgt agttttcttc   67080
agatacagta tatccaaact ttttatagaa accaacattt tgtggtagac attcaagggt   67140
aatcttgtaa cagttcagtt tcttgcttag caaagtaagg gttgataata acctgaaatt   67200
taaaaagggg gtagggtgag gagatagcat ttattaataa aaattgattc tagtaacaat   67260
atgaattaat gttataaaac ttaagtttcc ttagaaacag gtttagatta tggcttttcc   67320
cactgcattc atgtaagttg ataagcattt aaatcaccaa agcatttta cttagagtca   67380 aatatacttt tatctagtaa tctccagctc actaataaac aggacaaata caaaactcac   67440
cctaagccct ctttaaaaat gaaatttaag gctaggtgca gtgactcata cctgtaatcc   67500
tagcactctg ggaagccgag gcaggcgatc gctagagccc aggggtttga caccagcctg   67560
ggaaacacgg caaaccccca tctctacaaa atataaaaat tagtagggca tgatggcaca   67620
tgcctaaagt cgcagctact ccagaggctg agggggaag atcacctgag cccagagagg   67680
tcaaggctgc ggtgagtagt gattgtgcca ctgcactcca gcctgggcaa cagagtgagt   67740
ctctgtcttg aaaagaaaa acgaatttta agatgcatgt taacactaaa aactcaacct   67800
ttaaaaaaaa aaatgaccaa aattattttg taaaaattct ttatttaaat ctatttaaac   67860
aacttcggag cagtcgacat acccacataa aatgagtaca taatagcttt gctctttaat   67920 cattttaaa gctactttaa tatttgtgaa ggtgtgtatc agattaactc aagattggtc   67980
taattaatat gaagtggaaa caaagcaagt ctacatctat acaaaatttc ttaatgaatc   68040
caaacccagt attaaagtgt ggatctaagt gccttagagg ataaaaacta taaagatat   68100 acaaacttga agggtctgcc catgtttgaa cagactaaaa aatcctattt ttaaaaaaaa   68160
caaaagacct tgactgaagt atgcctggct ggttgcagtg gctcatgcct gtaattccag   68220
cactttagga ggccaaggat cacttgagtc cagaagttcg agactagcca aagcaacata   68280
gcaaaaccct atctctataa aaaattagct gggtgcagcg gcatgcacct gtagtcccag   68340
ctacttggga ggctgaggcg agaggctcac ttgagcccca gaaattcaag gctgcagtga   68400
gctgtgatcg taccactgta tactccagcc tgggcaacag aaagagatcc catctcttaa   68460 aaaaaaaaa aaaaaaaaaa aaaaacataa attatataga ctagaacaca agaaatcggt   68520
ctgttttgtt cactgaggta ttccaaatac ctagaatagc atctggtaca taagcaggta   68580
tttaatattt gttaattcct taaaactcag aagagttagt gttaaaaagc aagttcttgg   68640
gccaggcaca gtggctccca cctgtaatcc cagcactttg ggaggccaag gcaggagcac   68700
tgtttgagac cagcctgagc aacatgatga ggccccatct ctacaaattt ttaaaaatta   68760
gccaggtgtg gcgtgtacct gtagtcccag ctaattgggg ggctgaagag gattgcttga   68820
gcccaggagg ctgaggctgc agtgagctga gattgagcca ctgcacctca gcctgggtga   68880
cagagctgtc aaaacagac cctgtctcaa aaactaaaaa ttataataaa taagaactac   68940
aagttcttat aaaatggcaa taaatcaata ccacttattt atatttattt taaatgattt   69000
agatatatac agtgaaggct gtttcagtat gtatttctac aacttatgag aatgagagat   69060
cacagaatat tctgtaatag ttgaacattt cctttgtttt taaatatgac agagaagctg   69120
aggcaaatcc gattagccca aaagtttatc tcctactagg acgagagcat tactataaaa   69180
agttagtaat ttaaagatgt tactgtctgt aaagaagtat gcttccaatt ttcaaacttt   69240
aaggcaaaat atgtataata atactttatt tcttcatgaa attcagtcta aactattaga   69300
gtgagaataa gttcagaatt aatgaagcca aaagaactt caaacaagta tcttgttaag   69360
```

```
aaactaaatt ggaacaaaat ttatccaggg ttaccttgtt tctgcctact tacaatttgc   69420
caagctgctt tcctctgcat tcatcactaa caacaacatc ttctactctt cctctctgaa   69480
aatatttaca atgtttaaag gagtaagcat ttacttttgt ttttagctaa aacgagttgg   69540
taagaattta ctgataataa gtagtatatt ttgtaaactt gaacttaaca gaaatcaaat   69600
gcaaaaaata ttatacagtg aaggctgttt cagtatgtat ttctacaact tatgagaagg   69660
agagatcata gaatattctg taatagctga acatttcctt tgttttttaaa tatgacagag   69720 aagctggggc aaatctgatt agcccaaaag tttgtttcct actagtatga gagtactact   69780
attaaaagtt aataatttaa agatgttttt acttattaga ggaaatagta tgagtcaagt   69840
tgtgacctaa acttgttttg gctatgtccc caaccttccc accccattgt ctttaaacaa   69900
atatcaggat caacatcacc aaaatgtaac cttttcatga atatatccat cattctactc   69960
cttgcttact agcaagttat tttagatatc caaataaaat taatgtctag tacagaaacc   70020
ccaccgaaat tcctaagtgt gacagaacac atcccaagtg ttcctacctt attctcattg   70080
aattaaggtt ttctctccct cttttttat ttactatttt atgtgagtta ttgagggatg   70140
aaagggcact acatgcatta gatgtatcat aattagaacg gaataatctg aacccttta c   70200 catgtggaaa caaatttatg ctaacgtggt atattcagag ttgtttttttt taaaagagta   70260 acattaggga ttttgtgcat tactgctaag ttgtttggtt tctctatgcc tataccaaat   70320
tgatccacct tacagaacaa ttttagcata caattcatac tgttatacat tttctttctt   70380
aaagctctca gaacacactg ggaaaaggga tttctaagag gcactgaaaa tcaatgagaa   70440
aacagatttg tctaatggaa actcaaagtc agttgtgcta gaaaacagct gtccattta    70500 tttataagca gcacatacct tagcacagga atggatgaat ttatgttcta taatcagagt   70560
tgccgtagca acaatctgtc ctagagtcac atcttctaca actgtaacat aataatcccc   70620
agatttcttc atatgctcaa aagattctgt ggaaattgga taacaaagtg ttacatagta   70680
gacattcaat tttatgggga gccagaaaaa tattaggatt agctgactta attactaaat   70740
gtttaaagct gttttaccat agtaatttac cttccatttc taaagaaaat attaccaagt   70800
agttgaaata tcagcaatta gtatcaattg gaatataacc tacacattca aaatatctgc   70860
tagcaaaata aagactaata tagctatttt agatgaacaa cacttaaaat acaagtaaat   70920
ggctgatgtt gccacttcca tgactaatga aaacttcaat ttcttcattt actttaaata   70980
gatctcttta acttttatac tcaatagata ttcaaatata acctttgcac attttaacaa   71040
gagcatgttt acatggctca attctagaat ttttagtctt ttgctttcaa aatatttta   71100 caaaatatat tttaatttc ccttttgtgat ggaaagtgtt ttgtgataac atgacttgct   71160
cttgtttgct ttgagagcac cttgcaagga agtaaaaaca tatctgtttc caagtaactt   71220
ttccaagtca catagcaaat aggtgcaaag atacttcccc tcaaatggat tttcagtact   71280
attgctgaaa taacatggtt tctcatctaa ttcatgtgca tgcaaagaaa aaattcagga   71340
ataaaaattg aggctaatag tctctcatat tggtaatttc ctatgggggcc tcattccaga   71400 tagagatcta aaatgggaaa aagaaattca gtgaatgaaa ataaacaatg agtaatcagt   71460
aatgatggtc ctcattctca ggagggtcaa atagcaattc aatacaaaat tccctattat   71520
aaggaaatga agaattgtaa ttcctcagct attaaatatt actaaatatt tagtaatgat   71580
aataatactt catttccttt ataacaggaa aaagcagtgg tagagcactg gacagaatta   71640
aggttttatt cctcaccgta gcaataacta cctgtgatct tgggcaagtc tttggatctc   71700
tctaaattcc tattttctcc tatgtctaaa agaagagggg caggggacgg gtggactaac   71760
```

```
tcttaagatg cctgctaacc ttaaacttca atacaaataa accccaaaat aaatttaaag    71820
cgtatagtct tgcttttttg atttggtaat gaaatttctg taaataacca cagtaaggga    71880
aatactacaa taaaaaaacg aaaaacctct agagctaaca cctaggtcct atggtacaat    71940
aattatctaa taaagtagtc agatagtttg caaaaacaaa gttactggta catttggatt    72000
ctagaacaac tcagccacat taaacatttg tataaaacag ctaatttgtt ctttgaataa    72060
tttccagcta tttgaacaaa acagaagtg ggcactgaac agctctaaac aaaaatgaaa    72120
tcatgtttcc ctttatttca ggaaaagag gttatagtac ttactcataa attgttcagg     72180
gctgacaact ccagtctctg ttagctgacc caataccta aaaaaccta gttttgaaaa      72240 acagatttca aattacgaga atagcaaaag gaagacagta tgaaaataag caatatatta    72300
agcaggtggg cttacaggca attattttt cagaactttc tataatcttt taattattag     72360
aataaagtga accctattct tctataatca ctacatataa caaaaataac aggttttacc    72420
agtgcttctg cctgcataag atgttttaaa tagtgctgac cttaatatcc agtatttata    72480
gacccagaac atacattctt caatgtatta tattttacat taagttcaat gcaaagggtg    72540
ccagattttc ccaaatatgt gatttggttt tacttaaagg tgcaacatgg ctaaatacaa    72600
tattcgtaaa ttaaagtata agtaacactg ttgagattac actctttaaa attgtaattt    72660
ctagtgaatt tcattagtgt taccggaaat tgatgtgaac agtgcacctg gaattttgaa    72720
aatcttaact ttcctacact caataattag gccaaaatta ggcccttcag gctgtctagc    72780
aaagagataa ttgtgaaaag gacaaagttg acttttaatt accaaagttt aaggaagtta    72840
acttggagaa tttagatgtt aaaaagaaa taactgtata aaaacccttt caatttatcc      72900
aaggaaaatt atttccacct tcattcccca accagcttct taagatccct ccttatgtgt    72960
catcatacat gataatttaa ttttttgttta tgagaaatct ttttggctta attaggaagg    73020
agtgatgttg tatttaagtc atttttaaata tttcacagta atatttggtc ttagccatga    73080
cacacactca ttggtattga gtgtccatca ctttaaaaac taagtattat acaaaaaata    73140
gtccaaaagt caaatattta aaaaaaatta tctgcatcat aatgtttaga gaaaatggaa    73200
aggctaactc taattttaca caggattttg tacattacct ctatttaagt cagcagtaca    73260
aagaggcctc aaaaccaagc cttctccagg atgtgttggg gaaatggctg gagaaaatgt    73320
agctgtattc tgactccagt ccacttcttt gagtagactt gggtcaaaca taggagtttc    73380
atcaggtttc attttttctag taaggtctaa aataaaaatt tgaatattaa gtcacttat     73440 ttaatagaag gaaaattatg attgttgaga aagttaatat aaattaatgc aattagaagc    73500
attctttagc acatatgcga gatattttac tgcaacccag cctgaatcta acattaaatt    73560
ccacaactac agataaatag aaaaatcatg cctactatca gataaaaaaa tggctaagtg    73620
actaaattag taagttttaa actataaaat cccatttatt atcaagtctt ttttttttt     73680 ttttttcag acagtctcac tctgttgccc aggctggagt gcagaggcgt gatcccggct     73740
cactgcaacc tctgccttct gggttcaagt gattctcctc tttcagcctc ctgagtatct    73800
gggattatag gcacgtgaca ccacgcccgg ctaattttt tgtattttta atagagacgg     73860
gatttcgccg tgttagccag gctggtctca aactcccgac ctcaggtgat ctgcccgcct    73920
cggcctccca aagtgctggg attacaggcg tgagccactg cgcccggcta gtatcaggtc    73980
ttttaaaaca tgttttttcct ctgggttggt gctactaaat gaatagctga cttttcatgg    74040
gctcttaaat tttttacatt atgttcttgg attttattat tgagccaaga aggcatctgt    74100
```

```
                                          -continued
ttcaacagga aattgcaagg ggaaaaaaat tttttttaaa aaagtaatct cttagtctta   74160
cttgccaata aagaaaactt tcagctgtgc acggtggctc acacctgtaa taccaacact   74220
ttgggaggcc gaggtgggca gatcacctga ggtcgggagt tcgagaccag cctgaccaac   74280
atggagaaac ccccatctct actaaaaata caaaattagt ccgggcgtgg gggtataccg   74340
cgtgtaaact tattttccat ctatgatgaa aagttaagaa tattctgccc tacagcatac   74400
tgtgacttat gaaataagga acaattgggg gttaggttat tgggcaaatt ggtctctcat   74460
taaaatatgg tttctttaac tggatataga aataagttgg ggactgcttt ttttggatct   74520
ctaatccaaa aatccaaaac actccaaaat tttgaaactt tattgagggg ccaacatgat   74580
tgccacaagt ggaaaattcc acatctggta taatggacaa aaacttttcc atgcacaaaa   74640
ttattttaaa atattggggt aaaatatttg ggctatctgg ataagatgta tatgaaacac   74700
aaatggaatt ttgactttgg gtcccatccc caagatattc ttcattatgt atattgaaaa   74760
tattccccaa atctggaaat atatcctatt tttgaaatac attatgtgtt tccaaaacct   74820
tgaaacattt tttgggccca aactttggga taaggaatac tcaacttttta atttgttggg   74880 aagctttgtt ttttaaacat ttttgggctg gaaaaaagcc ccctggcccc aaatttatcc   74940
ctttgaatga attggtttat cc                                          74962
```

US 6,479,270 B1

ISOLATED HUMAN PHOSPHATASE PROTEINS, NUCLEIC ACID MOLECULES ENCODING HUMAN PHOSPHATASE PROTEINS, AND USES THEREOF

RELATED APPLICATIONS

The present application claims priority to provisional application U.S. Ser. No. (60/182,194), filed Feb. 14, 2000.

FIELD OF THE INVENTION

The present invention is in the field of phosphatase proteins that are related to the protein tyrosine phosphatase subfamily, recombinant DNA molecules and protein production. The present invention specifically provides novel protein tyrosine phosphatase peptides and proteins and nucleic acid molecules encoding such peptide and protein molecules, all of which are useful in the development of human therapeutics and diagnostic compositions and methods.

BACKGROUND OF THE INVENTION

Phosphatase proteins, especially the member of protein tyrosine phosphatase subfamily, are a major target for drug action and development. Accordingly, it is valuable to the field of pharmaceutical development to identify and characterize previously unknown members protein tyrosine phosphatase subfamily. The present invention advances the state of the art by providing a previously unidentified human phosphatase proteins that have homology to members of the protein tyrosine phosphatase subfamily.

Protein Phosphatase

Cellular signal transduction is a fundamental mechanism whereby external stimuli that regulate diverse cellular processes are relayed to the interior of cells. The biochemical pathways through which signals are transmitted within cells comprise a circuitry of directly or functionally connected interactive proteins. One of the key biochemical mechanisms of signal transduction involves the reversible phosphorylation of certain residues on proteins. The phosphorylation state of a protein may affect its conformation and/or enzymic activity as well as its cellular location. The phosphorylation state of a protein is modified through the reciprocal actions of protein phosphatases (PKs) and protein phosphatases (PPs) at various specific amino acid residues.

Protein phosphorylation is the ubiquitous strategy used to control the activities of eukaryotic cells. It is estimated that 10% of the proteins active in a typical mammalian cell are phosphorylated. The high-energy phosphate that confers activation and is transferred from adenosine triphosphate molecules to protein-by-protein phosphatases is subsequently removed from the protein-by-protein phosphatases. In this way, the phosphatases control most cellular signaling events that regulate cell growth and differentiation, cell-to-cell contacts, the cell cycle, and oncogenesis.

The protein phosphorylation/dephosphorylation cycle is one of the major regulatory mechanisms employed by eukaryotic cells to control cellular activities. It is estimated that more than 10% of the active proteins in a typical mammalian cell are phosphorylated. During protein phosphorylation/dephosphorylation, phosphate groups are transferred from adenosine triphosphate molecules to protein-by-protein phosphatases and are removed from the protein-by-protein phosphatases.

Protein phosphatases function in cellular signaling events that regulate cell growth and differentiation, cell-to-cell contacts, the cell cycle, and oncogenesis. Three protein phosphatase families have been identified as evolutionarily distinct. These include the serine/threonine phosphatases, the protein tyrosine phosphatases, and the acid/alkaline phosphatases (Carbonneau H. and Tonks N. K. (1992) Annu. Rev. Cell Biol. 8:463–93).

The serine/threonine phosphatases are either cytosolic or associated with a receptor. On the basis of their sensitivity to two thermostable proteins, inhibitors 1 and 2, and their divalent cation requirements, the serine/threonine phosphatases can be separated into four distinct groups, PP-I, PP-IIA, PP-IIB, and PP-IIC.

PP-I dephosphorylates many of the proteins phosphorylated by cylic AMP-dependent protein phosphatase and is therefore an important regulator of many cyclic AMP mediated, hormone responses in cells. PP-IIA has broad specificity for control of cell cycle, growth and proliferation, and DNA replication and is the main phosphatase responsible for reversing the phosphorylations of serine/threonine phosphatases. PP-IIB, or calcineurin (Cn), is a $Ca^{+2}$-activated phosphatase; it is involved in the regulation of such diverse cellular functions as ion channel regulation, neuronal transmission, gene transcription, muscle glycogen metabolism, and lymphocyte activation.

PP-IIC is a $Mg^{++}$-dependent phosphatase which participates in a wide variety of functions including regulating cyclic AMP-activated protein-phosphatase activity, $Ca^{++}$-dependent signal transduction, tRNA splicing, and signal transmission related to heat shock responses. PP-IIC is a monomeric protein with a molecular mass of about 40–45 kDa. One alpha. and several .beta. isoforms of PP-IIC have been identified (Wenk, J. et al. (1992) FEBS Lett. 297: 135–138; Terasawa, T. et al. (1993) Arch. Biochem. Biophys. 307: 342–349; and Kato, S. et al. (1995) Arch. Biochem. Biophys. 318: 387–393).

The levels of protein phosphorylation required for normal cell growth and differentiation at any time are achieved through the coordinated action of PKs and PPS. Depending on the cellular context, these two types of enzymes may either antagonize or cooperate with each other during signal transduction. An imbalance between these enzymes may impair normal cell functions leading to metabolic disorders and cellular transformation.

For example, insulin binding to the insulin receptor, which is a PTK, triggers a variety of metabolic and growth promoting effects such as glucose transport, biosynthesis of glycogen and fats, DNA synthesis, cell division and differentiation. Diabetes mellitus, which is characterized by insufficient or a lack of insulin signal transduction, can be caused by any abnormality at any step along the insulin signaling pathway. (Olefsky, 1988, in "Cecil Textbook of Medicine," 18th Ed., 2:1360–81).

It is also well known, for example, that the overexpression of PTKs, such as HER2, can play a decisive role in the development of cancer (Slamon et al., 1987, Science 235:77–82) and that antibodies capable of blocking the activity of this enzyme can abrogate tumor growth (Drebin et al., 1988, Oncogene 2:387–394). Blocking the signal transduction capability of tyrosine phosphatases such as Flk-1 and the PDGF receptor have been shown to block tumor growth in animal models (Millauer et al., 1994, Nature 367:577; Ueno et al., Science, 252:844–848).

Relatively less is known with respect to the direct role of phosphatases in signal transduction; PPs may play a role in human diseases. For example, ectopic expression of RPT-P.alpha. produces a transformed phenotype in embryonic fibroblasts (Zheng et al., Nature 359:336–339), and overexpression of RPTP.alpha. in embryonal carcinoma cells causes the cells to differentiate into a cell type with neuronal phenotype (den Hertog et al., EMBO J 12:3789–3798). The gene for human RPTP.gamma. has been localized to chromosome 3p21 which is a segment frequently altered in renal and small lung carcinoma. Mutations may occur in the extracellular segment of RPTP.gamma. which renders a RPTP that no longer respond to external signals (LaForgia et al., Wary et al., 1993, Cancer Res 52:478–482). Mutations in the gene encoding PTP1C (also known as HCP, SHP) are the cause of the moth-eaten phenotype in mice that suffer severe immunodeficiency, and systemic autoimmune disease accompanied by hyperproliferation of macrophages (Schultz et al., 1993, Cell 73:1445–1454). PTP1D (also known as Syp or PTP2C) has been shown to bind through SH2 domains to sites of phosphorylation in PDGFR, EGFR and insulin receptor substrate 1 (IRS-1). Reducing the activity of PTPID by microinjection of anti-PTPI D antibody has been shown to block insulin or EGF-induced mitogenesis (Xiao et al., 1994, J Biol Chem 269:21244–21248).

The discovery of a new human protein phosphatase and the polynucleotides encoding it satisfies a need in the art by providing new compositions that are useful in the diagnosis, prevention and treatment of biological processes associated with abnormal or unwanted protein phosphorylation.

The phosphatase gene of the present invention can be expressed in yeast to identify possible interactors and substrates; this can be done by means of a complementation assay or a two-hybrid experiment. Artificially synthesized enzyme as well as derived peptides can be used to activate or inhibit cellular processes modulated by this phosphatase. Immunoassay or PCR may be used to measure the concentration of this protein and detect abnormally developing tissue or cancerous growth.

For a review of the phosphatase associated with the present invention see Wishart et al., *J Biol Chem* 1995 November 10;270(45):26782–5, Bjorge et al., *J Biol Chem* 2000 September 27; Harroch et al., *Mol Cell Biol* 2000 October;20(20):7706–15, Beghini et al., *Hum Mol Genet* 2000 September 22;9(15):2297–2304, Waddleton et al., *Anal Biochem* 2000 October 1;285(1):58–63.

SUMMARY OF THE INVENTION

The present invention is based in part on the identification of amino acid sequences of human phosphatase peptides and proteins that are related to the protein tyrosine phosphatase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate phosphatase activity in cells and tissues that express the phosphatase. Experimental data as provided in FIG. 1 indicates expression in the human total fetus, human germinal B cell, human fetal liver, human fetal liver spleen and human lymph node, as well as expression in human fetal brain, human brain, human heart, human liver, human lung, human placenta, and human thyroid tissues.

DESCRIPTION OF THE FIGURE SHEETS

FIG. 1 provides the nucleotide sequence of a cDNA molecule or transcript sequence that encodes the phosphatase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in the human total fetus, human germinal B cell, human fetal liver, human fetal liver spleen and human lymph node, as well as expression in human fetal brain, human brain, human heart, human liver, human lung, human placenta, and human thyroid tissues.

FIG. 2 provides the predicted amino acid sequence of the phosphatase of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the phosphatase protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, known SNP variations include G3114A, T4514G, A7570G, C11672G, A11897C, T14523C, C16586T, T16644C, A17969G, C18117T, C18518A, G19882A, A21465G, C21625T, C26291T, T28012C, T28030G, A33671C, A37703G, C39269G, -20999T, -4004A, and G20988-.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a phosphatase protein or part of a phosphatase protein and are related to the protein tyrosine phosphatase subfamily. Utilizing these sequences, additional genomic sequences were assembled and transcript and/or cDNA sequences were isolated and characterized. Based on this analysis, the present invention provides amino acid sequences of human phosphatase peptides and proteins that are related to the protein tyrosine phosphatase subfamily, nucleic acid sequences in the form of transcript sequences, cDNA sequences and/or genomic sequences that encode these phosphatase peptides and proteins, nucleic acid variation (allelic information), tissue distribution of expression, and information about the closest art known protein/peptide/domain that has structural or sequence homology to the phosphatase of the present invention.

In addition to being previously unknown, the peptides that are provided in the present invention are selected based on their ability to be used for the development of commercially important products and services. Specifically, the present peptides are selected based on homology and/or structural relatedness to known phosphatase proteins of the protein tyrosine phosphatase subfamily and the expression pattern observed. Experimental data as provided in FIG. 1 indicates expression in the human total fetus, human germinal B cell, human fetal liver, human fetal liver spleen and human lymph node, as well as expression in human fetal brain, human brain, human heart, human liver, human lung, human placenta, and human thyroid tissues. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known phosphatase family or subfamily of phosphatase proteins.

Specific Embodiments

Peptide Molecules

The present invention provides nucleic acid sequences that encode protein molecules that have been identified as being members of the phosphatase family of proteins and are related to the protein tyrosine phosphatase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the phosphatase peptides of the present invention, phosphatase peptides, or peptides/proteins of the present invention.

The present invention provides isolated peptide and protein molecules that consist of, consist essentially of, or comprise the amino acid sequences of the phosphatase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the phosphatase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated phosphatase peptide can be purified from cells that naturally express it, purified from cells that have been altered to express it (recombinant), or synthesized using known protein synthesis methods. Experimental data as provided in FIG. 1 indicates expression in the human total fetus, human germinal B cell, human fetal liver, human fetal liver spleen and human lymph node, as well as expression in human fetal brain, human brain, human heart, human liver, human lung, human placenta, and human thyroid tissues. For example, a nucleic acid molecule encoding the phosphatase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the phosphatase peptides of the present invention are the naturally occurring mature proteins. A brief description of how various types of these proteins can be made/isolated is provided below.

The phosphatase peptides of the present invention can be attached to heterologous sequences to form chimeric or fusion proteins. Such chimeric and fusion proteins comprise a phosphatase peptide operatively linked to a heterologous protein having an amino acid sequence not substantially homologous to the phosphatase peptide. "Operatively linked" indicates that the phosphatase peptide and the heterologous protein are fused in-frame. The heterologous protein can be fused to the N-terminus or C-terminus of the phosphatase peptide.

In some uses, the fusion protein does not affect the activity of the phosphatase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant phosphatase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al, *Current Protocols in Molecular Biology,* 1992). Moreover, many expression vectors are commercially available that already encode a fusion moiety (e.g., a GST protein). A phosphatase peptide-encoding nucleic acid can be cloned into such an expression vector such that the fusion moiety is linked in-frame to the phosphatase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the phosphatase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology,* Lesk, A. M., ed., Oxford University Press, New York, 1988; *Biocomputing; Informatics and Genome Projects,* Smith, D. W., ed., Academic Press, N.Y., 1993; *Computer Analysis of Sequence Data, Part 1,* Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the phosphatase peptides of the present invention as well as being encoded by the same genetic locus as the phosphatase peptide provided herein. As indicated by the data presented in FIG. 3, the map position was determined to be on chromosome 14 by ePCR, and confirmed with radiation hybrid mapping. As indicated by the data presented in FIG. 3, the gene provided by the present invention encoding a novel phosphatase maps to public BAC AC AL139317.2, which is known to be located on human chromosome 14.

Allelic variants of a phosphatase peptide can readily be identified as being a human protein having a high degree (significant) of sequence homology/identity to at least a portion of the phosphatase peptide as well as being encoded by the same genetic locus as the phosphatase peptide provided herein. Genetic locus can readily be determined based on the genomic information provided in FIG. 3, such as the genomic sequence mapped to the reference human. As indicated by the data presented in FIG. 3, the map position was determined to be on chromosome 14 by ePCR, and confirmed with radiation hybrid mapping. As indicated by the data presented in FIG. 3, the gene provided by the present invention encoding a novel phosphatase maps to public BAC AC AL139317.2, which is known to be located on human chromosome 14. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a phosphatase peptide encoding nucleic acid molecule under stringent conditions as more fully described below.

FIG. 3 provides SNP information that has been found in a gene encoding the phosphatase protein of the present invention. The following variations were seen: G3114A, T4514G, A7570G, C11672G, A11897C, T14523C, C16586T, T16644C, A17969G, C18117T, C18518A, G19882A, A21465G, C21625T, C26291T, T28012C, T28030G, A33671C, A37703G and C39269G as substitutions, -20999T, -4004A as insertions and G20988- deletion. The changes in the amino acid sequence that these SNPs cause can readily be determined using the universal genetic code and the protein sequence provided in FIG. 2 as a base.

Paralogs of a phosphatase peptide can readily be identified as having some degree of significant sequence homology/identity to at least a portion of the phosphatase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a phosphatase peptide encoding nucleic acid molecule under moderate to stringent conditions as more fully described below.

Orthologs of a phosphatase peptide can readily be identified as having some degree of significant sequence homology/identity to at least a portion of the phosphatase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a phosphatase peptide encoding nucleic acid molecule under moderate to stringent conditions, as more fully described below, depending on the degree of relatedness of the two organisms yielding the proteins.

Non-naturally occurring variants of the phosphatase peptides of the present invention can readily be generated using recombinant techniques. Such variants include, but are not limited to deletions, additions and substitutions in the amino acid sequence of the phosphatase peptide. For example, one class of substitutions are conserved amino acid substitution. Such substitutions are those that substitute a given amino acid in a phosphatase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., Science 247:1306–1310 (1990).

Variant phosphatase peptides can be fully functional or can lack function in one or more activities, e.g. ability to bind substrate, ability to dephosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., Science 244:1081–1085 (1989)), particularly using the results provided in FIG. 2. The latter procedure introduces single alanine mutations at every residue in the molecule. The resulting mutant molecules are then tested for biological activity such as phosphatase activity or in assays such as an in vitro proliferative activity. Sites that are critical for binding partner/substrate binding can also be determined by structural analysis such as crystallization, nuclear magnetic resonance or photoaffinity labeling (Smith et al., J. Mol. Biol. 224:899–904 (1992); de Vos et al. Science 255:306–312 (1992)).

The present invention further provides fragments of the phosphatase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a phosphatase peptide. Such fragments can be chosen based on the ability to retain one or more of the biological activities of the phosphatase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the phosphatase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in phosphatase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of proteins,* B. C. Johnson, Ed., Academic Press, New York 1–12 (1983); Seifter et al. (*Meth. Enzymol* 182: 626–646 (1990)) and Rattan et al. (*Ann. N.Y. Acad. Sci.* 663:48–62 (1992)).

Accordingly, the phosphatase peptides of the present invention also encompass derivatives or analogs in which a substituted amino acid residue is not one encoded by the genetic code, in which a substituent group is included, in which the mature phosphatase peptide is fused with another compound, such as a compound to increase the half-life of the phosphatase peptide, or in which the additional amino acids are fused to the mature phosphatase peptide, such as a leader or secretory sequence or a sequence for purification of the mature phosphatase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a phosphatase-effector protein interaction or phosphatase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, phosphatases isolated from humans and their human/mammalian orthologs serve as targets for identifying agents for use in mammalian therapeutic applications, e.g. a human drug, particularly in modulating a biological or pathological response in a cell or tissue that expresses the phosphatase. Experimental data as provided in FIG. 1 indicates that phosphatase proteins of the present invention are expressed in the human brain, heart and liver etc. Specifically, a virtual northern blot shows expression in human total fetus, human germinal B cell, human fetal liver, human fetal liver spleen and human lymph node. In addition, PCR-based tissue screening panel indicates expression in human fetal brain, human brain, human heart, human liver, human lung, human placenta, and human thyroid. A large percentage of pharmaceutical agents are being developed that modulate the activity of phosphatase proteins, particularly members of the protein tyrosine phosphatse subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in the human total fetus, human germinal B cell, human fetal liver, human fetal liver spleen and human lymph node, as well as expression in human fetal brain, human brain, human heart, human liver, human lung, human placenta, and human thyroid tissues. Such uses can readily be determined using the information provided herein, that which is known in the art, and routine experimentation.

The proteins of the present invention (including variants and fragments that may have been disclosed prior to the present invention) are useful for biological assays related to phosphatases that are related to members of the protein tyrosine phosphatse subfamily. Such assays involve any of the known phosphatase functions or activities or properties useful for diagnosis and treatment of phosphatase-related conditions that are specific for the subfamily of protein tyrosine phosphatases that the one of the present invention belongs to, particularly in cells and tissues that express the phosphatase. Experimental data as provided in FIG. 1 indicates that phosphatase proteins of the present invention are expressed in the human brain, heart and liver etc. Specifically, a virtual northern blot shows expression in human total fetus, human germinal B cell, human fetal liver, human fetal liver spleen and human lymph node. In addition, PCR-based tissue screening panel indicates expression in human fetal brain, human brain, human heart, human liver, human lung, human placenta, and human thyroid.

The proteins of the present invention are also useful in drug screening assays, in cell-based or cell-free systems. Cell-based systems can be native, i.e., cells that normally express the phosphatase, as a biopsy or expanded in cell culture. Experimental data as provided in FIG. 1 indicates expression in the human total fetus, human germinal B cell, human fetal liver, human fetal liver spleen and human lymph node, as well as expression in human fetal brain, human brain, human heart, human liver, human lung, human placenta, and human thyroid tissues. In an alternate embodiment, cell-based assays involve recombinant host cells expressing the phosphatase protein.

The polypeptides can be used to identify compounds that modulate phosphatase activity of the protein in its natural state or an altered form that causes a specific disease or pathology associated with the phosphatase. Both the phosphatases of the present invention and appropriate variants and fragments can be used in high-throughput screens to assay candidate compounds for the ability to bind to the phosphatase. These compounds can be further screened against a functional phosphatase to determine the effect of the compound on the phosphatase activity. Further, these compounds can be tested in animal or invertebrate systems to determine activity/effectiveness. Compounds can be identified that activate (agonist) or inactivate (antagonist) the phosphatase to a desired degree.

Further, the proteins of the present invention can be used to screen a compound for the ability to stimulate or inhibit interaction between the phosphatase protein and a molecule that normally interacts with the phosphatase protein, e.g. a substrate or a component of the signal pathway that the phosphatase protein normally interacts (for example, another phosphatase). Such assays typically include the steps of combining the phosphatase protein with a candidate compound under conditions that allow the phosphatase protein, or fragment, to interact with the target molecule, and to detect the formation of a complex between the protein and the target or to detect the biochemical consequence of the interaction with the phosphatase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant phosphatases or appropriate fragments containing mutations that affect phosphatase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) phosphatase activity. The assays typically involve an assay of events in the signal transduction pathway that indicate phosphatase activity. Thus, the dephosphorylation of a substrate, activation of a protein, a change in the expression of genes that are up- or down-regulated in response to the phosphatase protein dependent signal cascade can be assayed.

Any of the biological or biochemical functions mediated by the phosphatase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the phosphatase can be assayed. Experimental data as provided in FIG. 1 indicates that phosphatase proteins of the present invention are expressed in the human brain, heart and liver etc. Specifically, a virtual northern blot shows expression in human total fetus, human germinal B cell, human fetal liver, human fetal liver spleen and human lymph node. In addition, PCR-based tissue screening panel indicates expression in human fetal brain, human brain, human heart, human liver, human lung, human placenta, and human thyroid.

Binding and/or activating compounds can also be screened by using chimeric phosphatase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native phosphatase. Accordingly, a different set of signal transduction components is available as an end-point assay for activation. This allows for assays to be performed in other than the specific host cell from which the phosphatase is derived.

The proteins of the present invention are also useful in competition binding assays in methods designed to discover compounds that interact with the phosphatase (e.g. binding partners and/or ligands). Thus, a compound is exposed to a phosphatase polypeptide under conditions that allow the compound to bind to or to otherwise interact with the polypeptide. Soluble phosphatase polypeptide is also added to the mixture. If the test compound interacts with the soluble phosphatase polypeptide, it decreases the amount of complex formed or activity from the phosphatase target. This type of assay is particularly useful in cases in which compounds are sought that interact with specific regions of the phosphatase. Thus, the soluble polypeptide that competes with the target phosphatase region is designed to contain peptide sequences corresponding to the region of interest.

To perform cell free drug screening assays, it is sometimes desirable to immobilize either the phosphatase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of phosphatase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a phosphatase-binding protein and a candidate compound are incubated in the phosphatase protein-presenting wells and the amount of complex trapped in the well can be quantitated. Methods for detecting such complexes, in addition to those described above for the GST-immobilized complexes, include immunodetection of complexes using antibodies reactive with the phosphatase protein target molecule, or which are reactive with phosphatase protein and compete with the target molecule, as well as enzyme-linked assays which rely on detecting an enzymatic activity associated with the target molecule.

Agents that modulate one of the phosphatases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of phosphatase protein activity identified according to these drug screening assays can be used to treat a subject with a disorder mediated by the kinase pathway, by treating cells or tissues that express the phosphatase. Experimental data as provided in FIG. 1 indicates expression in the human total fetus, human germinal B cell, human fetal liver, human fetal liver spleen and human lymph node, as well as expression in human fetal brain, human brain, human heart, human liver, human lung, human placenta, and human thyroid tissues. These methods of treatment include the steps of administering a modulator of phosphatase activity in a pharmaceutical composition to a subject in need of such treatment, the modulator being identified as described herein.

In yet another aspect of the invention, the phosphatase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the phosphatase and are involved in phosphatase activity. Such phosphatase-binding proteins are also likely to be involved in the propagation of signals by the phosphatase proteins or phosphatase targets as, for example, downstream elements of a kinase-mediated signaling pathway. Alternatively, such phosphatase-binding proteins are likely to be phosphatase inhibitors.

The two-hybrid system is based on the modular nature of most transcription factors, which consist of separable DNA-binding and activation domains. Briefly, the assay utilizes two different DNA constructs. In one construct, the gene that codes for a phosphatase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a phosphatase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the phosphatase protein.

This invention further pertains to novel agents identified by the above-described screening assays. Accordingly, it is within the scope of this invention to further use an agent identified as described herein in an appropriate animal model. For example, an agent identified as described herein (e.g., a phosphatase-modulating agent, an antisense phosphatase nucleic acid molecule, a phosphatase-specific antibody, or a phosphatase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The phosphatase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in the human total fetus, human germinal B cell, human fetal liver, human fetal liver spleen and human lymph node, as well as expression in human fetal brain, human brain, human heart, human liver, human lung, human placenta, and human thyroid tissues. The method involves contacting a biological sample with a compound capable of interacting with the phosphatase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered phosphatase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the phosphatase protein in which one or more of the phosphatase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and phosphatase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the human total fetus, human germinal B cell, human fetal liver, human fetal liver spleen and human lymph node, as well as expression in human fetal brain, human brain, human heart, human liver, human lung, human placenta, and human thyroid tissues. Accordingly, methods for treatment include the use of the phosphatase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or $F(ab')_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the phosphatase proteins. Antibodies can be prepared from any region of the peptide as described herein. However, preferred regions will include those involved in function/activity and/or phosphatase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, P-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that phosphatase proteins of the present invention are expressed in the human brain, heart and liver etc. Specifically, a virtual northern blot shows expression in human total fetus, human germinal B cell, human fetal liver, human fetal liver spleen and human lymph node. In addition, PCR-based tissue screening panel indicates expression in human fetal brain, human brain, human heart, human liver, human lung, human placenta, and human thyroid. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the human total fetus, human germinal B cell, human fetal liver, human fetal liver spleen and human lymph node, as well as expression in human fetal brain, human brain, human heart, human liver, human lung, human placenta, and human thyroid tissues. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the human total fetus, human germinal B cell, human fetal liver, human fetal liver spleen and human lymph node, as well as expression in human fetal brain, human brain, human heart, human liver, human lung, human placenta, and human thyroid tissues. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the human total fetus, human germinal B cell, human fetal liver, human fetal liver spleen and human lymph node, as well as expression in human fetal brain, human brain, human heart, human liver, human lung, human placenta, and human thyroid tissues. Thus, where a specific protein has been correlated with expression in a specific tissue, antibodies that are specific for this protein can be used to identify a tissue type.

The antibodies are also useful for inhibiting protein function, for example, blocking the binding of the phosphatase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a phosphatase peptide or protein of the present invention (cDNA, transcript and genomic sequence). Such nucleic acid molecules will consist of, consist essentially of, or comprise a nucleotide sequence that encodes one of the phosphatase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the phosphatase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the phosphatase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 14 by ePCR, and confirmed with radiation hybrid mapping. As indicated by the data presented in FIG. 3, the gene provided by the present invention encoding a novel phosphatase maps to public BAC AC AL139317.2, which is known to be located on human chromosome 14.

FIG. 3 provides SNP information that has been found in a gene encoding the phosphatase protein of the present invention. The following variations were seen: G3114A, T4514G, A7570G, C11672G, A11897C, T14523C, C16586T, T16644C, A17969G, C18117T, C18518A, G19882A, A21465G, C21625T, C26291T, T28012C, T28030G, A33671C, A37703G and C39269G as substitutions, -20999T, -4004A as insertions and G20988- deletion. The changes in the amino acid sequence that these SNPs cause can readily be determined using the universal genetic code and the protein sequence provided in FIG. 2 as a base.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6×sodium chloride/sodium citrate (SSC) at about 45 C., followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, known SNP variations include G3114A, T4514G, A7570G, C11672G, A11897C, T14523C, C16586T, T16644C, A17969G, C18117T, C18518A, G19882A, A21465G, C21625T, C26291T, T28012C, T28030G, A33671C, A37703G, C39269G, -20999T, -4004A, and G20988-.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 14 by ePCR, and confirmed with radiation hybrid mapping. As indicated by the data presented in FIG. 3, the gene provided by the present invention encoding a novel phosphatase maps to public BAC AC AL139317.2, which is known to be located on human chromosome 14.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that phosphatase proteins of the present invention are expressed in the human brain, heart and liver etc. Specifically, a virtual northern blot shows expression in human total fetus, human germinal B cell, human fetal liver, human fetal liver spleen and human lymph node. In addition, PCR-based tissue screening panel indicates expression in human fetal brain, human brain, human heart, human liver, human lung, human placenta, and human thyroid. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in phosphatase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a phosphatase protein, such as by measuring a level of a phosphatase-encoding nucleic acid in a sample of cells from a subject e.g., mRNA or genomic DNA, or determining if a phosphatase gene has been mutated. Experimental data as provided in FIG. 1 indicates that phosphatase proteins of the present invention are expressed in the human brain, heart and liver etc. Specifically, a virtual northern blot shows expression in human total fetus, human germinal B cell, human fetal liver, human fetal liver spleen and human lymph node. In addition, PCR-based tissue screening panel indicates expression in human fetal brain, human brain, human heart, human liver, human lung, human placenta, and human thyroid.

Nucleic acid expression assays are useful for drug screening to identify compounds that modulate phosphatase nucleic acid expression.

The invention thus provides a method for identifying a compound that can be used to treat a disorder associated with nucleic acid expression of the phosphatase gene, particularly biological and pathological processes that are mediated by the phosphatase in cells and tissues that express it. Experimental data as provided in FIG. 1 indicates expression in the human total fetus, human germinal B cell, human fetal liver, human fetal liver spleen and human lymph node, as well as expression in human fetal brain, human brain, human heart, human liver, human lung, human placenta, and human thyroid tissues. The method typically includes assaying the ability of the compound to modulate the expression of the phosphatase nucleic acid and thus identifying a compound that can be used to treat a disorder characterized by undesired phosphatase nucleic acid expression. The assays can be performed in cell-based and cell-free systems. Cell-based assays include cells naturally expressing the phosphatase nucleic acid or recombinant cells genetically engineered to express specific nucleic acid sequences.

The assay for phosphatase nucleic acid expression can involve direct assay of nucleic acid levels, such as mRNA levels, or on collateral compounds involved in the signal pathway. Further, the expression of genes that are up- or down-regulated in response to the phosphatase protein signal pathway can also be assayed. In this embodiment the regulatory regions of these genes can be operably linked to a reporter gene such as luciferase.

Thus, modulators of phosphatase gene expression can be identified in a method wherein a cell is contacted with a candidate compound and the expression of mRNA determined. The level of expression of phosphatase mRNA in the presence of the candidate compound is compared to the level of expression of phosphatase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate phosphatase nucleic acid expression in cells and tissues that express the phosphatase. Experimental data as provided in FIG. 1 indicates that phosphatase proteins of the present invention are expressed in the human brain, heart and liver etc. Specifically, a virtual northern blot shows expression in human total fetus, human germinal B cell, human fetal liver, human fetal liver spleen and human lymph node. In addition, PCR-based tissue screening panel indicates expression in human fetal brain, human brain, human heart, human liver, human lung, human placenta, and human thyroid. Modulation includes both up-regulation (i.e. activation or agonization) or down-regulation (suppression or antagonization) or nucleic acid expression.

Alternatively, a modulator for phosphatase nucleic acid expression can be a small molecule or drug identified using the screening assays described herein as long as the drug or small molecule inhibits the phosphatase nucleic acid expression in the cells and tissues that express the protein. Experimental data as provided in FIG. 1 indicates expression in the human total fetus, human germinal B cell, human fetal liver, human fetal liver spleen and human lymph node, as well as expression in human fetal brain, human brain, human heart, human liver, human lung, human placenta, and human thyroid tissues.

The nucleic acid molecules are also useful for monitoring the effectiveness of modulating compounds on the expression or activity of the phosphatase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in phosphatase nucleic acid expression, and particularly in qualitative changes that lead to pathology. The nucleic acid molecules can be used to detect mutations in phosphatase genes and gene expression products such as mRNA. The nucleic acid molecules can be used as hybridization probes to detect naturally occurring genetic mutations in the phosphatase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the phosphatase gene associated with a dysfunction provides a diagnostic tool for an active disease or susceptibility to disease when the disease results from overexpression, underexpression, or altered expression of a phosphatase protein.

Individuals carrying mutations in the phosphatase gene can be detected at the nucleic acid level by a variety of techniques. FIG. 3 provides SNP information that has been found in a gene encoding the phosphatase protein of the present invention. The following variations were seen: G3114A, T4514G, A7570G, C11672G, A11897C, T14523C, C16586T, T16644C, A17969G, C18117T, C18518A, G19882A, A21465G, C21625T, C26291T, T28012C, T28030G, A33671C, A37703G and C39269G as substitutions, -20999T, -4004A as insertions and G20988- deletion. The changes in the amino acid sequence that these SNPs cause can readily be determined using the universal genetic code and the protein sequence provided in FIG. 2 as a base. As indicated by the data presented in FIG. 3, the map position was determined to be on chromosome 14 by ePCR, and confirmed with radiation hybrid mapping. As indicated by the data presented in FIG. 3, the gene provided by the present invention encoding a novel phosphatase maps to public BAC AC AL139317.2, which is known to be located on human chromosome 14. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a phosphatase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant phosphatase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/161101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the phosphatase gene in an individual in order to select an appropriate compound or dosage regimen for treatment. FIG. 3 provides SNP information that has been found in a gene encoding the phosphatase protein of the present invention. The following variations were seen: G3114A, T4514G, A7570G, C11672G, A11897C, T14523C, C16586T, T16644C, A17969G, C18117T, C18518A, G19882A, A21465G, C21625T, C26291T, T28012C, T28030G, A33671C, A37703G and C39269G as substitutions, -20999T, -4004A as insertions and G20988-deletion. The changes in the amino acid sequence that these SNPs cause can readily be determined using the universal genetic code and the protein sequence provided in FIG. 2 as a base.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control phosphatase gene expression in cells, tissues, and organisms. A DNA antisense nucleic acid molecule is designed to be complementary to a region of the gene involved in transcription, preventing transcription and hence production of phosphatase protein. An antisense RNA or DNA nucleic acid molecule would hybridize to the mRNA and thus block translation of mRNA into phosphatase protein.

Alternatively, a class of antisense molecules can be used to inactivate mRNA in order to decrease expression of phosphatase nucleic acid. Accordingly, these molecules can treat a disorder characterized by abnormal or undesired phosphatase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the phosphatase protein, such as substrate binding.

The nucleic acid molecules also provide vectors for gene therapy in patients containing cells that are aberrant in phosphatase gene expression. Thus, recombinant cells, which include the patient's cells that have been engineered ex vivo and returned to the patient, are introduced into an individual where the cells produce the desired phosphatase protein to treat the individual.

The invention also encompasses kits for detecting the presence of a phosphatase nucleic acid in a biological sample. Experimental data as provided in FIG. 1 indicates that phosphatase proteins of the present invention are expressed in the human brain, heart and liver etc. Specifically, a virtual northern blot shows expression in human total fetus, human germinal B cell, human fetal liver, human fetal liver spleen and human lymph node. In addition, PCR-based tissue screening panel indicates expression in human fetal brain, human brain, human heart, human liver, human lung, human placenta, and human thyroid. For example, the kit can comprise reagents such as a labeled or labelable nucleic acid or agent capable of detecting phosphatase nucleic acid in a biological sample; means for determining the amount of phosphatase nucleic acid in the sample; and means for comparing the amount of phosphatase nucleic acid in the sample with a standard. The compound or agent can be packaged in a suitable container. The kit can further comprise instructions for using the kit to detect phosphatase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the fill length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the phosphatase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the phosphatase gene of the present invention. FIG. 3 provides SNP information that has been found in a gene encoding the phosphatase protein of the present invention. The following variations were seen: G3114A, T4514G, A7570G, C11672G, A11897C, T14523C, C16586T, T16644C, A17969G, C18117T, C18518A, G19882A, A21465G, C21625T, C26291T, T28012C, T28030G, A33671C, A37703G and C39269G as substitutions, -20999T, -4004A as insertions and G20988-deletion. The changes in the amino acid sequence that these SNPs cause can readily be determined using the universal genetic code and the protein sequence provided in FIG. 2 as a base.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1 (1 982), Vol. 2 (1983), Vol. 3 (1985); Tijssen, P., *Practice and Theory of Enzyme Immunoassays: Laboratory Techniques in Biochemistry and Molecular Biology,* Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified phosphatase gene of the present invention can be routinely identified using the sequence information disclosed herein can be readily incorporated into one of the established kit formats which are well known in the art, particularly expression arrays.

Vectors/host cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage π, the lac, TRP, and TAC promoters from *E. coli,* the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterophosphatase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology. Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSecl (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 1 70:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory,* Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual 2nd, ed., Cold Spring Harbor Laboratory,* Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as phosphatases, appropriate secretion signals are incorporated into the vector. The signal sequence can be endogenous to the peptides or heterologous to these peptides.

Where the peptide is not secreted into the medium, which is typically the case with phosphatases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of vectors and host cells

The recombinant host cells expressing the peptides described herein have a variety of uses. First, the cells are useful for producing a phosphatase protein or peptide that can be further purified to produce desired amounts of phosphatase protein or fragments. Thus, host cells containing expression vectors are useful for peptide production.

Host cells are also useful for conducting cell-based assays involving the phosphatase protein or phosphatase protein fragments, such as those described above as well as other formats known in the art. Thus, a recombinant host cell expressing a native phosphatase protein is useful for assaying compounds that stimulate or inhibit phosphatase protein function.

Host cells are also useful for identifying phosphatase protein mutants in which these functions are affected. If the mutants naturally occur and give rise to a pathology, host cells containing the mutations are useful to assay compounds that have a desired effect on the mutant phosphatase protein (for example, stimulating or inhibiting function) which may not be indicated by their effect on the native phosphatase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a phosphatase protein and identifying and evaluating modulators of phosphatase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the phosphatase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the phosphatase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992).

Another example of a recombinase system is the FLP recombinase system of *S. cerevisiae* (O'Gorman et al. Science 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo phosphatase protein function, including substrate interaction, the effect of specific mutant phosphatase proteins on phosphatase protein function and substrate interaction, and the effect of chimeric phosphatase proteins. It is also possible to assess the effect of null mutations, that is mutations that substantially or completely eliminate one or more phosphatase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:
   (a) a nucleotide sequence that encodes a polypeptide comprising the amino acid sequence of SEQ ID NO:2;
   (b) a nucleotide sequence consisting of SEQ ID NO:1; and
   (c) a nucleotide sequence that is completely complementary to a nucleotide sequence of (a)–(b).

2. A nucleic acid vector comprising the nucleic acid molecule of claim 1.

3. A host cell containing the vector of claim 2.

4. A process for producing a polypeptide comprising SEQ ID NO:2 comprising culturing the host cell of claim 3 under conditions sufficient for the production of said polypeptide, and recovering said polypeptide.

5. An isolated polynucleotide consisting of the nucleotide sequence set forth in SEQ ID NO:1.

6. A vector according to claim 2, wherein said vector is selected from the group consisting of a plasmid, a virus, and a bacteriophage.

7. A vector according to claim 2, wherein said isolated nucleic acid molecule is inserted into said vector in proper orientation and correct reading frame such that a polypeptide comprising SEQ ID NO:2 may be expressed by a cell transformed with said vector.

8. A vector according to claim 7, wherein said isolated nucleic acid molecule is operatively linked to a promoter sequence.

* * * * *